United States Patent
Crystal et al.

(10) Patent No.: US 12,226,492 B2
(45) Date of Patent: Feb. 18, 2025

(54) GENE THERAPY FOR EOSINOPHILIC DISORDERS

(71) Applicant: Cornell University, Ithaca, NY (US)

(72) Inventors: Ronald G. Crystal, New York, NY (US); Odelya E. Pagovich, New York, NY (US); Katie Stiles, Bronx, NY (US)

(73) Assignee: Cornell University, Ithaca, NY (US)

( * ) Notice: Subject to any disclaimer, the term of this patent is extended or adjusted under 35 U.S.C. 154(b) by 529 days.

(21) Appl. No.: 16/959,090

(22) PCT Filed: Dec. 28, 2018

(86) PCT No.: PCT/US2018/067869
§ 371 (c)(1),
(2) Date: Jun. 29, 2020

(87) PCT Pub. No.: WO2019/133818
PCT Pub. Date: Jul. 4, 2019

(65) Prior Publication Data
US 2020/0330608 A1 Oct. 22, 2020

Related U.S. Application Data

(60) Provisional application No. 62/612,005, filed on Dec. 29, 2017.

(51) Int. Cl.
*C07K 16/44* (2006.01)
*A61K 48/00* (2006.01)
*C07K 16/28* (2006.01)
*C12N 15/86* (2006.01)

(52) U.S. Cl.
CPC ........ *A61K 48/005* (2013.01); *A61K 48/0075* (2013.01); *C07K 16/2851* (2013.01); *C07K 16/44* (2013.01); *C12N 15/86* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 6,207,155 | B1 | 3/2001 | Grimaldi et al. |
| 6,403,782 | B1 | 6/2002 | Luster et al. |
| 6,894,155 | B2 | 5/2005 | Mcfadden et al. |
| 7,141,653 | B2 | 11/2006 | Greenfeder et al. |
| 7,354,584 | B2 | 4/2008 | Reed et al. |
| 9,290,574 | B2 | 3/2016 | Kostic et al. |
| 9,546,215 | B2 | 1/2017 | Bebbington et al. |
| 2003/0092091 | A1 | 5/2003 | Abrahamson et al. |
| 2003/0099995 | A1 | 5/2003 | Walker et al. |
| 2003/0194404 | A1 | 10/2003 | Greenfeder et al. |
| 2004/0156847 | A1 | 8/2004 | Miura et al. |
| 2008/0267973 | A1 | 10/2008 | Wang et al. |
| 2015/0203578 | A1 | 7/2015 | Bebbington et al. |
| 2016/0296638 | A1 | 10/2016 | Crystal et al. |
| 2017/0073413 | A1 | 3/2017 | Bebbington et al. |
| 2017/0334985 | A1 | 11/2017 | Wu et al. |
| 2018/0155436 | A1 | 6/2018 | Orengo et al. |

FOREIGN PATENT DOCUMENTS

| | | |
|---|---|---|
| CN | 101848732 A | 9/2010 |
| CN | 112041338 A | 12/2020 |
| JP | 2017507945 A | 3/2017 |
| JP | 2021508719 A | 3/2021 |
| JP | 2023179525 A | 12/2023 |
| WO | WO-0121204 A1 | 3/2001 |
| WO | WO-0159142 A1 | 8/2001 |
| WO | WO-2013051435 A1 | 4/2013 |
| WO | WO-2015013115 A1 | 1/2015 |
| WO | WO-2015131155 A1 | 9/2015 |
| WO | WO-2016164920 A1 | 10/2016 |
| WO | WO-2017077391 A2 | 5/2017 |
| WO | WO-2017189805 A1 | 11/2017 |
| WO | WO-2018204871 A1 | 11/2018 |
| WO | WO-2019133818 A1 | 7/2019 |

OTHER PUBLICATIONS

"U.S. Appl. No. 16/959,090, Restriction Requirement mailed Jun. 29, 2022", 8 pgs.
"Japanese Application Serial No. 2020-536268, Voluntary Amendment Filed Dec. 22, 2021", w/English Claims, 11 pgs.
"Chinese Application Serial No. 201880090512.8, Office Action mailed Sep. 14, 2020", (w/ English Translation), 2 pgs.
"Chinese Application Serial No. 201880090512.8, Voluntary Amendment Filed Mar. 25, 2021", (w/ English Translation of Claims), 11 pgs.
"European Application Serial No. 18845394.8, Response filed Feb. 23, 2021 to Communication pursuant to Rules 161(1) and 162 EPC mailed Sep. 1, 2020", 8 pgs.
"International Application Serial No. PCT/US2018/067869, International Preliminary Report on Patentability mailed Jul. 1, 2020", 10 pgs.
"International Application Serial No. PCT/US2018/067869, International Search Report mailed May 17, 2019", 6 pgs.
"International Application Serial No. PCT/US2018/067869, Written Opinion mailed May 17, 2019", 8 pgs.
"RecName: RecName: Full=Ig gamma-2B chain C region; AltName: Full=Immunoglobulin heavy chain 1a", UniProtKB/Swiss-Prot: P20761.1, (Jul. 6, 2016), 8 pgs.
Celestin, Jocelyn, et al., "Eosinophilic Disorders in Various Diseases", Curr Allergy Asthma Rep, 12, (2012), 18-24.
Chia-Jen, Wu, et al., "Pseudotyped Adeno-Associated Virus 2/9-Delivered CCL1 shRNA Alleviates Lung Inflammation in an Allergen-Sensitized Mouse Model", Human Gene Therapy, vol. 23 No. 11, (Nov. 1, 2012), 10 pgs.

(Continued)

*Primary Examiner* — Benjamin P Blumel
(74) *Attorney, Agent, or Firm* — Schwegman Lundberg & Woessner, P.A.

(57) ABSTRACT

Compositions and methods for eosinophilia in a mammal are provided. In one embodiment, the composition is a viral gene therapy vector, and a single dose of the vector reduces increased numbers of eosinophils in a mammal.

20 Claims, 28 Drawing Sheets

Specification includes a Sequence Listing.

(56) References Cited

OTHER PUBLICATIONS

Elsner, J., et al., "Surface and mRNA expression of the CD52 antigen by human eosinophils but not by neutrophils", Blood, 88, (1996), 4684-4693.

Holgate, Stephen, et al., "The anti-inflammatory effects of omalizumab confirm the central role of IgE in allergic", The Journal of Allergy and Clinical Immunology, 115(3), (Mar. 2005), 459-465.

Johansson, Mats W, "Eosinophil Activation Status in Separate Compartments and Association with Asthma", Frontiers in Medicine, vol. 4, (Jun. 12, 2017), 10 pgs.

Meijia, Rojelio, et al., "Evaluation and Differential Diagnosis of Marked, Persistent Eosinophilla", Seminars in Hematology, 49(2), (2012), 149-159.

Nutku, et al., "Ligation of Siglec-8 selective tnechanisl 11 for induction of human eosinophil apoptosis", Blood, vol. 101, (Jan. 1, 2003), 7 pgs.

Pagovich, Odelya E, et al., "Anti-higE gene therapy of peanut-induced anaphylaxis in a humanized murine model of peanut allergy", Journal of Allergy and Clinical Immunology Elsevier, Amsterdam, Nl, vol. 138, No. 6,, (Jun. 29, 2016), 18 pgs.

Pagovich, Odelya E, et al., "Gene Therapy for Chronic Eosinophilic Leukemia", Molecular Therapy Nature Publishing Group, GB vol. 26, No. 5 Suppl. 1, [Online] Retrieved from the internet: <https //www sci encedi rect.com/journal/ molecular-therapy>, (Apr. 30, 2018), 161-162.

Rosenberg, Helene F., et al., "Eosinophils: changing perspectives in health and disease", Nature Reviews—Immunology, 13, (Jan. 2013), 9-22.

Taverna, J. A., et al., "Infliximab as a Therapy for Idiopathic Hypereosinophilic Syndrome", Arch Dermatol., 143(9), (Sep. 2007), 1110-1112.

Valent, Peter, et al., "Pathogenesis and classification of eosinophil disorders: a review of recent developments in the field", Expert Review of Hematology, 5:2, (2012), 157-176.

Zavorotinskaya, Tatiana, et al., "Treatment of experimental asthma by long-term gene therapy directed against IL-4 and IL-13", Molecular Therapy the Journal of the American Society of Gene Therapy Feb. 2003, vol. 7, No. 2, (Feb. 2003), 18 pgs.

Zeng, Daxiong, et al., "Recombinant Adeno-Associated Virus Vector-Mediated Delivery of Antisense Interleukin-5 Gene Attenuates Airway Remodeling in Allergic Rats", International Archives of Allergy and Immunology vol. 154, No. 3, (2011), 9 pgs.

Zimmermann, N, et al., "Siglec-F antibody administration to mice selectively reduces blood and tissue eosinophils", Allergy Wiley-Blackwell Publishing Ltd, United Kingdom, vol. 63, No. 9, (Sep. 1, 2008), 10 pgs.

"Chinese Application Serial No. 201880090512.8, Office Action mailed Nov. 2, 2022", (w/ English Translation), 24 pgs.

"Chinese Application Serial No. 201880090512.8, Response Filed Mar. 15, 2023 to Office Action mailed Nov. 2, 2022", W/ English Claims, 12 pgs.

"Japanese Application Serial No. 2020-536268, Notification of Reasons for Rejection mailed Jan. 12, 2023", (w/ English Translation), 12 pgs.

Camilleri, Anna E., et al., "Gene therapy for a murine model of eosinophilic esophagitis", Basic and Translational Allergy Immunology, Allergy, European Journal of Allervy and Clinical Immunolgy, onlinelibrary.wiley.com/doi/10.1111/all.14822 by Cornell University, Received: Oct. 16, 2020, Revised: Jan. 5, 2021, Accepted: Jan. 15, 2021, 2741-2752.

Pagovich, Odelya E., et al., "Anti-hIgE gene therapy of peanut-induced anaphylaxis in a humanized murine model of peanut allergy", J Allergy Clin Immunol , 138(6), (2016), 1652-1662.

"Japanese Application Serial No. 2020-536268, Examiners Decision of Final Refusal mailed May 22, 2023", with English translation, 10 pages.

"European Application Serial No. 18845394.8, Communication Pursuant to Article 94(3) EPC mailed May 2, 2023", 6 pgs.

"European Application Serial No. 18845394.8, Response Filed Aug. 18, 2023 to Communication Pursuant to Article 94(3) EPC mailed May 2, 2023", 8 pgs.

"Chinese Application Serial No. 201880090512.8, Office Action mailed Sep. 9, 2023", w machine English Translation, 22 pgs.

"Korean Application Serial No. 10-2020-7021914, Notice of Preliminary Rejection mailed Sep. 19, 2023", w English translation, 15 pgs.

"Japanese Application Serial No. 2023-155691, Voluntary Amendment Filed Oct. 19, 2023", W English Claims, 9 pgs.

Carroll, D.J., "Siglec-8 Signals Through a Non-Canonical Pathway to Cause Human Eosinophil Death", Front Immunol 2021;12(737988, doi:10.3389 fimmu.2021.73798, (2021), 15 pgs.

Dellon, E.S., "Determination of Biopsy Yield That Optimally Detects Eosinophilic Gastritis and or Duodenitis in a Randomized Trial of Lirentelimab", Clin Gastroenterol Hepatol 2022, 20(3), 535-545. e15, doi:10.1016 j.cgh.2021.05.053, (2022), 26 pgs.

Dellon, E.S., "Biologics in eosinophilic gastrointestinal diseases", Ann Allergy Asthma Immunol 2022, doi:10.1016 j.anai.2022.06. 015, (2022), 6 pgs.

Dispenza, M.C., "Targeting the FcRI Pathway as a Potential Strategy to Prevent Food Induced Anaphylaxis", Front Immunol 2020, 11 614402, doi:10.3389 fimmu.2020.614402, (2020), 8 pgs.

Duan, S., "Nanoparticles Displaying Allergen and Siglec 8 Ligands Suppress IgE FcRI Mediated Anaphylaxis and Desensitize Mast Cells to Subsequent Antigen Challenge", J Immunol 2021, 206, 10, 2290-2300, doi:10.4049 jimmunol.1901212, (2021), 25 pgs.

Fiocchi, A., "The use of biologics in food allergy", Clin Exp Allergy 2021, 51(8), 1006-1018, doi: 10.1111 cea.13897, (2021).

Gebremeskel, S., "Mast Cell and Eosinophil Activation Are Associated With COVID 19 and TLR Mediated Viral Inflammation, Implications for an Anti Siglec 8 Antibody", Front Immunol 2021, 12, 650331, doi:10.3389fimmu.2021.650331, (2021), 12 pgs.

Gonzalez-Gil, A., "Isolation, identification, and characterization of the human airway ligand for the eosinophil and mast cell immunoinhibitory receptor Siglec-8", J Allergy Clin Immunol 2021, 147(4), 1442-1452, doi:10.1016 j.jaci.2020.08.001, (2021), 24 pgs.

Hirano, I., "AK002, an Anti-Siglec-8 Antibody, Depletes Tissue Eosinophils and Improves Dysphagia Symptoms in Patients with Eosinophilic Esophagitis", J Allergy Clin Immunol 2020, 145(2), AB167, (2020), 2 pgs.

Kerr, S.C., "An anti-siglec-8 antibody depletes sputum eosinophils from asthmatic subjects and inhibits lung mast cells", Clin Exp Allergy 2020, 50(8), 904-914, doi:10.1111 cea.13681, (2020), 17 pgs.

Korver, W., "The Inhibitory Receptor Siglec-8 Interacts With FceRI and Globally Inhibits Intracellular Signaling in Primary Mast Cells Upon Activation", Front Immunol 2022, 13 833728, doi:10.3389 fimmu.2022.833728, (2022), 16 pgs.

Kroezen, B.S., "A Potent Mimetic of the Siglec 8 Ligand 6 Sulfo-Sialyl Lewis", ChemMedChem 2020, 15,18, 1706-1719, doi:10. 1002 cmdc.202000417, (2020), 14 pgs.

Kuang, F.L., "Lessons learned from targeting eosinophils in human disease", Semin Immunopathol 2021, 43, 3459-475, doi:10.1007 s00281-021-00849-w, (2021), 29 pgs.

Lucendo, A.J., "Targeted Therapies for Eosinophilic Gastrointestinal Disorders", BioDrugs 2020, 34, 4, 477-493, doi:10.1007 s40259-020-00427-w, (2020), 17 pgs.

Morshed, N., "Phosphoproteomics identifies microglial Siglec F inflammatory response during neurodegeneration", Mol Syst Biol 2020, 16, 12 e9819, doi:10.15252 msb.20209819, (2020), 27 pgs.

Nycholat, C.M., "A Sulfonamide Sialoside Analogue for Targeting Siglec 8 and F on Immune Cells", J Am Chem Soc 2019, 141, 36, 14032-14037, doi:10.1021 jacs.9b05769, (2019), 98 pgs.

Peterson, K., "Emerging Therapies for Eosinophilic Gastrointestinal Diseases", J Allergy Clin Immunol Pract 2021, 9,9,3276-3281, doi:10.1016 j.jaip.2021.07.031, (2021), 26 pgs.

Schanin, J., "A monoclonal antibody to Siglec-8 suppresses non-allergic airway inflammation and inhibits IgE-independent mast cell activation", Mucosal Immunol 2021, 14(2):366-376, doi:10.1038 s41385-020-00336-9, (2021), 11 pgs.

(56) References Cited

OTHER PUBLICATIONS

Trebo, A., "First Evidence for a Role of Siglec 8 in Breast Cancer", Int J Mol Sci 2021,22, 4, doi:10.3390 ijms22042000, (2021), 20 pgs.

Visaggi, P., "Treatment Trends for Eosinophilic Esophagitis and the Other Eosinophilic Gastrointestinal Diseases: Systematic Review of Clinical Trials", Dig Liver Dis 2022, doi:10.1016 j.dld.2022.05.004, (2022), 19 pgs.

"Kegg Drug: Lirentelimab", [Online]. Retrieved from the Internet: <URL: https://protect-us.mimecast.com/s/w2uLC73OWPFz7VDYs8cNjF?domain=genome.jp>, (Accessed Sep. 11, 23), 1 pg.

Altrichter, Sabine, et al., "An open-label, proof-of-concept study of lirentelimab for antihistamine-resistant chronic spontaneous and inducible urticaria", J Allergy Clin Immunol, vol. 146, No. 5, (May 2022), 15 pgs.

Anesi, Stephen, et al., "Lirentelimab for severe and chronic forms of allergic conjunctivitis", J Allergy Clin Immunol, (Sep. 2022), 631-639.

Dellon, Evan, et al., "Anti-Siglec-8 Antibody for Eosinophilic Gastritis and Duodenitis", N Engl J Med., 383(17), pp. 1624-1634, (Oct. 22, 20), 17 pgs.

"Canadian Application Serial No. 3,087,063, Examiners Rule 86(2) Report mailed Dec. 4, 2023", 4 pgs.

"Chinese Application Serial No. 201880090512.8, Decision of Rejection mailed Dec. 11, 2023", w/ English Claims, 8 pgs.

"Chinese Application Serial No. 201880090512.8, Response Filed Nov. 24, 2023 to Office Action mailed Sep. 9, 2023", W/ English Claims, 14 pgs.

"Korean Application Serial No. 10-2020-7021914, Final Office Action mailed Dec. 27, 2023", w/o English translation, 3 pgs.

"Korean Application Serial No. 10-2020-7021914, Response Filed Nov. 20, 2023 to Notice of Preliminary Rejection mailed Sep. 19, 2023", W/ English Claims, 22 pgs.

"Canadian Application Serial No. 3,087,063, Response Filed Apr. 3, 2024 to Examiners Rule 86(2) Report mailed Dec. 4, 2023", 19 pgs.

"Chinese Application Serial No. 201880090512.8, Response Filed Mar. 26, 2024 to Decision of Rejection mailed Dec. 11, 2023", W/ English Claims, 66 pgs.

"Korean Application Serial No. 10-2020-7021914, Response filed Mar. 27, 2024 to Final Office Action mailed Dec. 27, 2023", W/ English Claims, 27 pgs.

"Japanese Application Serial No. 2020-536268, Written Amendment filed Apr. 13, 2023 in response to Notification of Reasons for Rejection mailed Jan. 16, 2023", with English claims, 28 pages.

Dondelinger, Mathieu, et al., "Understanding the Significance and Implications of Antibody Numbering and Antigen-Binding Surface/Residue Definition", Frontiers in Immunology, 15 pgs.

Pagovich, Odelya E., et al., "Anti-hIgE gene therapy of peanut-induced anaphylaxis in a humanized murine model of peanut allergy", J. Allergy Clin. Immunol., 138, (2016), 1652.

"Israeli Application Serial No. 275613, Office Action mailed Sep. 3, 2024", w/ English translation, 4 pgs.

"Japanese Application Serial No. 2023-155691, Notification of Reasons for Rejection mailed Oct. 3, 2024", w/ English Translation, 9 pgs.

Blood Smear, CEL-NOS

Blood Smear, PBS Mouse

Scale bars = 0.1 mm

Blood Smear, AAVrh.10mIL-5 Mouse, 2 wk

Naive – Lung

AAVrh.10mIL-5 – lung

Naive – Liver

AAVrh.10mIL-5 – Liver

Naive - Heart

AAVrh.10mIL-5 – Heart

Expression of AAVrh.10mAnti-Eos in Wild-Type Mice (Balb/c)

AAVrh.10mAnti-Eos Reduces Eosinophil Numbers in the CEL-NOS Murine Model (Balb/c)

Scale Bars = 0.1 mm

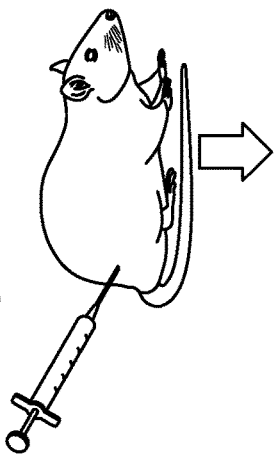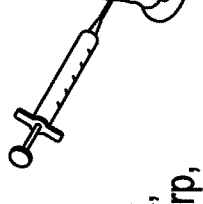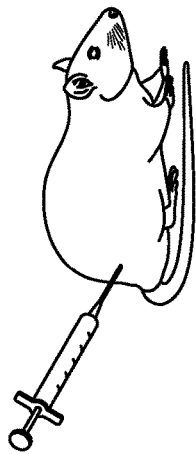
FIG. 9A
FIG. 9B

Blood Smear, PBS Mouse

Scale Bars = 0.1 mm

Blood Smear, AAVrh.10mIL-5 Mouse, 2 wk

AAVrh.10mAnti-Eos Therapy in the CEL-NOS Murine Model (NSG)

- NSG (6-8wk, n=5 males/grp, n=5 females/grp)
- AAVrh.10mIL-5 $5 \times 10^{10}$ gc
- Naïve ⬇ 4 wk

- AAVrh.10mAnti-Eos $10^{11}$
- AAVrh.10RatIgGcontrol $10^{11}$
- PBS

⬇

Evaluate
- Absolute eosinophil count(blood)
- Eosinophil apoptosis
- Eosinophil infiltration in organs

AAVrh.10mAnti-Eos Reduces Eosinophil Numbers in the CEL-NOS Murine Model (NSG Females)

Mouse Model

- AAVrh.10mIL-5 $5 \times 10^{10}$ gc
- Naïve (n=3F)

- NSG (6-8wk females)

⇩ 4 wk

- AAVrh.10mAnti-Eos $10^{11}$ (n=5F)
- AAVrh.10RatIgGcontrol $10^{11}$ (n=5F)
- PBS (n=5F)

⇩ 0-22 wk

Evaluate
- Absolute eosinophil count

AAVrh.10mAnti-Eos Reduces Eosinophil Numbers in the CEL-NOS Murine Model (NSG Males)

Mouse Model

- AAVrh.10mIL-5 $5 \times 10^{10}$ gc
- Naïve (n=5M)

- NSG (6-8wk males)

⬇ 4 wk

- AAVrh.10mAnti-Eos $10^{11}$ (n=5M)
- AAVrh.10RatIgGcontrol $10^{11}$ (n=5M)
- PBS (n=5M)

⬇ 0-18 wk

Evaluate
- Absolute eosinophil count

AAVrh.10mAnti-Eos Reduces Eosinophil
Numbers in the CEL-NOS Murine Model (Male NSG;3)

AAVrh.10mIL-5, $5 \times 10^{10}$ gc +
AAVrh.10IgGcontrol gc, 6 wk

AAVrh.10mIL-5, $5 \times 10^{10}$ gc +
AAVrh.10mAnti-Eos, $10^{11}$ gc, 6 wk

Scale bars
= 0.1 mm

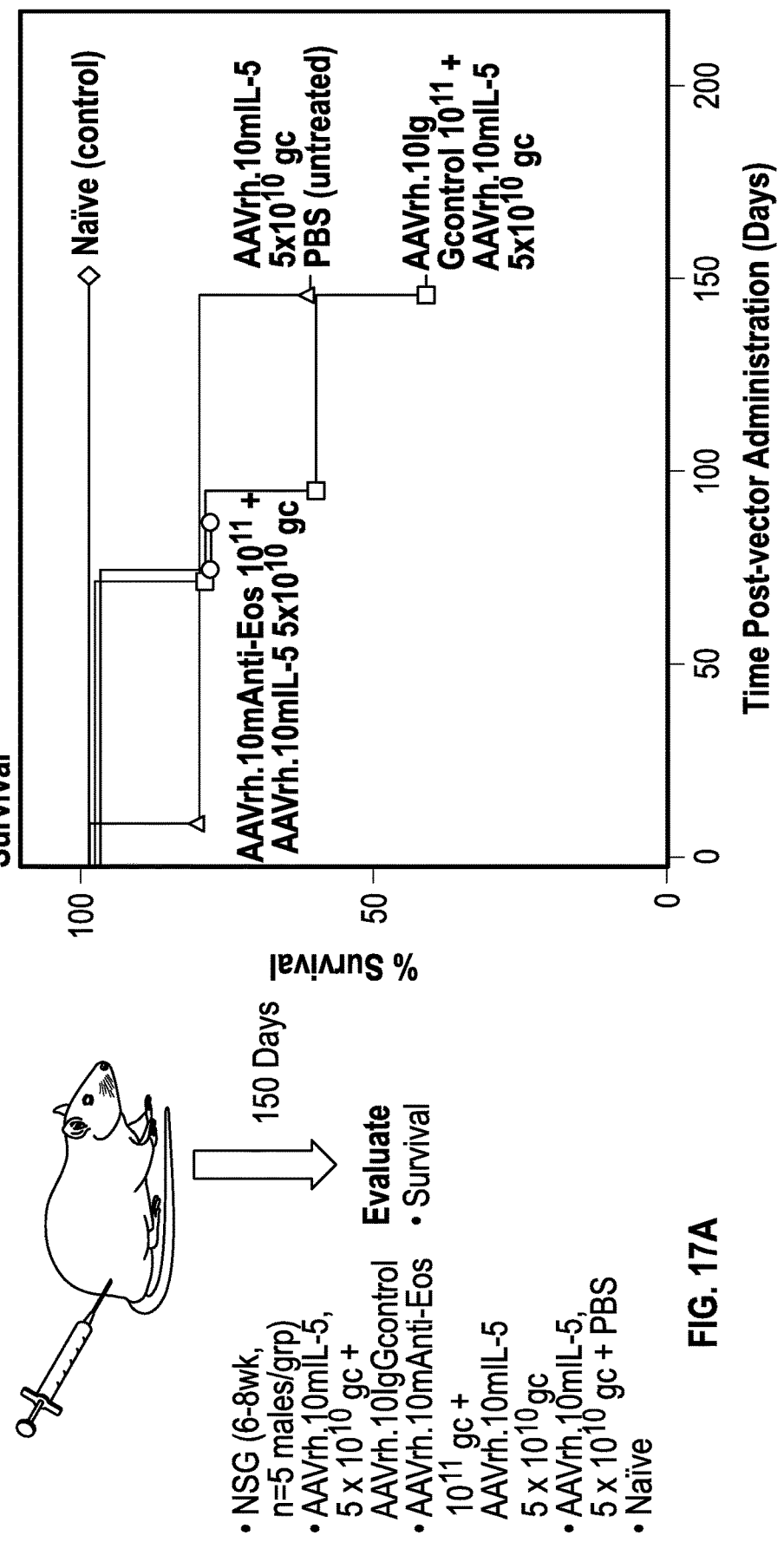

SEQUENCE LISTING

```
<160> NUMBER OF SEQ ID NOS: 61

<210> SEQ ID NO 1
<211> LENGTH: 417
<212> TYPE: DNA
<213> ORGANISM: Artificial Sequence
<220> FEATURE:
<223> OTHER INFORMATION: A synthetic nucleic acid sequence

<400> SEQUENCE: 1
atggctgtcc tggtgctgtt gctctgcctg ctgacatttc caagctgtgt cctgtcccag      60
gtgcagctga aggagtcagg acctggtctg gtgcagccct cacagacttt gtctctcacc     120
tgcactgtct ctgggttctc actagccagc tatcatgtaa gctgggttcg ccagcctcca     180
ggaaaaggtc tggagtggat gggactaata tggactggtg aagcacaac atataattca     240 cttctcaaat cccgactgag catcagcagg gacacctcca agagccaagt tttcctaaag     300
atgaacagtc tgcaaactga agacacagcc acttactact gtgccagagt tgggggaggg     360
aatagtgcgc tatactttga ttattggggc caaggagtca tggtcacagt ctcctca       417

<210> SEQ ID NO 2
<211> LENGTH: 324
<212> TYPE: DNA
<213> ORGANISM: Artificial Sequence
<220> FEATURE:
<223> OTHER INFORMATION: A synthetic nucleic acid sequence

<400> SEQUENCE: 2
gacatccaga tgacacagtc tccagcttcc ctgtctgcat ctctgggaga aactgtcacc      60
atcgaatgtc gagcaagtga ggacatttac accggtttag catggtatca ccagaagcca     120
gggaaatctc ctcaactcct gatctataat gcaaatagct tgcagtctgg ggtcccatca     180
cggttcagtg gcagtggatc tggtacacag tattctctca agataaacag cctgcagtct     240
gaagatgtcg caagttattt ctgtcaacag tattacaatt atccgctcac gttcggttct     300
gggaccaagc tggagatcaa acgg                                            324

<210> SEQ ID NO 3
<211> LENGTH: 240
<212> TYPE: PRT
<213> ORGANISM: Artificial Sequence
<220> FEATURE:
<223> OTHER INFORMATION: A synthetic amino acid sequence

<400> SEQUENCE: 3

Met Glu Ser Gln Thr Gln Val Leu Met Ser Leu Leu Leu Trp Ile Ser
1               5                  10                  15

Gly Thr Cys Gly Asp Ile Val Met Thr Gln Ser Pro Ser Ser Leu Ala
            20                  25                  30

Val Ser Ala Gly Glu Thr Val Thr Ile Asn Cys Lys Ser Ser Gln Ser
        35                  40                  45

Leu Leu Tyr Ser Gly Asn Gln Lys Asn Tyr Leu Ala Trp Tyr Gln Gln
    50                  55                  60
```

```
Lys Pro Gly Gln Ser Pro Lys Leu Leu Ile Ser Trp Ala Ser Thr Arg
 65                  70                  75                  80

Gln Ser Gly Val Pro Asp Arg Phe Ile Gly Ser Gly Ser Gly Thr Asp
             85                  90                  95

Phe Thr Leu Thr Ile Ser Ser Val Gln Ala Glu Asp Leu Ala Ile Tyr
            100                 105                 110

Tyr Cys Gln Gln Asn Phe Asp Thr Pro Pro Thr Phe Gly Ser Gly Thr
        115                 120                 125

Lys Leu Glu Ile Lys Arg Ala Asp Ala Ala Pro Thr Val Ser Ile Phe
130                 135                 140

Pro Pro Ser Thr Glu Gln Leu Ala Thr Gly Gly Ala Ser Val Val Cys
145                 150                 155                 160

Leu Met Asn Asn Phe Tyr Pro Arg Asp Ile Ser Val Lys Trp Lys Ile
                165                 170                 175

Asp Gly Thr Glu Arg Arg Asp Gly Val Leu Asp Ser Val Thr Asp Gln
            180                 185                 190

Asp Ser Lys Asp Ser Thr Tyr Ser Met Ser Ser Thr Leu Ser Leu Thr
        195                 200                 205

Lys Ala Asp Tyr Glu Ser His Asn Leu Tyr Thr Cys Glu Val Val His
210                 215                 220

Lys Thr Ser Ser Ser Pro Val Val Lys Ser Phe Asn Arg Asn Glu Cys
225                 230                 235                 240

<210> SEQ ID NO 4
<211> LENGTH: 333
<212> TYPE: PRT
<213> ORGANISM: Artificial Sequence
<220> FEATURE:
<223> OTHER INFORMATION: A synthetic amino acid sequence

<400> SEQUENCE: 4

Ala Gln Thr Thr Ala Pro Ser Val Tyr Pro Leu Ala Pro Gly Cys Gly
1               5                   10                  15

Asp Thr Thr Ser Ser Thr Val Thr Leu Gly Cys Leu Val Lys Gly Tyr
            20                  25                  30

Phe Pro Glu Pro Val Thr Val Thr Trp Asn Ser Gly Ala Leu Ser Ser
        35                  40                  45

Asp Val His Thr Phe Pro Ala Val Leu Gln Ser Gly Leu Tyr Thr Leu
    50                  55                  60

Thr Ser Ser Val Thr Ser Ser Thr Trp Pro Ser Gln Thr Val Thr Cys
 65                  70                  75                  80

Asn Val Ala His Pro Ala Ser Ser Thr Lys Val Asp Lys Lys Val Glu
             85                  90                  95

Arg Arg Asn Gly Gly Ile Gly His Lys Cys Pro Thr Cys Pro Thr Cys
            100                 105                 110

His Lys Cys Pro Val Pro Glu Leu Leu Gly Gly Pro Ser Val Phe Ile
        115                 120                 125

Phe Pro Pro Lys Pro Lys Asp Ile Leu Leu Ile Ser Gln Asn Ala Lys
130                 135                 140

Val Thr Cys Val Val Val Asp Val Ser Glu Glu Glu Pro Asp Val Gln
145                 150                 155                 160

Phe Ser Trp Phe Val Asn Asn Val Glu Val His Thr Ala Gln Thr Gln
                165                 170                 175

Pro Arg Glu Glu Gln Tyr Asn Ser Thr Phe Arg Val Val Ser Ala Leu
            180                 185                 190
```

```
Pro Ile Gln His Gln Asp Trp Met Ser Gly Lys Glu Phe Lys Cys Lys
            195                 200                 205

Val Asn Asn Lys Ala Leu Pro Ser Pro Ile Glu Lys Thr Ile Ser Lys
    210                 215                 220

Pro Lys Gly Leu Val Arg Lys Pro Gln Val Tyr Val Met Gly Pro Pro
225                 230                 235                 240

Thr Glu Gln Leu Thr Glu Gln Thr Val Ser Leu Thr Cys Leu Thr Ser
                245                 250                 255

Gly Phe Leu Pro Asn Asp Ile Gly Val Glu Trp Thr Ser Asn Gly His
            260                 265                 270

Ile Glu Lys Asn Tyr Lys Asn Thr Glu Pro Val Met Asp Ser Asp Gly
        275                 280                 285

Ser Phe Phe Met Tyr Ser Lys Leu Asn Val Glu Arg Ser Arg Trp Asp
    290                 295                 300

Ser Arg Ala Pro Phe Val Cys Ser Val Val His Glu Gly Leu His Asn
305                 310                 315                 320

His His Val Glu Lys Ser Ile Ser Arg Pro Pro Gly Lys
                325                 330

<210> SEQ ID NO 5
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Ser Met Glu Tyr Trp Gly Gln
            100                 105                 110

Gly Thr Thr Val Thr Val Ser Ser
        115                 120

<210> SEQ ID NO 6
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 6

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45
```

```
Ser Thr Ser Asn Leu Ala Ser Gly Ile Pro Ala Arg Phe Ser Gly Ser
 50                  55                  60

Gly Ser Gly Thr Asp Phe Thr Leu Thr Ile Ser Ser Leu Glu Pro Glu
 65                  70                  75                  80

Asp Phe Ala Val Tyr Tyr Cys Gln Gln Arg Ser Ser Tyr Pro Phe Thr
                 85                  90                  95

Phe Gly Pro Gly Thr Lys Leu Asp Ile Lys
            100                 105

<210> SEQ ID NO 7
<211> LENGTH: 329
<212> TYPE: PRT
<213> ORGANISM: Artificial Sequence
<220> FEATURE:
<223> OTHER INFORMATION: A synthetic amino acid sequence

<400> SEQUENCE: 7

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 8
<211> LENGTH: 107
<212> TYPE: PRT
<213> ORGANISM: Artificial Sequence
<220> FEATURE:
<223> OTHER INFORMATION: A synthetic amino acid sequence

<400> SEQUENCE: 8

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 9
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 9

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ile Tyr
            20                  25                  30

Gly Ala His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Ile Asn Ser Leu Gln Thr Asp Asp Thr Ala Leu Tyr Tyr Cys Ala
                85                  90                  95

Arg Asp Gly Ser Ser Pro Tyr Tyr Ser Met Glu Tyr Trp Gly Gln
            100                 105                 110

Gly Thr Ser Val Thr Val Ser Ser
        115                 120

<210> SEQ ID NO 10
<211> LENGTH: 120
<212> TYPE: PRT
<213> ORGANISM: Artificial Sequence
<220> FEATURE:
<223> OTHER INFORMATION: A synthetic amino acid sequence -continued

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 11
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ile Tyr
            20                  25                  30

Gly Ala His Trp Val Arg Gln Ala Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ile Tyr
            20                  25                  30

Gly Ala His Trp Val Arg Gln Ala Pro Gly Lys Gly Leu Glu Trp Val
        35                  40                  45

```
Ser Val Ile Trp Ala Gly Gly Ser Thr Asn Tyr Asn Ser Ala Leu Met
 50                  55                  60

Ser Arg Phe Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
            115                 120

<210> SEQ ID NO 13
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 13

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Ile Tyr
                 20                  25                  30

Gly Ala His Trp Val Arg Gln Ala Pro Gly Lys Gly Leu Glu Trp Leu
             35                  40                  45

Ser Val Ile Trp Ala Gly Gly Ser Thr Asn Tyr Asn Ser Ala Leu Met
 50                  55                  60

Ser Arg Phe Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
            115                 120

<210> SEQ ID NO 14
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 14

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Ile Tyr
                 20                  25                  30

Gly Ala His Trp Val Arg Gln Ala Pro Gly Lys Gly Leu Glu Trp Val
             35                  40                  45

Gly Val Ile Trp Ala Gly Gly Ser Thr Asn Tyr Asn Ser Ala Leu Met
 50                  55                  60

Ser Arg Phe Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                 85                  90                  95

Arg Asp Gly Ser Ser Pro Tyr Tyr Tyr Ser Met Glu Tyr Trp Gly Gln
```

Gly Thr Thr Val Thr Val Ser Ser
        115                 120

<210> SEQ ID NO 15
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Phe Ser Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 17
<211> LENGTH: 120
<212> TYPE: PRT
<213> ORGANISM: Artificial Sequence
<220> FEATURE:

<223> OTHER INFORMATION: A synthetic amino acid sequence

<400> SEQUENCE: 17

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ile Tyr
            20                  25                  30

Gly Ala His Trp Ile Arg Gln Pro Pro Gly Lys Gly Leu Glu Trp Ile
        35                  40                  45

Gly Val Ile Trp Ala Gly Gly Ser Thr Asn Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Leu Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ile Tyr
            20                  25                  30

Gly Ala His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Leu Val Thr Val Ser Ser
        115                 120

<210> SEQ ID NO 19
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val

```
                35                  40                  45
Gly Val Ile Trp Ala Gly Gly Ser Thr Asn Tyr Asn Ser Ala Leu Met
        50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Gly Met Glu Tyr Trp Gly Gln
            100                 105                 110

Gly Thr Thr Val Thr Val Ser Ser
        115                 120
```

<210> SEQ ID NO 20
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 20

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Asp Tyr Trp Gly Gln
            100                 105                 110

Gly Thr Thr Val Thr Val Ser Ser
        115                 120
```

<210> SEQ ID NO 21
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 21

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95
```

Arg Asp Gly Ser Ser Pro Tyr Tyr Tyr Ser Met Glu Val Trp Gly Gln
            100                 105                 110

Gly Thr Thr Val Thr Val Ser Ser
            115                 120

<210> SEQ ID NO 22
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
            35                  40                  45

Gly Val Ile Trp Ala Gly Gly Ser Thr Asn Tyr Asn Ser Ala Leu Met
        50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Gly Met Asp Val Trp Gly Gln
            100                 105                 110

Gly Thr Thr Val Thr Val Ser Ser
            115                 120

<210> SEQ ID NO 23
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 23

Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 24
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 25
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 25

Glu Ile Ile Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 26
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 26

Glu Ile Ile Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 27
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 27

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Phe Gln Gln Lys Pro Gly Gln Ala Pro Arg Leu Trp Ile Tyr
            35                  40                  45

Ser Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 28
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 28

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Phe Gln Gln Lys Pro Gly Gln Ala Pro Arg Leu Leu Ile Tyr
            35                  40                  45

Ser Thr Ser Asn Leu Ala Ser Gly Val Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 29
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 29

Glu Ile Val Leu Thr Gln Ser Pro Ala Thr Leu Ser Leu Ser Pro Gly

-continued

```
                1               5                  10                 15
Glu Arg Ala Thr Leu Ser Cys Ser Ala Thr Ser Ser Val Ser Tyr Met
            20                  25                 30

His Trp Phe Gln Gln Lys Pro Gly Gln Ala Pro Arg Leu Leu Ile Tyr
        35                  40                 45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
                100                 105

<210> SEQ ID NO 30
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 30

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
                100                 105

<210> SEQ ID NO 31
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 31

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Tyr Thr
                85                  90                  95
```

Phe Gly Pro Gly Thr Lys Leu Asp Ile Lys
            100                 105

<210> SEQ ID NO 32
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 32

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Tyr Thr
                85                  90                  95

Phe Gly Pro Gly Thr Lys Leu Asp Ile Lys
            100                 105

<210> SEQ ID NO 33
<211> LENGTH: 449
<212> TYPE: PRT
<213> ORGANISM: Artificial Sequence
<220> FEATURE:
<223> OTHER INFORMATION: A synthetic amino acid sequence

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
            435                 440                 445

Gly

<210> SEQ ID NO 34
<211> LENGTH: 213
<212> TYPE: PRT
<213> ORGANISM: Artificial Sequence
<220> FEATURE:
<223> OTHER INFORMATION: A synthetic amino acid sequence

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
            85                  90                  95

```
Phe Gly Pro Gly Thr Lys Leu Asp Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 35
<211> LENGTH: 213
<212> TYPE: PRT
<213> ORGANISM: Artificial Sequence
<220> FEATURE:
<223> OTHER INFORMATION: A synthetic amino acid sequence

<400> SEQUENCE: 35

```
Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Phe Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 36
<211> LENGTH: 329

<212> TYPE: PRT
<213> ORGANISM: Artificial Sequence
<220> FEATURE:
<223> OTHER INFORMATION: A synthetic amino acid sequence

<400> SEQUENCE: 36

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 37
<211> LENGTH: 326
<212> TYPE: PRT
<213> ORGANISM: Artificial Sequence
<220> FEATURE:
<223> OTHER INFORMATION: A synthetic amino acid sequence

<400> SEQUENCE: 37

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
            325

<210> SEQ ID NO 38
<211> LENGTH: 107
<212> TYPE: PRT
<213> ORGANISM: Artificial Sequence
<220> FEATURE:
<223> OTHER INFORMATION: A synthetic amino acid sequence

<400> SEQUENCE: 38

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

```
Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105

<210> SEQ ID NO 39
<211> LENGTH: 444
<212> TYPE: PRT
<213> ORGANISM: Artificial Sequence
<220> FEATURE:
<223> OTHER INFORMATION: A synthetic amino acid sequence

<400> SEQUENCE: 39

Gln Val Gln Leu Lys Arg Ala Ser Gly Pro Gly Leu Val Ala Pro Ser
1               5                   10                  15

Gln Ser Leu Ser Ile Thr Cys Thr Val Ser Gly Phe Ser Leu Thr Ile
            20                  25                  30

Tyr Gly Ala His Trp Val Arg Gln Pro Pro Gly Lys Gly Leu Glu Trp
            35                  40                  45

Leu Gly Val Ile Trp Ala Gly Gly Ser Thr Asn Tyr Asn Ser Ala Leu
        50                  55                  60

Met Ser Arg Leu Ser Ile Ser Lys Asp Asn Ser Lys Ser Gln Val Phe
65                  70                  75                  80

Leu Lys Ile Asn Ser Leu Gln Thr Asp Asp Thr Ala Leu Tyr Tyr Cys
                85                  90                  95

Ala Arg Asp Gly Ser Ser Pro Tyr Tyr Tyr Ser Met Glu Tyr Trp Gly
                100                 105                 110

Gln Gly Thr Ser Val Thr Val Ser Ser Ala Lys Thr Thr Pro Pro Ser
            115                 120                 125

Val Tyr Pro Leu Ala Pro Gly Ser Ala Ala Gln Thr Asn Ser Met Val
        130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Glu Ser Asp Leu Tyr Thr Leu Ser Ser Ser Val Thr Val Pro
                180                 185                 190

Ser Ser Pro Arg Pro Ser Glu Thr Val Thr Cys Asn Val Ala His Pro
            195                 200                 205

Ala Ser Ser Thr Lys Val Asp Lys Lys Ile Val Pro Arg Asp Cys Gly
        210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
                260                 265                 270

Phe Ser Trp Phe Val Asp Asp Val Glu Val His Thr Ala Gln Thr Gln
            275                 280                 285
```

Pro Arg Glu Glu Gln Phe Asn Ser Thr Phe Arg Ser Val Ser Glu Leu
        290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asn Thr Asn Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly
        435                 440

<210> SEQ ID NO 40
<211> LENGTH: 212
<212> TYPE: PRT
<213> ORGANISM: Artificial Sequence
<220> FEATURE:
<223> OTHER INFORMATION: A synthetic amino acid sequence

<400> SEQUENCE: 40

Glu Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Ala Asp Ala Ala Pro Thr
            100                 105                 110

Val Ser Ile Phe Pro Pro Ser Ser Glu Gln Leu Thr Ser Gly Gly Ala
        115                 120                 125

Ser Val Val Cys Phe Leu Asn Asn Phe Tyr Pro Lys Asp Ile Asn Val
    130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
        195                 200                 205

Arg Asn Glu Cys
    210

<210> SEQ ID NO 41
<211> LENGTH: 212
<212> TYPE: PRT
<213> ORGANISM: Artificial Sequence
<220> FEATURE:
<223> OTHER INFORMATION: A synthetic amino acid sequence

<400> SEQUENCE: 41

Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Ala Asp Ala Ala Pro Thr
            100                 105                 110

Val Ser Ile Phe Pro Pro Ser Ser Glu Gln Leu Thr Ser Gly Gly Ala
        115                 120                 125

Ser Val Val Cys Phe Leu Asn Asn Phe Tyr Pro Lys Asp Ile Asn Val
    130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
            180                 185                 190

Glu Ala Thr His Lys Thr Ser Thr Ser Pro Ile Val Lys Ser Phe Asn
        195                 200                 205

Arg Asn Glu Cys
    210

<210> SEQ ID NO 42
<211> LENGTH: 450
<212> TYPE: PRT
<213> ORGANISM: Artificial Sequence
<220> FEATURE:
<223> OTHER INFORMATION: A synthetic amino acid sequence

<400> SEQUENCE: 42

Gln Val Gln Leu Lys Arg Ala Ser Gly Pro Gly Leu Val Ala Pro Ser
1               5                   10                  15

Gln Ser Leu Ser Ile Thr Cys Thr Val Ser Gly Phe Ser Leu Thr Ile
            20                  25                  30

Tyr Gly Ala His Trp Val Arg Gln Pro Pro Gly Lys Gly Leu Glu Trp
        35                  40                  45

Leu Gly Val Ile Trp Ala Gly Gly Ser Thr Asn Tyr Asn Ser Ala Leu
    50                  55                  60

Met Ser Arg Leu Ser Ile Ser Lys Asp Asn Ser Lys Ser Gln Val Phe

```
            65                   70                   75                   80
Leu Lys Ile Asn Ser Leu Gln Thr Asp Asp Thr Ala Leu Tyr Tyr Cys
                     85                   90                   95

Ala Arg Asp Gly Ser Ser Pro Tyr Tyr Tyr Ser Met Glu Tyr Trp Gly
                100                 105                 110

Gln Gly Thr Ser Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 43
<211> LENGTH: 213
<212> TYPE: PRT
<213> ORGANISM: Artificial Sequence
```

-continued

```
<220> FEATURE:
<223> OTHER INFORMATION: A synthetic amino acid sequence

<400> SEQUENCE: 43
```

Glu Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

```
<210> SEQ ID NO 44
<211> LENGTH: 213
<212> TYPE: PRT
<213> ORGANISM: Artificial Sequence
<220> FEATURE:
<223> OTHER INFORMATION: A synthetic amino acid sequence

<400> SEQUENCE: 44
```

Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr

```
            115                 120                 125
Ala Ser Val Val Cys Leu Leu Asn Asn Phe Tyr Pro Arg Glu Ala Lys
        130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
                195                 200                 205
Asn Arg Gly Glu Cys
210

<210> SEQ ID NO 45
<211> LENGTH: 446
<212> TYPE: PRT
<213> ORGANISM: Artificial Sequence
<220> FEATURE:
<223> OTHER INFORMATION: A synthetic amino acid sequence

<400> SEQUENCE: 45

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Ser Leu Thr Ile Tyr
            20                  25                  30
Gly Ala His Trp Val Arg Gln Ala Pro Gly Lys Gly Leu Glu Trp Val
        35                  40                  45
Gly Val Ile Trp Ala Gly Gly Ser Thr Asn Tyr Asn Ser Ala Leu Met
    50                  55                  60
Ser Arg Phe Thr Ile Ser Lys Asp Asn Ser Lys Asn Thr Val Tyr Leu
65                  70                  75                  80
Gln Met Asn Ser Leu Arg Ala Glu Asp Thr Ala Val Tyr Tyr Cys Ala
                85                  90                  95
Arg Asp Gly Ser Ser Pro Tyr Tyr Tyr Ser Met Glu Tyr Trp Gly Gln
            100                 105                 110
Gly Thr Thr Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
    210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
```

```
                260                 265                 270
Val Gln Phe Asn Trp Tyr Val Asp Gly Val Glu Val His Asn Ala Lys
            275                 280                 285

Thr Lys Pro Arg Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly
                435                 440                 445

<210> SEQ ID NO 46
<211> LENGTH: 120
<212> TYPE: PRT
<213> ORGANISM: Artificial Sequence
<220> FEATURE:
<223> OTHER INFORMATION: A synthetic amino acid sequence

<400> SEQUENCE: 46

Glu Val Gln Val Val Glu Ser Gly Gly Asp Leu Val Lys Ser Gly Gly
1               5                   10                  15

Ser Leu Lys Leu Ser Cys Ala Ala Ser Gly Phe Pro Phe Ser Ser Tyr
            20                  25                  30

Ala Met Ser Trp Val Arg Gln Thr Pro Asp Lys Arg Leu Glu Trp Val
        35                  40                  45

Ala Ile Ile Ser Ser Gly Gly Ser Tyr Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Glu Thr Ala Gln Ala Ala Trp Phe Ala Tyr Trp Gly Gln
            100                 105                 110

Gly Thr Leu Val Thr Val Ser Ala
        115                 120

<210> SEQ ID NO 47
<211> LENGTH: 121
<212> TYPE: PRT
<213> ORGANISM: Artificial Sequence
<220> FEATURE:
<223> OTHER INFORMATION: A synthetic amino acid sequence

<400> SEQUENCE: 47
```

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Met Tyr Trp Val Lys Gln Arg Pro Glu Gln Gly Leu Glu Trp Ile
        35                  40                  45

Gly Arg Ile Ala Pro Glu Asp Gly Asp Thr Glu Tyr Ala Pro Lys Phe
    50                  55                  60

Gln Gly Lys Ala Thr Val Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Thr Thr Glu Gly Asn Tyr Tyr Gly Ser Ser Ile Leu Asp Tyr Trp Gly
            100                 105                 110

Gln Gly Thr Thr Leu Thr Val Ser Ser
            115                 120

<210> SEQ ID NO 48
<211> LENGTH: 118
<212> TYPE: PRT
<213> ORGANISM: Artificial Sequence
<220> FEATURE:
<223> OTHER INFORMATION: A synthetic amino acid sequence

<400> SEQUENCE: 48

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Arg Ser Ser
            20                  25                  30

Trp Met Asn Trp Val Lys Gln Arg Pro Gly Lys Gly Leu Glu Trp Ile
        35                  40                  45

Gly Gln Ile Tyr Pro Gly Asp Asp Tyr Thr Asn Tyr Asn Gly Lys Phe
    50                  55                  60

Lys Gly Lys Val Thr Leu Thr Ala Asp Arg Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Leu Gly Pro Tyr Gly Pro Phe Ala Asp Trp Gly Gln Gly Thr
            100                 105                 110

Leu Val Thr Val Ser Ala
            115

<210> SEQ ID NO 49
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 49

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Tyr Gly Val Pro Ala Arg Phe Ser Gly Ser
    50                  55                  60

```
Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gly Gly Thr Lys Leu Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: A synthetic amino acid sequence

<400> SEQUENCE: 50

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr
            20                  25                  30

Leu Asn Trp Tyr Gln Gln Lys Pro Asp Gly Thr Val Lys Leu Leu Ile
        35                  40                  45

Tyr Phe Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 51
<211> LENGTH: 106
<212> TYPE: PRT
<213> ORGANISM: Artificial Sequence
<220> FEATURE:
<223> OTHER INFORMATION: A synthetic amino acid sequence

<400> SEQUENCE: 51

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Arg Pro Gly Ser Ser Pro Arg Leu Leu Ile Tyr
        35                  40                  45

Asp Thr Ser Ser Leu Ala Ser Gly Val Pro Val Arg Phe Ser Gly Ser
    50                  55                  60

Gly Ser Gly Thr Ser Tyr Ser Leu Thr Ile Ser Arg Ile Glu Ser Glu
65                  70                  75                  80

Asp Ala Ala Asn Tyr Tyr Cys Gln Gln Trp Asn Ser Asp Pro Tyr Thr
                85                  90                  95

Phe Gly Gly Gly Thr Lys Leu Glu Ile Lys
            100                 105

<210> SEQ ID NO 52
<211> LENGTH: 141
<212> TYPE: PRT
<213> ORGANISM: Artificial Sequence
<220> FEATURE:
<223> OTHER INFORMATION: A synthetic amino acid sequence
```

<400> SEQUENCE: 52

```
Met Glu Gly Asp Arg Gln Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Gln Asp Gly Trp Thr Asp Ser Asp Pro Val His Gly
        35                  40                  45

Tyr Trp Phe Arg Ala Gly Asp Arg Pro Tyr Gln Asp Ala Pro Val Ala
    50                  55                  60

Thr Asn Asn Pro Asp Arg Glu Val Gln Ala Glu Thr Gln Gly Arg Phe
65                  70                  75                  80

Gln Leu Leu Gly Asp Ile Trp Ser Asn Asp Cys Ser Leu Ser Ile Arg
                85                  90                  95

Asp Ala Arg Lys Arg Asp Lys Gly Ser Tyr Phe Phe Arg Leu Glu Arg
                100                 105                 110

Gly Ser Met Lys Trp Ser Tyr Lys Ser Gln Leu Asn Tyr Lys Thr Lys
            115                 120                 125

Gln Leu Ser Val Phe Val Thr Ala Leu Thr His Arg Pro
        130                 135                 140
```

<210> SEQ ID NO 53
<211> LENGTH: 87
<212> TYPE: PRT
<213> ORGANISM: Artificial Sequence
<220> FEATURE:
<223> OTHER INFORMATION: A synthetic amino acid sequence

<400> SEQUENCE: 53

```
Asp Ile Leu Ile Leu Gly Thr Leu Glu Ser Gly His Ser Arg Asn Leu
1               5                   10                  15

Thr Cys Ser Val Pro Trp Ala Cys Lys Gln Gly Thr Pro Pro Met Ile
            20                  25                  30

Ser Trp Ile Gly Ala Ser Val Ser Ser Pro Gly Pro Thr Thr Ala Arg
        35                  40                  45

Ser Ser Val Leu Thr Leu Thr Pro Lys Pro Gln Asp His Gly Thr Ser
    50                  55                  60

Leu Thr Cys Gln Val Thr Leu Pro Gly Thr Gly Val Thr Thr Thr Ser
65                  70                  75                  80

Thr Val Arg Leu Asp Val Ser
                85
```

<210> SEQ ID NO 54
<211> LENGTH: 122
<212> TYPE: PRT
<213> ORGANISM: Artificial Sequence
<220> FEATURE:
<223> OTHER INFORMATION: A synthetic amino acid sequence

<400> SEQUENCE: 54

```
Tyr Pro Pro Trp Asn Leu Thr Met Thr Val Phe Gln Gly Asp Ala Thr
1               5                   10                  15

Ala Ser Thr Ala Leu Gly Asn Gly Ser Ser Leu Ser Val Leu Glu Gly
            20                  25                  30

Gln Ser Leu Arg Leu Val Cys Ala Val Asn Ser Asn Pro Pro Ala Arg
        35                  40                  45

Leu Ser Trp Thr Arg Gly Ser Leu Thr Leu Cys Pro Ser Arg Ser Ser
    50                  55                  60
```

```
Asn Pro Gly Leu Leu Glu Leu Pro Arg Val His Val Arg Asp Glu Gly
 65                  70                  75                  80

Glu Phe Thr Cys Arg Ala Gln Asn Ala Gln Gly Ser Gln His Ile Ser
                 85                  90                  95

Leu Ser Leu Ser Leu Gln Asn Glu Gly Thr Gly Thr Ser Arg Pro Val
            100                 105                 110

Ser Gln Val Thr Leu Ala Ala Val Gly Gly
        115                 120

<210> SEQ ID NO 55
<211> LENGTH: 373
<212> TYPE: PRT
<213> ORGANISM: Artificial Sequence
<220> FEATURE:
<223> OTHER INFORMATION: A synthetic amino acid sequence

<400> SEQUENCE: 55

Met Glu Gly Asp Arg Gln Tyr Gly Asp Gly Tyr Leu Leu Gln Val Gln
  1               5                  10                  15

Glu Leu Val Thr Val Gln Glu Gly Leu Cys Val His Val Pro Cys Ser
             20                  25                  30

Phe Ser Tyr Pro Gln Asp Gly Trp Thr Asp Ser Asp Pro Val His Gly
         35                  40                  45

Tyr Trp Phe Arg Ala Gly Asp Arg Pro Tyr Gln Asp Ala Pro Val Ala
     50                  55                  60

Thr Asn Asn Pro Asp Arg Glu Val Gln Ala Glu Thr Gln Gly Arg Phe
 65                  70                  75                  80

Gln Leu Leu Gly Asp Ile Trp Ser Asn Asp Cys Ser Leu Ser Ile Arg
                 85                  90                  95

Asp Ala Arg Lys Arg Asp Lys Gly Ser Tyr Phe Phe Arg Leu Glu Arg
            100                 105                 110

Gly Ser Met Lys Trp Ser Tyr Lys Ser Gln Leu Asn Tyr Lys Thr Lys
        115                 120                 125

Gln Leu Ser Val Phe Val Thr Ala Leu Thr His Arg Pro Ile Glu Gly
    130                 135                 140

Arg Ser Asp Lys Thr His Thr Cys Pro Pro Cys Pro Ala Pro Glu Leu
145                 150                 155                 160

Leu Gly Gly Pro Ser Val Phe Leu Phe Pro Pro Lys Pro Lys Asp Thr
                165                 170                 175

Leu Met Ile Ser Arg Thr Pro Glu Val Thr Cys Val Val Val Asp Val
            180                 185                 190

Ser His Glu Asp Pro Glu Val Lys Phe Asn Trp Tyr Val Asp Gly Val
        195                 200                 205

Glu Val His Asn Ala Lys Thr Lys Pro Arg Glu Glu Gln Tyr Asn Ser
    210                 215                 220

Thr Tyr Arg Val Val Ser Val Leu Thr Val Leu His Gln Asp Trp Leu
225                 230                 235                 240

Asn Gly Lys Glu Tyr Lys Cys Lys Val Ser Asn Lys Ala Leu Pro Ala
                245                 250                 255

Pro Ile Glu Lys Thr Ile Ser Lys Ala Lys Gly Gln Pro Arg Glu Pro
            260                 265                 270

Gln Val Tyr Thr Leu Pro Pro Ser Arg Glu Glu Met Thr Lys Asn Gln
        275                 280                 285

Val Ser Leu Thr Cys Leu Val Lys Gly Phe Tyr Pro Ser Asp Ile Ala
    290                 295                 300
```

Val Glu Trp Glu Ser Asn Gly Gln Pro Glu Asn Asn Tyr Lys Thr Thr
305                 310                 315                 320

Pro Pro Val Leu Asp Ser Asp Gly Ser Phe Phe Leu Tyr Ser Lys Leu
                325                 330                 335

Thr Val Asp Lys Ser Arg Trp Gln Gln Gly Asn Val Phe Ser Cys Ser
                340                 345                 350

Val Met His Glu Ala Leu His Asn His Tyr Thr Gln Lys Ser Leu Ser
            355                 360                 365

Leu Ser Pro Gly Lys
        370

<210> SEQ ID NO 56
<211> LENGTH: 460
<212> TYPE: PRT
<213> ORGANISM: Artificial Sequence
<220> FEATURE:
<223> OTHER INFORMATION: A synthetic amino acid sequence

<400> SEQUENCE: 56

Met Glu Gly Asp Arg Gln Tyr Gly Asp Gly Tyr Leu Leu Gln Val Gln
1               5                   10                  15

Glu Leu Val Thr Val Gln Glu Gly Leu Cys Val His Val Pro Cys Ser
                20                  25                  30

Phe Ser Tyr Pro Gln Asp Gly Trp Thr Asp Ser Asp Pro Val His Gly
            35                  40                  45

Tyr Trp Phe Arg Ala Gly Asp Arg Pro Tyr Gln Asp Ala Pro Val Ala
        50                  55                  60

Thr Asn Asn Pro Asp Arg Glu Val Gln Ala Glu Thr Gln Gly Arg Phe
65                  70                  75                  80

Gln Leu Leu Gly Asp Ile Trp Ser Asn Asp Cys Ser Leu Ser Ile Arg
                85                  90                  95

Asp Ala Arg Lys Arg Asp Lys Gly Ser Tyr Phe Phe Arg Leu Glu Arg
                100                 105                 110

Gly Ser Met Lys Trp Ser Tyr Lys Ser Gln Leu Asn Tyr Lys Thr Lys
            115                 120                 125

Gln Leu Ser Val Phe Val Thr Ala Leu Thr His Arg Pro Asp Ile Leu
        130                 135                 140

Ile Leu Gly Thr Leu Glu Ser Gly His Ser Arg Asn Leu Thr Cys Ser
145                 150                 155                 160

Val Pro Trp Ala Cys Lys Gln Gly Thr Pro Pro Met Ile Ser Trp Ile
                165                 170                 175

Gly Ala Ser Val Ser Ser Pro Gly Pro Thr Thr Ala Arg Ser Ser Val
            180                 185                 190

Leu Thr Leu Thr Pro Lys Pro Gln Asp His Gly Thr Ser Leu Thr Cys
        195                 200                 205

Gln Val Thr Leu Pro Gly Thr Gly Val Thr Thr Thr Ser Thr Val Arg
        210                 215                 220

Leu Asp Val Ser Ile Glu Gly Arg Ser Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
                260                 265                 270

Thr Cys Val Val Val Asp Val Ser His Glu Asp Pro Glu Val Lys Phe
            275                 280                 285

```
Asn Trp Tyr Val Asp Gly Val Glu Val His Asn Ala Lys Thr Lys Pro
        290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
            325                 330                 335

Ser Asn Lys Ala Leu Pro Ala Pro Ile Glu Lys Thr Ile Ser Lys Ala
        340                 345                 350

Lys Gly Gln Pro Arg Glu Pro Gln Val Tyr Thr Leu Pro Pro Ser Arg
            355                 360                 365

Glu Glu Met Thr Lys Asn Gln Val Ser Leu Thr Cys Leu Val Lys Gly
        370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
            405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
    450                 455                 460

<210> SEQ ID NO 57
<211> LENGTH: 582
<212> TYPE: PRT
<213> ORGANISM: Artificial Sequence
<220> FEATURE:
<223> OTHER INFORMATION: A synthetic amino acid sequence

<400> SEQUENCE: 57

Met Glu Gly Asp Arg Gln Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Gln Asp Gly Trp Thr Asp Ser Asp Pro Val His Gly
        35                  40                  45

Tyr Trp Phe Arg Ala Gly Asp Arg Pro Tyr Gln Asp Ala Pro Val Ala
    50                  55                  60

Thr Asn Asn Pro Asp Arg Glu Val Gln Ala Glu Thr Gln Gly Arg Phe
65                  70                  75                  80

Gln Leu Leu Gly Asp Ile Trp Ser Asn Asp Cys Ser Leu Ser Ile Arg
            85                  90                  95

Asp Ala Arg Lys Arg Asp Lys Gly Ser Tyr Phe Phe Arg Leu Glu Arg
            100                 105                 110

Gly Ser Met Lys Trp Ser Tyr Lys Ser Gln Leu Asn Tyr Lys Thr Lys
        115                 120                 125

Gln Leu Ser Val Phe Val Thr Ala Leu Thr His Arg Pro Asp Ile Leu
130                 135                 140

Ile Leu Gly Thr Leu Glu Ser Gly His Ser Arg Asn Leu Thr Cys Ser
145                 150                 155                 160

Val Pro Trp Ala Cys Lys Gln Gly Thr Pro Pro Met Ile Ser Trp Ile
            165                 170                 175

Gly Ala Ser Val Ser Ser Pro Gly Pro Thr Thr Ala Arg Ser Ser Val
            180                 185                 190
```

```
Leu Thr Leu Thr Pro Lys Pro Gln Asp His Gly Thr Ser Leu Thr Cys
            195                 200                 205

Gln Val Thr Leu Pro Gly Thr Gly Val Thr Thr Ser Thr Val Arg
    210                 215                 220

Leu Asp Val Ser Tyr Pro Pro Trp Asn Leu Thr Met Thr Val Phe Gln
225                 230                 235                 240

Gly Asp Ala Thr Ala Ser Thr Ala Leu Gly Asn Gly Ser Ser Leu Ser
                245                 250                 255

Val Leu Glu Gly Gln Ser Leu Arg Leu Val Cys Ala Val Asn Ser Asn
                260                 265                 270

Pro Pro Ala Arg Leu Ser Trp Thr Arg Gly Ser Leu Thr Leu Cys Pro
            275                 280                 285

Ser Arg Ser Ser Asn Pro Gly Leu Leu Glu Leu Pro Arg Val His Val
        290                 295                 300

Arg Asp Glu Gly Glu Phe Thr Cys Arg Ala Gln Asn Ala Gln Gly Ser
305                 310                 315                 320

Gln His Ile Ser Leu Ser Leu Ser Leu Gln Asn Glu Gly Thr Gly Thr
                325                 330                 335

Ser Arg Pro Val Ser Gln Val Thr Leu Ala Ala Val Gly Gly Ile Glu
            340                 345                 350

Gly Arg Ser Asp Lys Thr His Thr Cys Pro Pro Cys Pro Ala Pro Glu
        355                 360                 365

Leu Leu Gly Gly Pro Ser Val Phe Leu Phe Pro Pro Lys Pro Lys Asp
    370                 375                 380

Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
                405                 410                 415

Val Glu Val His Asn Ala Lys Thr Lys Pro Arg Glu Glu Gln Tyr Asn
                420                 425                 430

Ser Thr Tyr Arg Val Val Ser Val Leu Thr Val Leu His Gln Asp Trp
            435                 440                 445

Leu Asn Gly Lys Glu Tyr Lys Cys Lys Val Ser Asn Lys Ala Leu Pro
    450                 455                 460

Ala Pro Ile Glu Lys Thr Ile Ser Lys Ala Lys Gly Gln Pro Arg Glu
465                 470                 475                 480

Pro Gln Val Tyr Thr Leu Pro Pro Ser Arg Asp Glu Leu Thr Lys Asn
                485                 490                 495

Gln Val Ser Leu Thr Cys Leu Val Lys Gly Phe Tyr Pro Ser Asp Ile
            500                 505                 510

Ala Val Glu Trp Glu Ser Asn Gly Gln Pro Glu Asn Asn Tyr Lys Thr
    515                 520                 525

Thr Pro Pro Val Leu Asp Ser Asp Gly Ser Phe Phe Leu Tyr Ser Lys
530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
                565                 570                 575

Ser Leu Ser Pro Gly Lys
            580

<210> SEQ ID NO 58
<211> LENGTH: 582
```

```
<212> TYPE: PRT
<213> ORGANISM: Artificial Sequence
<220> FEATURE:
<223> OTHER INFORMATION: A synthetic amino acid sequence

<400> SEQUENCE: 58

Met Glu Gly Asp Arg Lys Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Lys Asp Asp Trp Thr Tyr Ser Asp Pro Val His Gly
        35                  40                  45

Tyr Trp Phe Arg Ala Gly Asp Arg Pro Tyr Gln Glu Ala Pro Val Ala
    50                  55                  60

Thr Asn Asn Pro Asp Thr Glu Val Gln Ala Glu Thr Gln Gly Arg Phe
65                  70                  75                  80

Gln Leu Leu Gly Asp Arg Trp Ser Asn Asp Cys Ser Leu Ser Ile Asn
                85                  90                  95

Asp Ala Arg Lys Gly Asp Glu Gly Ser Tyr Phe Phe Arg Leu Glu Arg
            100                 105                 110

Gly Arg Met Lys Trp Ser Tyr Lys Ser Gln Leu Asn Tyr Lys Ala Lys
        115                 120                 125

Gln Leu Ser Val Phe Val Thr Ala Leu Thr Gln Arg Pro Asp Ile Leu
    130                 135                 140

Ile Gln Gly Thr Leu Glu Ser Gly His Pro Arg Asn Leu Thr Cys Ser
145                 150                 155                 160

Val Pro Trp Ala Cys Glu Gln Arg Met Pro Pro Met Ile Ser Trp Ile
                165                 170                 175

Gly Thr Ser Val Ser Ser Leu Gly Pro Ile Thr Ala Arg Phe Ser Val
            180                 185                 190

Leu Thr Leu Ile Pro Lys Pro Gln Asp His Gly Thr Ser Leu Thr Cys
        195                 200                 205

Gln Val Thr Leu Pro Gly Thr Gly Val Thr Thr Thr Arg Thr Val Gln
    210                 215                 220

Leu Asp Val Ser Tyr Pro Pro Trp Asn Leu Thr Val Thr Val Phe Gln
225                 230                 235                 240

Gly Asp Asp Thr Ala Ser Thr Ala Leu Gly Asn Gly Ser Ser Leu Ser
                245                 250                 255

Val Leu Glu Gly Gln Ser Leu Arg Leu Val Cys Ala Val Asp Ser Asn
            260                 265                 270

Pro Pro Ala Arg Leu Ser Trp Thr Arg Gly Ser Leu Thr Leu Cys Pro
        275                 280                 285

Ser Gln Pro Trp Asn Pro Gly Leu Leu Glu Leu Leu Arg Val His Val
    290                 295                 300

Lys Asp Glu Gly Glu Phe Thr Cys Gln Ala Glu Asn Pro Arg Gly Ser
305                 310                 315                 320

Gln His Ile Ser Leu Ser Leu Ser Leu Gln Asn Glu Gly Thr Gly Thr
                325                 330                 335

Ala Arg Pro Val Ser Glu Val Thr Leu Ala Ala Val Gly Gly Ile Glu
            340                 345                 350

Gly Arg Ser Asp Lys Thr His Thr Cys Pro Cys Pro Ala Pro Glu
        355                 360                 365

Leu Leu Gly Gly Pro Ser Val Phe Leu Phe Pro Pro Lys Pro Lys Asp
    370                 375                 380
```

```
Thr Leu Met Ile Ser Arg Thr Pro Glu Val Thr Cys Val Val Val Asp
385                 390                 395                 400

Val Ser His Glu Asp Pro Glu Val Lys Phe Asn Trp Tyr Val Asp Gly
            405                 410                 415

Val Glu Val His Asn Ala Lys Thr Lys Pro Arg Glu Glu Gln Tyr Asn
        420                 425                 430

Ser Thr Tyr Arg Val Val Ser Val Leu Thr Val Leu His Gln Asp Trp
        435                 440                 445

Leu Asn Gly Lys Glu Tyr Lys Cys Lys Val Ser Asn Lys Ala Leu Pro
    450                 455                 460

Ala Pro Ile Glu Lys Thr Ile Ser Lys Ala Lys Gly Gln Pro Arg Glu
465                 470                 475                 480

Pro Gln Val Tyr Thr Leu Pro Pro Ser Arg Glu Glu Met Thr Lys Asn
            485                 490                 495

Gln Val Ser Leu Thr Cys Leu Val Lys Gly Phe Tyr Pro Ser Asp Ile
        500                 505                 510

Ala Val Glu Trp Glu Ser Asn Gly Gln Pro Glu Asn Asn Tyr Lys Thr
        515                 520                 525

Thr Pro Pro Val Leu Asp Ser Asp Gly Ser Phe Phe Leu Tyr Ser Lys
530                 535                 540

Leu Thr Val Asp Lys Ser Arg Trp Gln Gln Gly Asn Val Phe Ser Cys
545                 550                 555                 560

Ser Val Met His Glu Ala Leu His Asn His Tyr Thr Gln Lys Ser Leu
            565                 570                 575

Ser Leu Ser Pro Gly Lys
            580

<210> SEQ ID NO 59
<211> LENGTH: 350
<212> TYPE: PRT
<213> ORGANISM: Artificial Sequence
<220> FEATURE:
<223> OTHER INFORMATION: A synthetic amino acid sequence

<400> SEQUENCE: 59

Met Glu Gly Asp Arg Lys Tyr Gly Asp Gly Tyr Leu Leu Gln Val Gln
1               5                   10                  15

Glu Leu Val Thr Val Gln Glu Gly Leu Cys Val His Val Pro Cys Ser
            20                  25                  30

Phe Ser Tyr Pro Lys Asp Asp Trp Thr Tyr Ser Asp Pro Val His Gly
        35                  40                  45

Tyr Trp Phe Arg Ala Gly Asp Arg Pro Tyr Gln Glu Ala Pro Val Ala
    50                  55                  60

Thr Asn Asn Pro Asp Thr Glu Val Gln Ala Glu Thr Gln Gly Arg Phe
65                  70                  75                  80

Gln Leu Leu Gly Asp Arg Trp Ser Asn Asp Cys Ser Leu Ser Ile Asn
                85                  90                  95

Asp Ala Arg Lys Gly Asp Glu Gly Ser Tyr Phe Phe Arg Leu Glu Arg
            100                 105                 110

Gly Arg Met Lys Trp Ser Tyr Lys Ser Gln Leu Asn Tyr Lys Ala Lys
        115                 120                 125

Gln Leu Ser Val Phe Val Thr Ala Leu Thr Gln Arg Pro Asp Ile Leu
    130                 135                 140

Ile Gln Gly Thr Leu Glu Ser Gly His Pro Arg Asn Leu Thr Cys Ser
145                 150                 155                 160
```

```
Val Pro Trp Ala Cys Glu Gln Arg Met Pro Pro Met Ile Ser Trp Ile
                165                 170                 175

Gly Thr Ser Val Ser Ser Leu Gly Pro Ile Thr Ala Arg Phe Ser Val
            180                 185                 190

Leu Thr Leu Ile Pro Lys Pro Gln Asp His Gly Thr Ser Leu Thr Cys
            195                 200                 205

Gln Val Thr Leu Pro Gly Thr Gly Val Thr Thr Arg Thr Val Gln
        210                 215                 220

Leu Asp Val Ser Tyr Pro Pro Trp Asn Leu Thr Val Thr Val Phe Gln
225                 230                 235                 240

Gly Asp Asp Thr Ala Ser Thr Ala Leu Gly Asn Gly Ser Ser Leu Ser
                245                 250                 255

Val Leu Glu Gly Gln Ser Leu Arg Leu Val Cys Ala Val Asp Ser Asn
                260                 265                 270

Pro Pro Ala Arg Leu Ser Trp Thr Arg Gly Ser Leu Thr Leu Cys Pro
            275                 280                 285

Ser Gln Pro Trp Asn Pro Gly Leu Leu Glu Leu Leu Arg Val His Val
            290                 295                 300

Lys Asp Glu Gly Glu Phe Thr Cys Gln Ala Glu Asn Pro Arg Gly Ser
305                 310                 315                 320

Gln His Ile Ser Leu Ser Leu Ser Leu Gln Asn Glu Gly Thr Gly Thr
                325                 330                 335

Ala Arg Pro Val Ser Glu Val Thr Leu Ala Ala Val Gly Gly
                340                 345                 350

<210> SEQ ID NO 60
<211> LENGTH: 22
<212> TYPE: PRT
<213> ORGANISM: Artificial Sequence
<220> FEATURE:
<223> OTHER INFORMATION: A synthetic amino acid sequence

<400> SEQUENCE: 60

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 61
<211> LENGTH: 19
<212> TYPE: PRT
<213> ORGANISM: Artificial Sequence
<220> FEATURE:
<223> OTHER INFORMATION: A synthetic amino acid sequence

<400> SEQUENCE: 61

Met Glu Phe Gly Leu Ser Trp Leu Phe Leu Val Ala Ile Leu Lys Gly
1               5                   10                  15

Val Gln Cys
```

GENE THERAPY FOR EOSINOPHILIC DISORDERS

CROSS-REFERENCE TO RELATED APPLICATIONS

This application is a U.S. national stage filing under 35 U.S.C. § 371 from International Application No. PCT/US2018/067869, filed on 28 Dec. 2018, and published as WO2019/133818 on 4 Jul. 2019, which claims the benefit of the filing date of U.S. application No. 62/612,005, filed on Dec. 29, 2017, the disclosures of which are incorporated by reference herein.

BACKGROUND

Eosinophils are highly specialized bone marrow-derived granulocytic cells that play a role in combating parasites and other pathogens (Young et al., 2006). In normal individuals, eosinophils represent <5% of white blood cells, with an absolute count of 300-500/Ml (Young et al., 2006; Bridgen et al., 1997; Gotlieb et al., 2015; Rothenberg et al., 2006). Eosinophils normally persist in the circulation 8-12 hr. survive in tissues 8-12 days (Young et al., 2006), and carry a variety of cytotoxic mediators in cytoplasmic granules, including major basic protein, cationic protein, peroxidase and neurotoxin, and can release reactive oxygen species, lipid mediators, destructive enzymes and a variety of cytokines (Rothenberg et al., 2006; Bandiera-Melo et al., 2002; Hogan et al., 2008; Horuichi et al., 1997; Kato et al., 2005; Lacy, 2005; Park et al., 2010; Salto et al., 2004; Song et al., 2009; Song et al., 2009; Trulson et al., 2007). If eosinophils invade tissues in sufficient numbers, they are capable of causing significant organ damage and dysfunction (Rothenberg et al., 2006; Bandiera-Melo et al., 2002; Hogan et al., 2008; Horuichi et al., 1997; Kato et al., 2005; Lacy, 2005; Saito et al., 2004; Song et al., 2009; Song et al., 2009; Trulson et al., 2007; Zimmermann et al., 2008; Bolus et al., 2015; Gleich et al., 1986; Morgan et al., 2005; Slifman et al., 1986; Venge et al., 1999; Zheutlin et al., 1984). There are a variety of primary and secondary hypereosinophilic disorders characterized by chronic elevation of blood eosinophil levels, invasion of organs with eosinophils, and associated organ damage (Curtis et al., 2016; Falchi et al., 2015; Gotlib et al., 2012; Helbing et al., 2012; Reiter et al. 2017; Roufosse et al., 2012; Tefferi et al, 2006; Valent et al., 2012).

SUMMERY

The present disclosure relates to in vivo gene therapy to treat eosinophilic disorders, e.g., cancers such as leukemias including but not limited to chronic eosinophilic leukemia-not otherwise specified (CEL-NOS), a fatal malignant disorder representing an unmet medical need with no effective therapy. CEL-NOS, a subtype adult chronic eosinophilic leukemia with persistent elevation of blood eosinophils >1.5×10$^3$/μL of unknown cause, is characterized by dysfunction of organs infiltrated with eosinophils. CEL-NOS is unresponsive to any therapy. Since the pathogenesis is unknown, the most direct therapy for CEL-NOS is to suppress the number of eosinophils in blood, thus suppressing eosinophil tissue invasion and organ dysfunction. In one embodiment, a gene therapy for eosinophilic disorders such as CEL-NOS is provided that employs an adeno-associated virus (AAV) vector coding for an anti-eosinophil monoclonal. In one embodiment the AAV is AAVrh.10mAnti-Eos (LEXm03), a serotype rh.10 AAV vector administered intravenously to genetically modify cells such as liver hepatocytes to express and secrete in one embodiment, a murine-specific anti-eosinophil monoclonal that induces murine eosinophil apoptosis. To evaluate the effectiveness of LEXm03, a CEL-NOS mouse model was prepared using another AAV vector (AAVrh.10mIL5) administered intravenously to genetically modify the liver to persistently secrete high levels of murine interleukin-5 (IL5), which in turn, stimulates bone marrow to persistently generate high blood levels of eosinophils (>100,000 eosinophils/μL), with tissue eosinophil infiltration and eventually death. The data demonstrates that LEXm03 induces apoptosis of eosinophils in vitro and in vivo, and markedly lowers the blood eosinophil levels in the CEL-NOS mouse model. While CEL-NOS is uncommon, there are many hyper eosinophilic disorders for which the LEXm03 strategy is explicable as disclosed herein. Moreover, the strategy may be employed with other anti-eosinophil monoclonals that induce eosinophil apoptosis. Using intravenous administration of vectors such as LEXm03 to genetically modify cells such as hepatocytes to secrete the anti-eosinophil monoclonal antibody allows for significant suppression of blood eosinophil levels, with decreased tissue invasion of eosinophils and reduced morbidity and mortality.

In one embodiment, the disclosure provides a method of preventing, inhibiting or treating a hypereosinophilic disease or disorder in a mammal. The method includes administering to the mammal a composition comprising an expression vector encoding an antibody that binds eosinophils or binds a molecule that increases the number of eosinophils or enhances the rate of maturation thereof, in an amount effective to prevent, inhibit or treat one or more symptoms of the hypereosinophilic disorder in the mammal. In one embodiment, the mammal is a human. In one embodiment, the disease is cancer. In one embodiment, the expression vector is a plasmid. In one embodiment, the expression vector is part d a virus, e.g., an adenovirus, lentivirus, retrovirus or adeno-associated virus. In one embodiment, the composition comprises an adeno-associated virus comprising the expression vector. In one embodiment the AAV is AAV1, AAV2, AAV3, AAV4, AAV5, AAV6, AAV7 AAV8, AAV9 or AAVrh10. In one embodiment the antibody is a chimeric, scFv, humanized or fully human antibody. In one embodiment, the expression vector encodes an antibody with a sequence having at least 80% amino acid sequence identity to a polypeptide encoded by SEQ ID NO:1 or Z or a sequence having at least 80% amino acid sequence identity to any one to SEQ ID Nos. 3-6, 8-32, 40-41, 43-44, or 46-51, or any combination of sequences in the variable region or CDRs of SEQ ID Nos. 3-6, 8-32, 40-41, 43-44, or 46-51. In one embodiment, the expression vector encodes an antibody with a sequence having at least 80% amino acid sequence identity to a polypeptide encoded by SEQ ID NO:1, or to a polypeptide having any one of SEQ ID Nos. 9-22, 33, 36-37, 39, 42, or 45-48, and has an IgG constant region. In one embodiment the expression vector encodes an antibody with a sequence having at least 80% amino acid sequence identity to a polypeptide encoded by SEQ ID NO:2, or to a polypeptide having any one of SEQ ID Nos. 22-32, 34-35, 38, 40-41, 43-44, or 49-51, and has a lambda light chain constant region. In one embodiment the expression vector encodes an antibody with a sequence having at least 80% amino acid sequence identity to a polypeptide encoded by SEQ ID NO:2, or to a polypeptide having any one of SEQ ID Nos. 22-32, 34-35, 38, 40-41, 43-44, or 49-51, and has a kappa light chain constant region, in one embodiment, the expression vector encodes an antibody with a sequence having at least 80% amino acid sequence identity to a polypeptide comprising SEQ ID NO:5, 6, or 8, or any combination of SEQ ID NO:5, 6, or 8. In one embodiment, the expression vector encodes an antibody with a sequence having at least 80% amino acid sequence identity to a polypeptide encoded by SEQ ID NO:5, 6, or 8, and has an IgG constant region. In one embodiment, the expression vector encodes an antibody with a sequence having at least 80% amino acid sequence identity to a polypeptide encoded by SEQ ID NO:5, 6 or 8, and has a lambda tight chain constant region. In one embodiment, the expression vector encodes an antibody with a sequence having at least 80% amino acid sequence identity to a polypeptide encoded by SEQ ID NO:5, 6, or 8, and has a kappa light chain constant region, in one embodiment, the composition is systemically administered. In one embodiment the polypeptide has 1, 2, 3, 4 or 5 substitutions, e.g., conservative or non-conservative substitutions, or a combination thereof, in a framework sequence, one or more CDRs, or both, in one of SEQ ID Nos. 3-6, 8-32, 40-41, 43-44, or 46-51.

In one embodiment, a method of inhibiting or Seating a hypereosinophilic disease or disorder, e.g., inhibiting or treating one or more symptoms of a hypereosinophilic disease or disorder, in a mammal is provided. The method includes administering to the mammal a composition comprising a viral egression vector comprising an open reading frame encoding an antibody that binds to a ligand on eosinophils or that binds a molecule, the presence of which in the mammal, increases the number of eosinophils, in an amount effective to inhibit or treat the hypereosinophilic disease or disorder in the mammal. In one embodiment, the mammal is a human. In one embodiment, the disease is cancer, asthma, esophagitis, tropic pulmonary eosinophilia, an infectious disease, an allegoric or atopic disease, gasteroenteritis, a hepatobiliary disease, meningitis, a cardiac disorder, a genitourinary disorder, an immunodeficiency, an endocrinological disorder, a pulmonary disorder, a skin disease, rheumatoid arthritis, or vasculitis. In one embodiment, the cancer is leukemia. In one embodiment, the amount administered, e.g., a single dose, reduces the number of but does not eliminate eosinophils in the mammal. In one embodiment, the amount administered reduces the number of eosinophils in one or more tissues with hypereosinophilia. In one embodiment, the amount is effective to decrease the percent of eosinophils in the mammal by at least 0.01%, 0.05%, 0.1%, 0.5%, 1%, 5%, 10%, 30%, 50%, 60%, 70%, 80% or up to 90%. In one embodiment, the viral expression vector is an adeno-associated virus vector or an adenovirus vector. In one embodiment, the AAV is AAV1, AAV2, AAV3, AAV4. AAV5, AAV6, AAV7, AAV8. AAV9 or AAVrh10. In one embodiment, the antibody is a chimeric, scFv, single heavy chain, humanized or fully human antibody. In one embodiment, the antibody binds a ligand on eosinophils, e.g., a ligand comprising a carbohydrate. In one embodiment, the ligand is a member of the sialoadhesion family, e.g., sialic acid binding Ig-like lectin 8. In one embodiment, the viral expression vector encodes an antibody comprising a polypeptide comprising a sequence having at least 80% amino acid sequence identity to a polypeptide encoded by SEQ ID NO:1 or 2, or a polypeptide comprising a sequence having at least 80% amino acid sequence identity to SEQ ID Nos. 3-6, 8-32, 40-41, 43-44, or 46-51, or a combination thereof. In one embodiment, the viral expression vector encodes an antibody with an IgG constant region. In one embodiment the viral expression vector encodes an antibody comprising a polypeptide comprising a lambda light chain constant region. In one embodiment the expression vector 0.10 encodes an antibody comprising a polypeptide comprising a kappa light chain constant region. In one embodiment, the composition is systemically administered. In one embodiment the composition is intravenously administered. In one embodiment, the composition Is administered to the central nervous system or intracranially. In one embodiment the antibody is expressed from an endogenous viral promoter. In one embodiment the endogenous promoter is modified to be inducible. In one embodiment the antibody is expressed from an exogenous promoter in the viral egression vector that is operably linked to the open reading frame. In one embodiment, the antibody is expressed from an exogenous promoter. In one embodiment the exogenous promoter is inducible. In one embodiment, the promoter is inducible with tetracycline, doxycycline, minocycline (see, e.g., tetracycline-inducible promoters in Rodriguez-Garcia et al., Nucl. Acids Res. 33:e87 (2005)), vincristine, rilamipicin, doxyrubitin, or 5-aza cytidine, e.g., a Mcir-1 promoter, fusion proteins having a ligand binding domain and an DMA binding domain specific for a promoter sequence or sequences upstream from the promoter, valproic acid, morphine (e.g., a tyrosine hydroxylase promoter), or quinolone (e.g., an osteopontin promoter). In one embodiment, the viral expression vector further comprises a suicide gene. In one embodiment, expression from the vector is decreased or eliminated using a gene encoding herpes simplex virus-thymidine kinase (HSV-tk) and administration of ganciclovir, a gene encoding cytosine deaminase optionally in combination with uracil phosphoribosyltransferase and administration of 5-fluorocytosine, a gene encoding nitroreductase and administration of 5-(azardin-1-yl)-2,4-dinitrobenzamide. Other systems include Varicella-Zoster virus thymidine kinase (VZV-tk), urine nucleoside phosphorylase (PNP), carboxypeptidase A, carboxypeptidase G2, linamarase, beta-balatosidase, or hepatic cytochrome P450-2B1.

Also provided is an isolated recombinant virus comprising an expression vector encoding an antibody directed against eosinophils. In one embodiment, the antibody has a sequence having at least 80% amino acid sequence identity to a polypeptide encoded by SEQ ID NO:1 or 2, or both, or has at least 80% amino acid sequence identity to a polypeptide comprising at least one of SEQ ID Nos. 3-6, 8-32, 40-41, 43-44 or 46-51, or a combination thereof, or a pharmaceutical comprising an effective amount of the recombinant virus. In one embodiment, the virus a recombinant adeno-associated virus (AAV). In one embodiment, the amount of AAV in the composition, or in a series of doses that is administered, is about $1\times10^{10}$ to $1\times10^{20}$ genome copies, e.g., about $1\times10^{12}$ to $1\times10^{15}$, about $1\times10^{14}$ to $1\times10^{16}$, about $1\times10^{16}$ to $1\times10^{18}$ or about $1\times10^{15}$ to $1\times10^{19}$ genome copies.

In one embodiment, exemplary targets for antibodies useful m the compositions and methods include but are not limited to IL-2, IL-3, IL-4, IL-5, IL-10, IL-12, GM-CSF, IL-13, IL-16, IL-25, IL-27, IL-28, VEGF, angiopoietin-1, PDGF, FGF, TGF-β1, TGF-β2, IFN-α, IFN-γ, RANTES (CCL5), MCP-3 (CCL7), MCP-4 (CCL13), eotaxin (CCL11), eotaxin-2 (CCL24), eotaxin-3 (CCL26), SDF-1 (CXCL12), PAF, complement factor C3a or C5a, VIP, sialoadhesion factor, or GC, or a receptor therefore including but not limited to sialoadhesion factor receptors such as Siglec 8, Toll-like R receptor, or CD33. In one embodiment, the anti-eosinophil monoclonal is directed against human Siglec-8, a cell surface receptor expressed on human eosinophils, which is a member of the CD33-related sialic acid binding Ig-like lectin family. Ligation of Siglec-8 with the monoclonal leads to eosinophil apoptosis and in vivo to eosinophil clearance.

Further provided is a pharmaceutical formulation comprising an isolated recombinant AAV comprising an expression vector encoding an antibody directed against eosinophils, wherein the antibody has a sequence having at least 80% amino acid sequence identity to a polypeptide encoded by SEQ ID NO: 1 or 2, or both, or has at least 80% amino acid sequence identity to a polypeptide comprising at least one of SEQ ID Nos. 3-6, 8-32, 40-41, 43-44, or 46-51, or a combination thereof. The formulation may be employed to inhibit or treat cancer, e.g., eosinophilic cancers, or other hypereosinophilic diseases.

Also provided is a pharmaceutical formulation comprising an amount of an isolated recombinant lentivirus, retrovirus, adenovirus or AAV comprising an expression vector comprising an open reading frame encoding an antibody that binds to a ligand on eosinophils or that binds a molecule, the presence of which in a mammal, increases the number of eosinophils, effective to decrease the number of eosinophils in a mammal. In one embodiment, the antibody comprises a polypeptide comprising a sequence having at least 80% amino acid sequence identity to a polypeptide encoded by SEQ ID NO:1 or 2 or a polypeptide comprising a sequence having at least 80% amino acid sequence identity to a polypeptide composing one of SEQ ID Nos. 3-6, 8-32, 40-41, 43-44, or 46-51. In one embodiment, the antibody binds Siglec-8, IL-4, IL-4R, IL-5, IL-5R, IL-9, IL-9R, IL-13, IL-13R, IL-17, IL-17R, IL-33, IL-33R, CD30, CD52, CCR3, IgE Fc, RADCP, or TNF-alpha. In one embodiment, the pharmaceutical formulation is formulated for intravenous delivery.

BRIEF DESCRIPTION OF FIGURES

FIGS. 9A-B. Murine Models of CEL-NOS (Balb/c (A) and NSG (B)).

FIGS. 17A-B. AAVrh.10mAnti-Eos Reduces Mortality in CEL-NOS Murine Model (NSG males). A) Model. B) Survival plots.

Figure 1A:
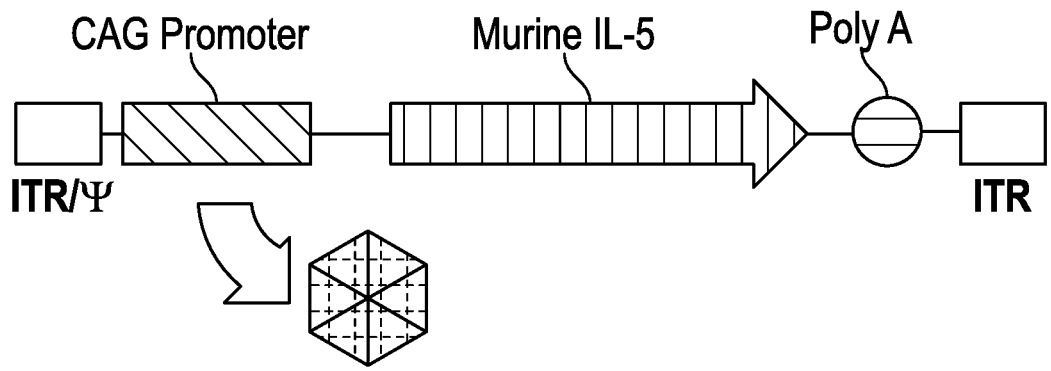
FIGS. 1A-F. Generation of a murine model of CEL-NOS. The model is based on administration to wild-type Balb/C mice by the intravenous route of an AAVrh.10 gene therapy vector expressing murine interleukin 5 (11-5), the primary cytokine that induces the bone marrow to generate eosinophils. A) Schematic of the AAVrh.10mIL-5 vector. B) Schematic of mouse model of CEL-NOS. C) Serum levels of IL5 8 wk after Intravenous administration of AAVrh.10mIL-5. D) Blood smear, naive Balb/C mouse. E) Blood smear, 10 wk after administration of AAVrh.10mIL5 demonstrating hypereosinophilia. F) Absolute blood eosinophil count up to 10 wk following intravenous administration of $2.5 \times 10^{10}$ gc AAVrh.10mIL-5 showing a high, persistent burden of blood eosinophils.
Figure 1B:
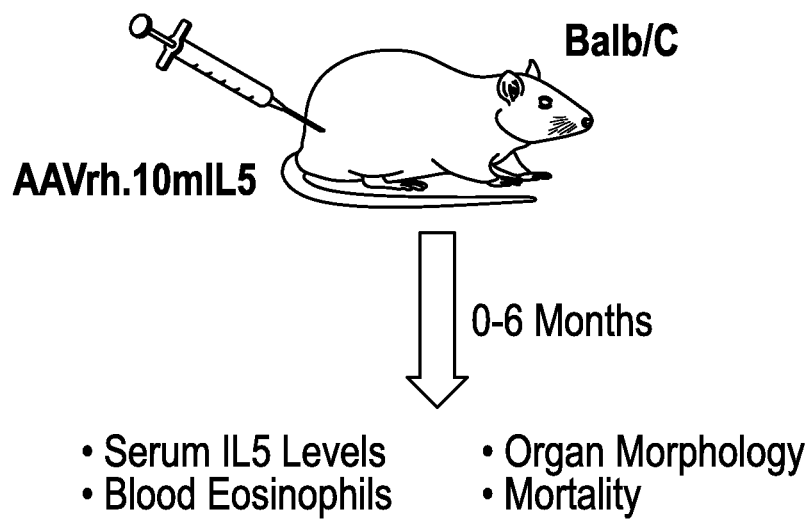
Figure 1C:
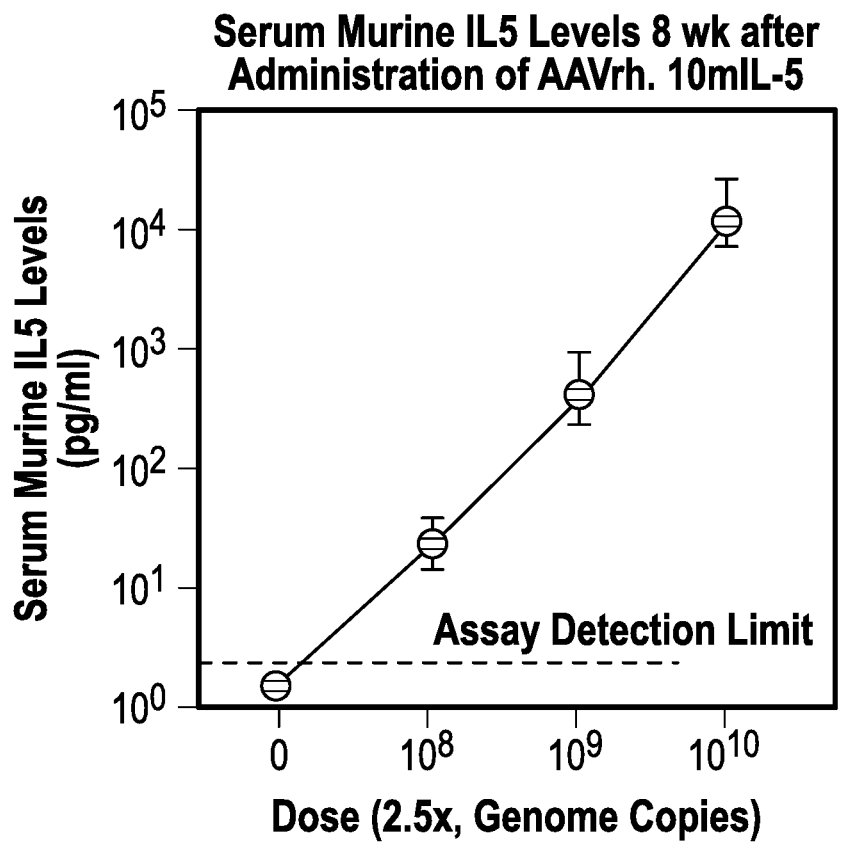
Figure 1D:
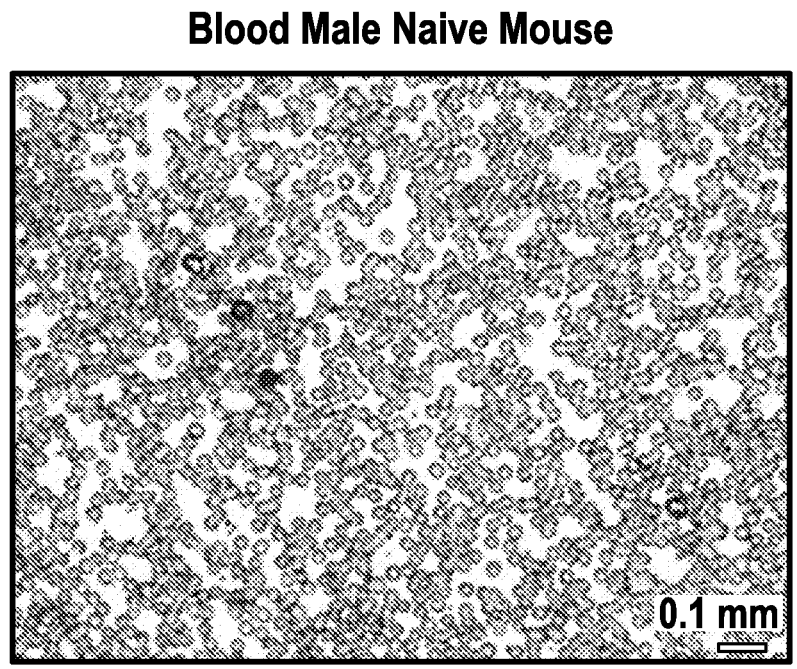
Figure 1E:
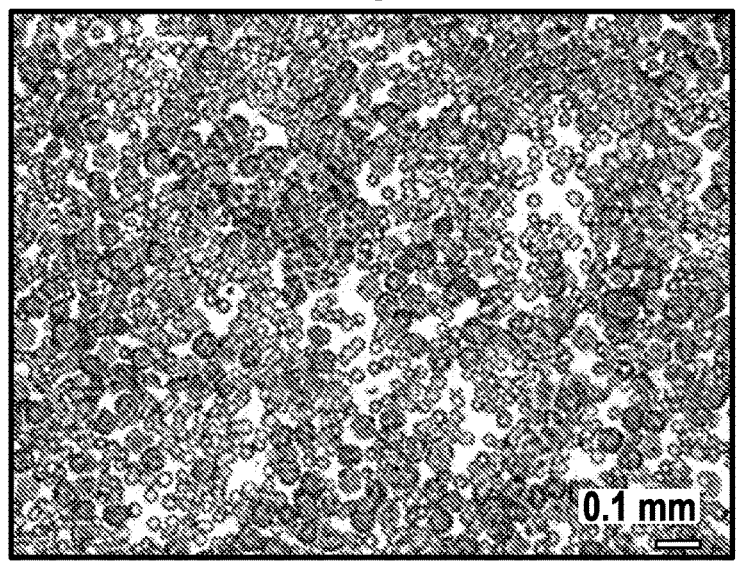
Figure 1F:
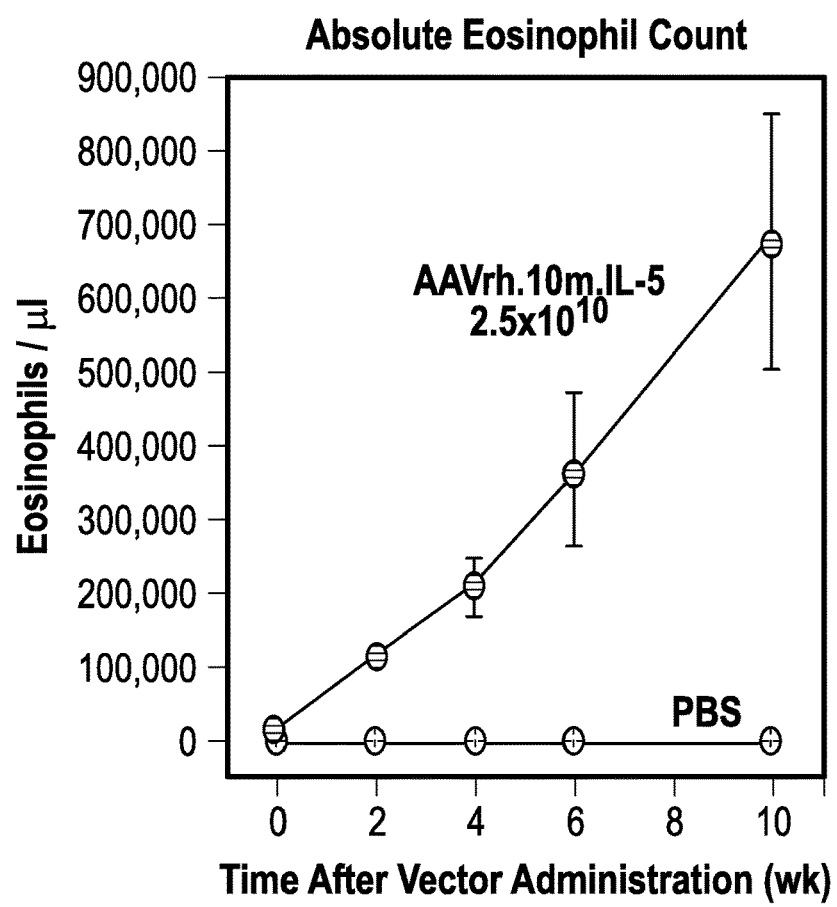
Figure 2:
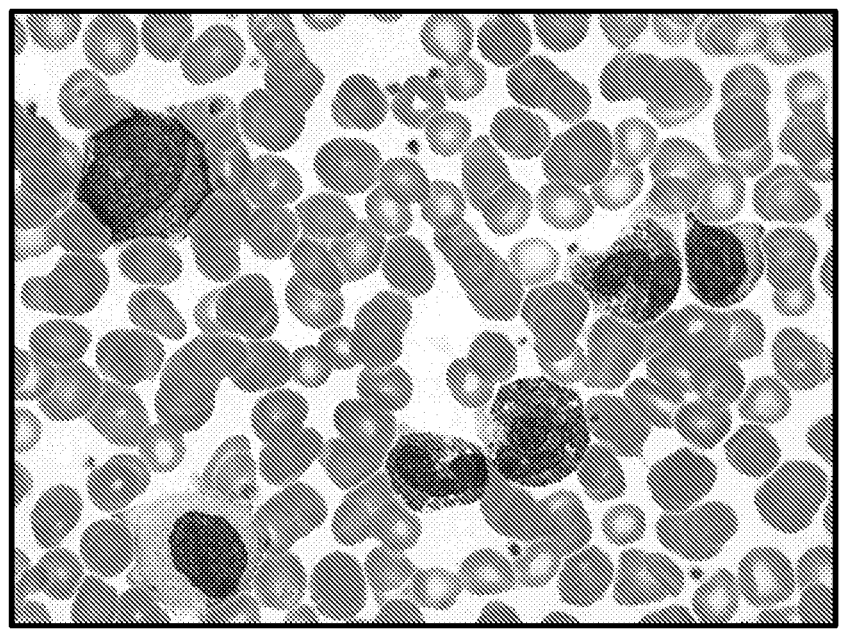
FIG. 2. CEL-NOS blood smear.
Figure 3A:
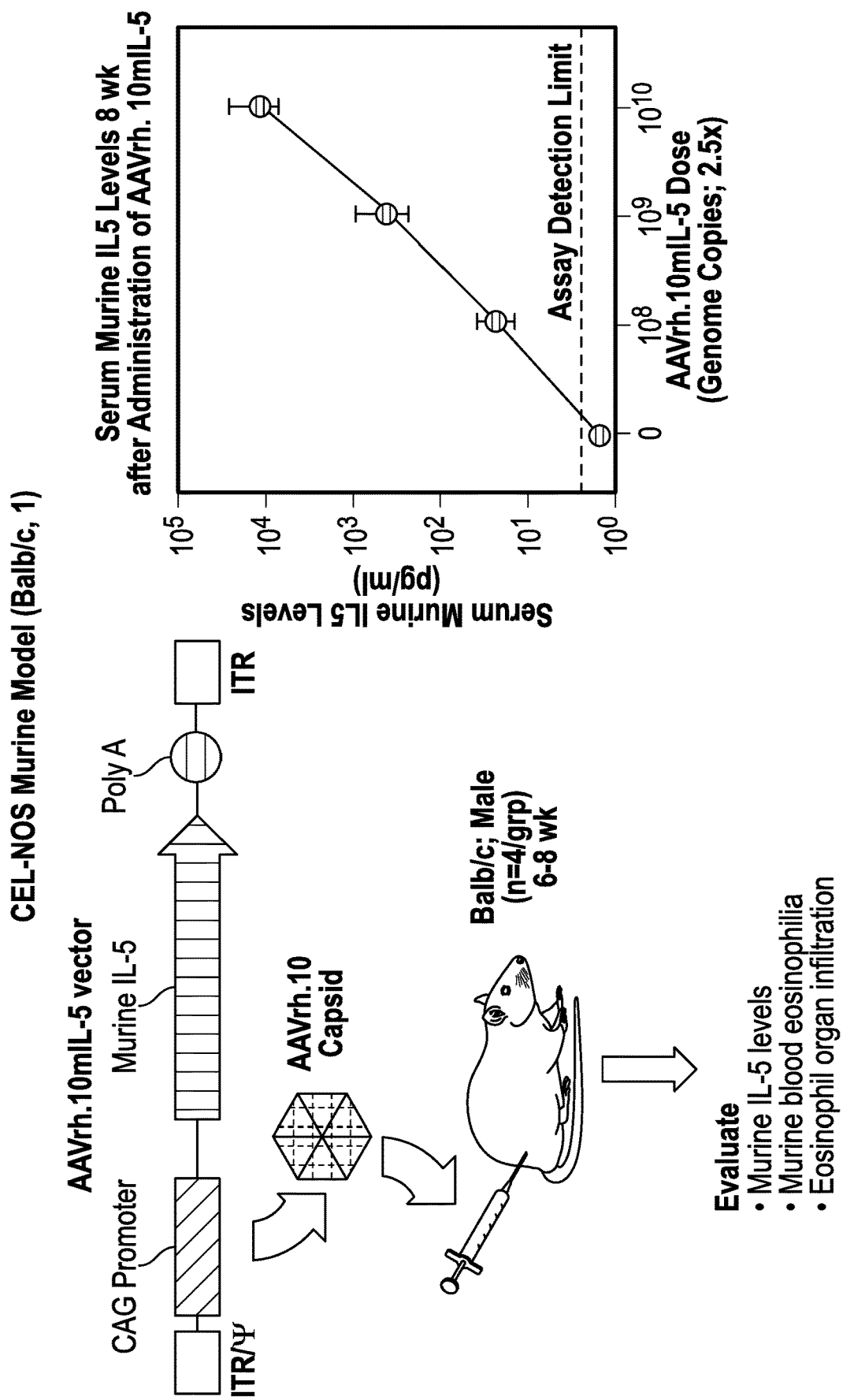
FIGS. 3A-D. CEL-NOS Murine Model (Balb/c). AAVrh.10mIL-5 was used to infect male Balb/c mice (n=4/group) at age 6-8 weeks, after which murine IL-5 levels, blood eosinophilia and eosinophil organ infiltration were evaluated. A) Serum murine IL-5 levels at 8 weeks after administration. B) Absolute eosinophil count. C) Blood smear, PBS mouse. D) Blood smear AAVrh.10mIL-5 infected mouse at 2 weeks post-infection.
Figure 3B:
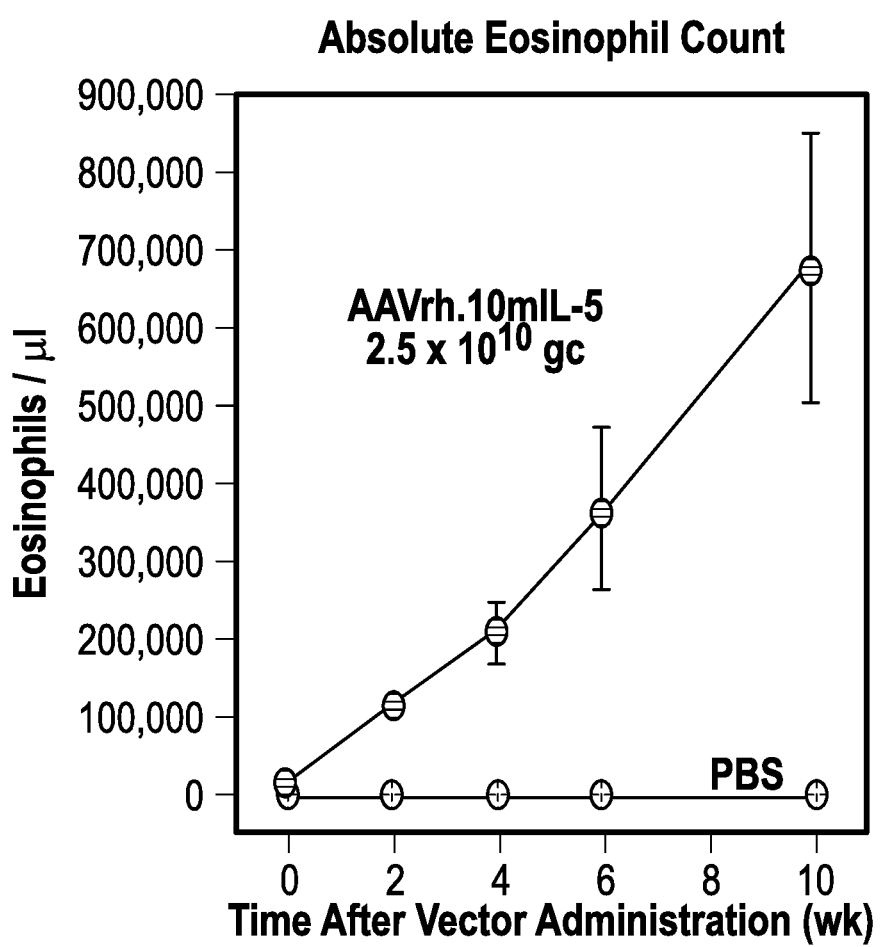
Figure 3C:
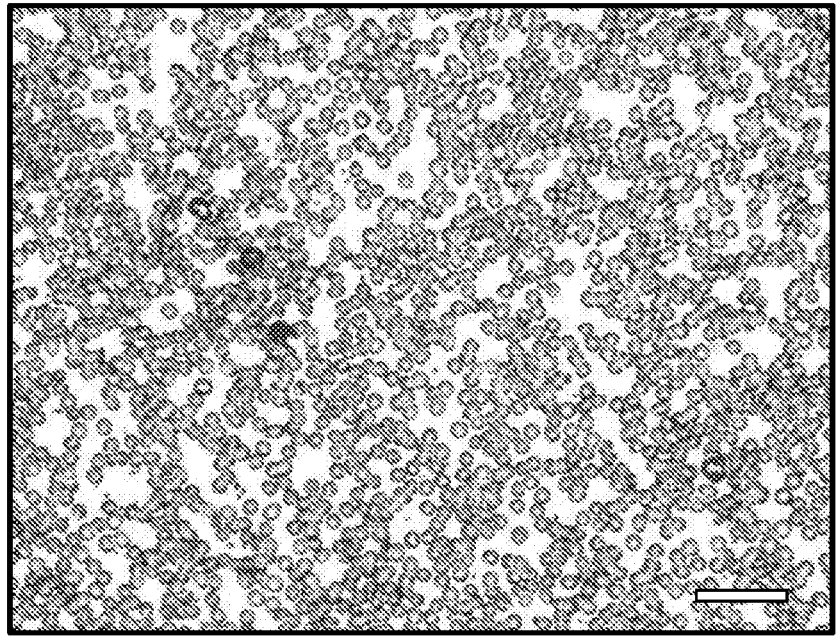
Figure 3D:
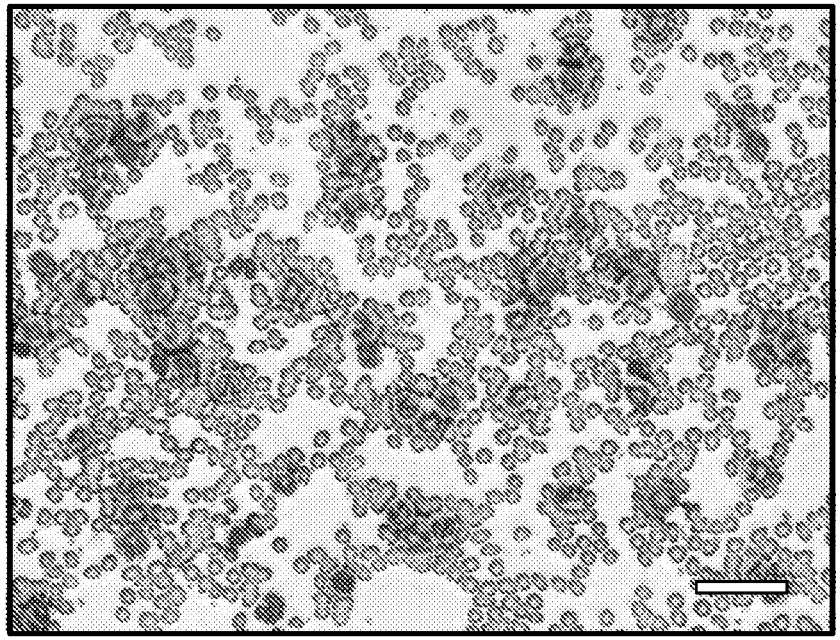
Figure 4A:
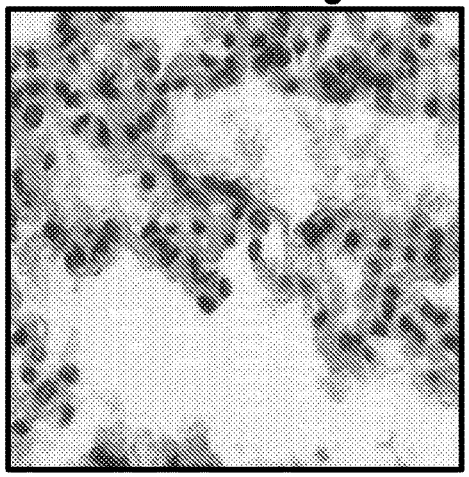
FIGS. 4A-F. CEL-NOS Murine Model (H&E Balb/c). A) Naïve, lung. B) AAVrh.10mIL-5infected, lung. C) Naïve, liver. D) AAVrh.10mIL-5, liver. E) Naïve, heart. F) AAVrh.10mIL-5, heart.
Figure 4B:
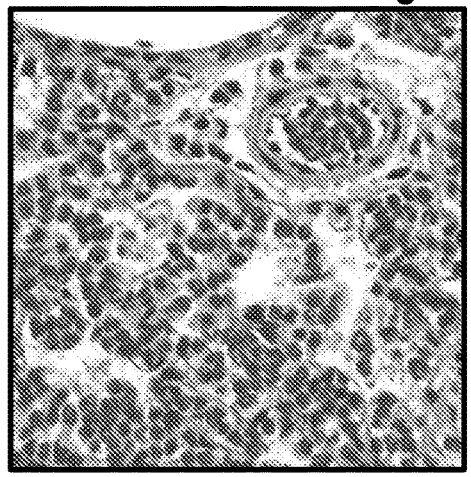
Figure 4C:
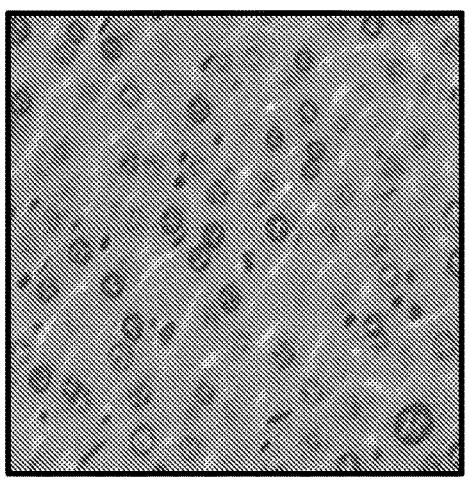
Figure 4D:
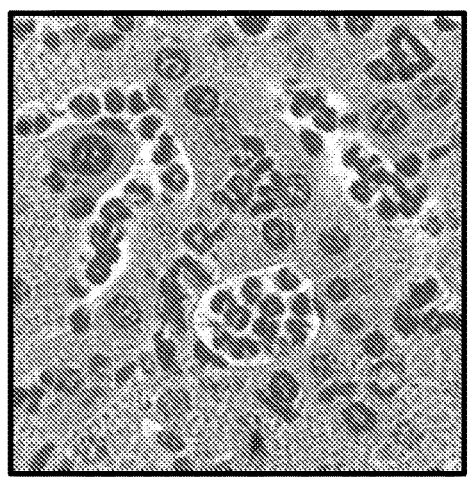
Figure 4E:
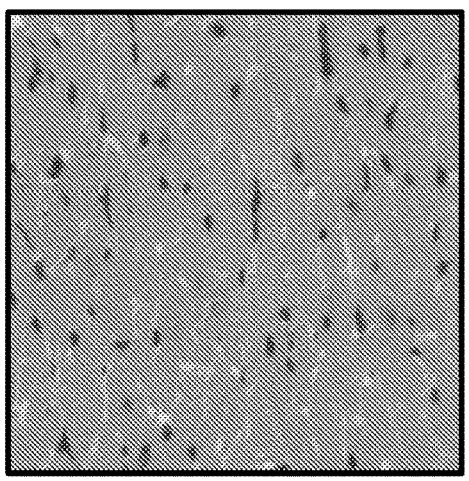
Figure 4F:
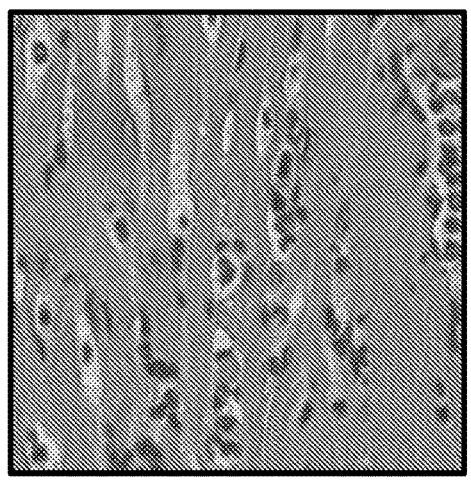
Figure 5A:
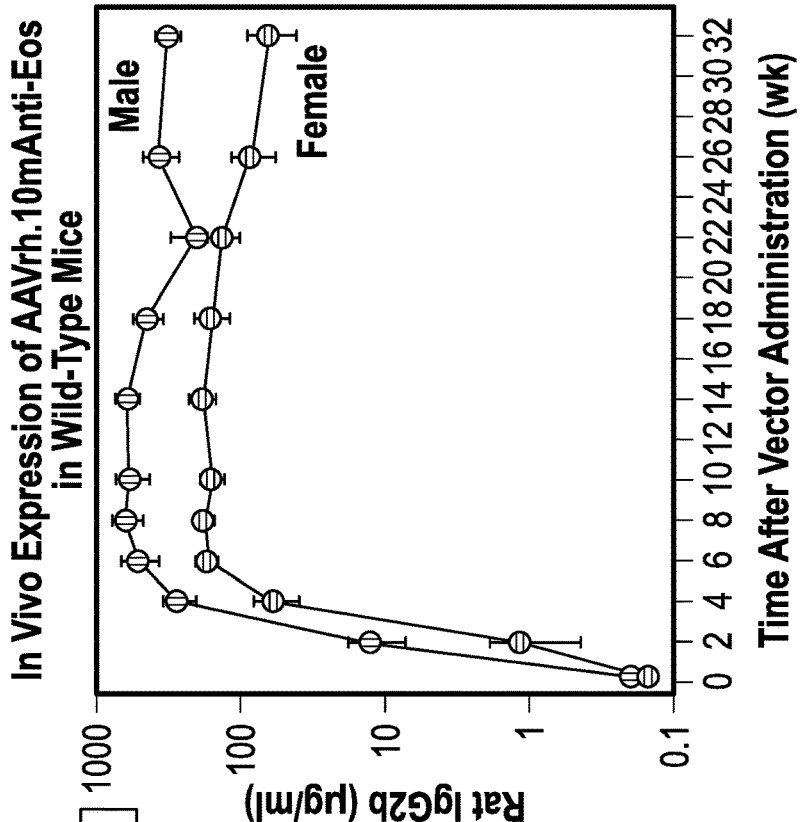
FIGS. 5A-B. Egression of AAVrh.10mAnti-Eos in Wild-Type Mice (Balb/c). AAVrh.10mAnti-Eos ($10^{11}$ gc, IV) was administered to 6-8 week old Balb/c mice (4 males and 4 females) and serum IgG2b levels evaluated. A) In vivo expression of AAVrh.10mAnti-Eos. B) Efficacy in vitro demonstrating induction of apoptosis of murine eosinophils by the product of the vector. Shown is flow cytometry assessment of lactadherin (apoptosis marker) staining of mouse eosinophils.
Figure 5A:
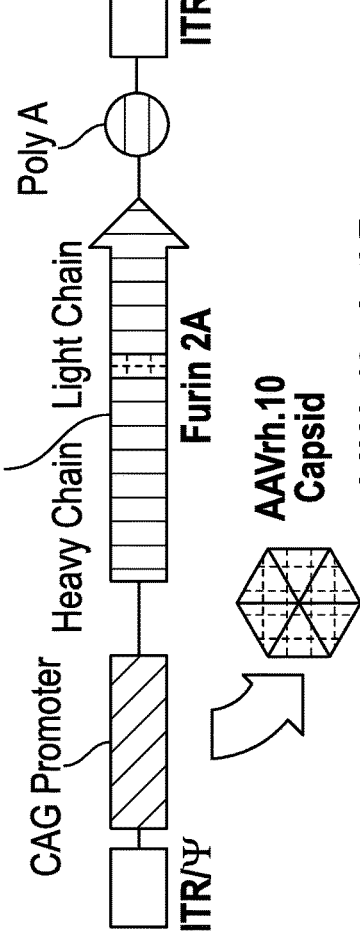
Figure 5A:
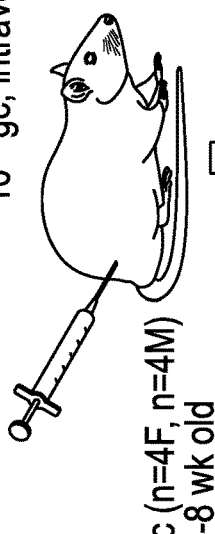
Figure 5A:
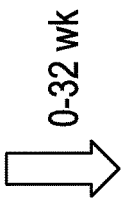
Figure 5B:
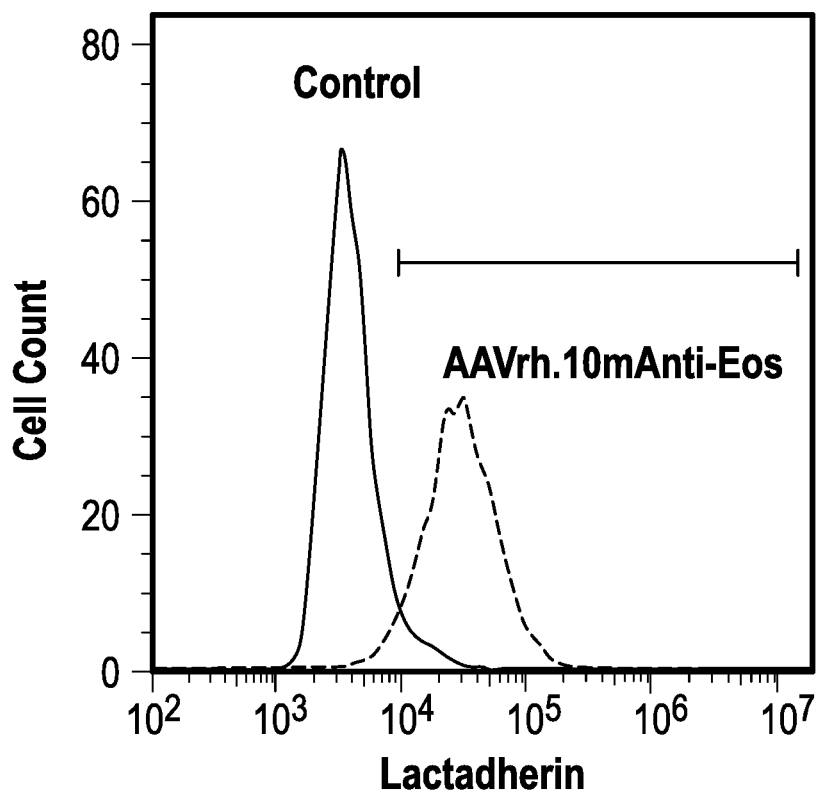
Figure 6:
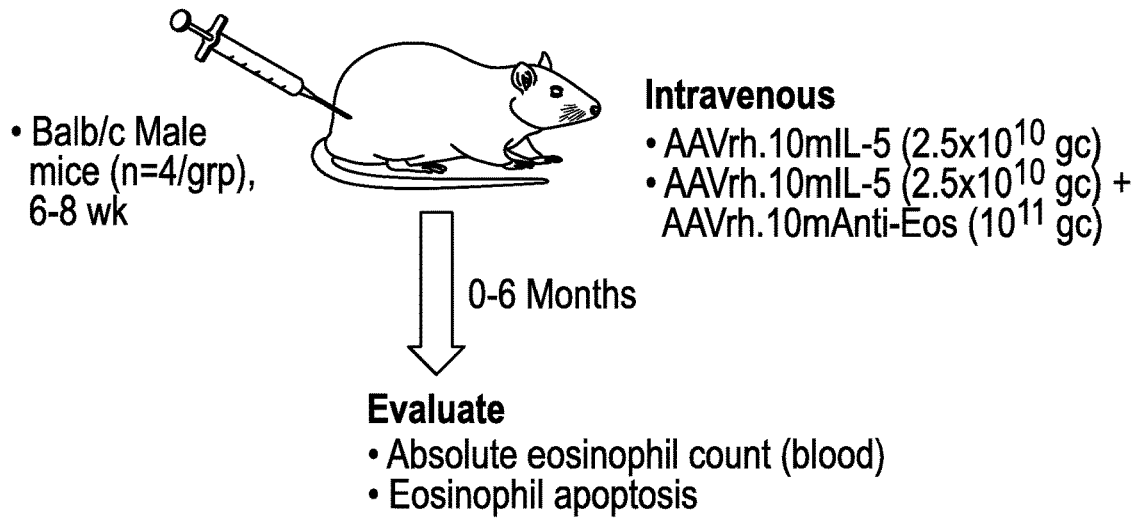
FIG. 6. AAVrh.10mAnti-Eos Therapy in the CEL-NOS Murine Model (Balb/c).
Figure 7A:
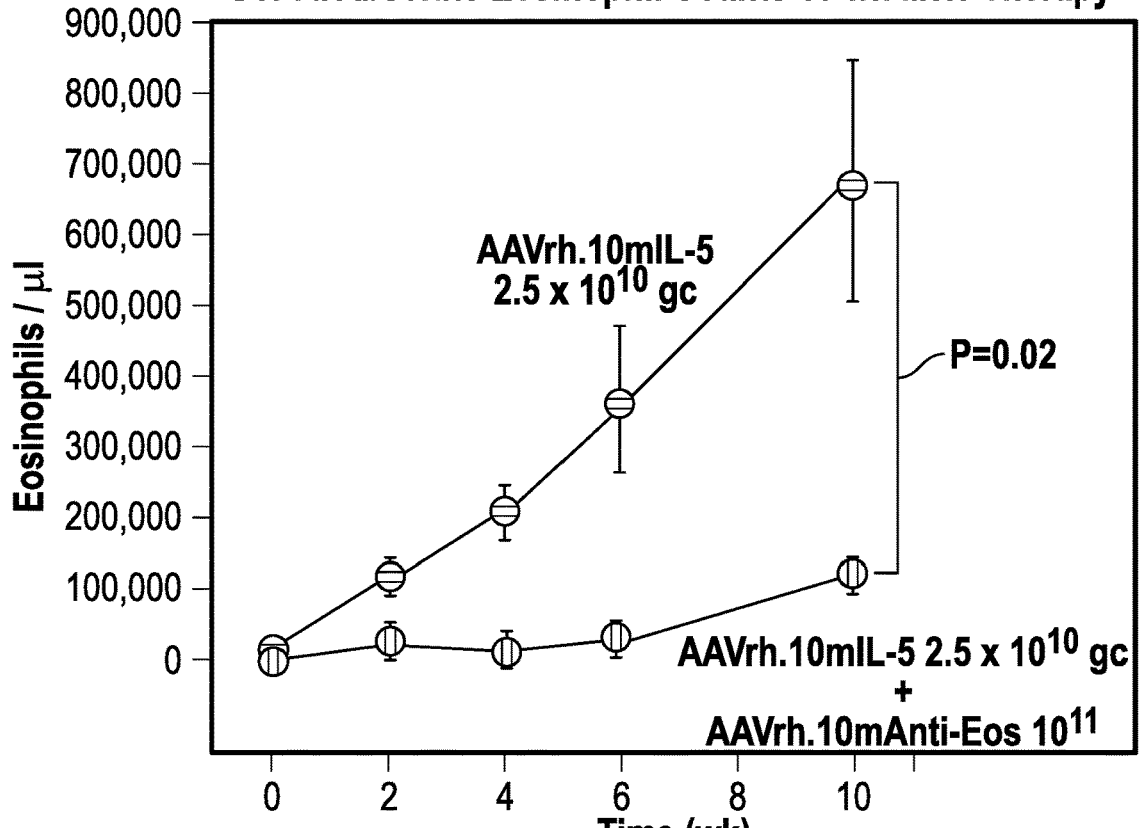
FIGS. 7A-D. AAVrh.10mAnti-Eos Reduces Eosinophil Numbers in the CEL-NOS Murine Model (Balb/c). A) Blood absolute eosinophil count 10 weeks after therapy. B) Eosinophil apoptosis in vivo mediated by AAVrh.10mAnti-Eos. C-D). Blood smears. C) Control, AAVrh.10mIL-5 ($2.5 \times 10^{10}$ gc), at 10 weeks. D) AAVrh.10mAnti-Eos ($10^{11}$ gc) at 10 weeks.
Figure 7B:
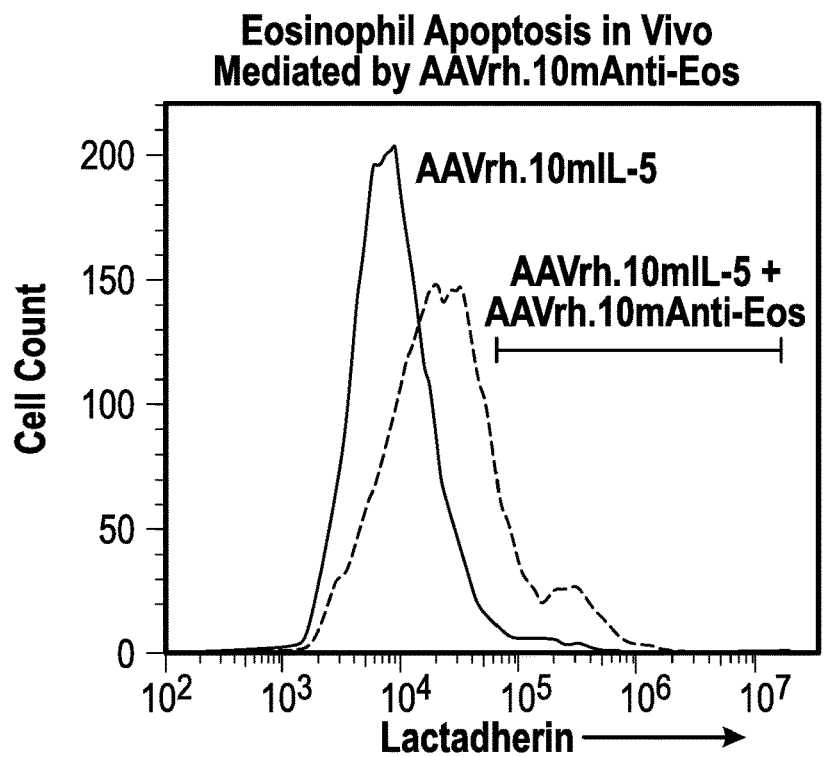
Figure 7C:
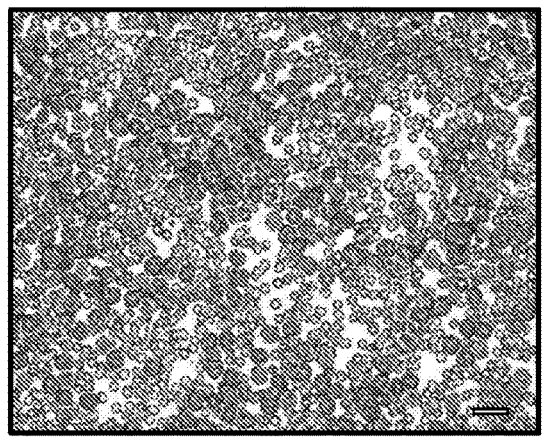
Figure 7D:
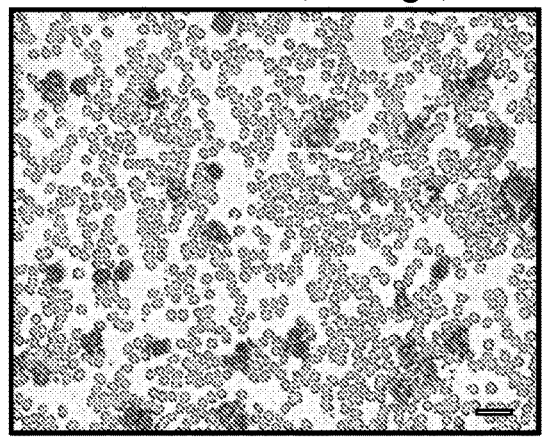

DETAILED DESCRIPTION in the following description, reference is made to the accompanying drawings that form a part hereof, and in which Is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

Definitions

A "vector" refers to a macromolecule or association of macromolecules that comprises or associates with a polynucleotide, and which can be used to mediate delivery of the polynucleotide to a cell, either in vitro or in vivo, illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic interest), a coding sequence of interest in vaccine development (such as a polynucleotide expressing a protein, polypeptide or peptide suitable for eliciting an immune response in a mammal), and/or a selectable or detectable marker.

"Transduction," "transfection," "transformation" or "transducing" as used herein, are terms referring to a process for the introduction of an exogenous polynucleotide into a host cell leading to expression of the polynucleotide, e.g., the transgene in the cell, and includes the use of recombinant virus to introduce the exogenous polynucleotide to the host cell. Transduction, transfection or transformation of a polynucleotide in a cell may be determined by methods well known to the art including, but not limited to, protein expression (including steady state levels). e.g., by ELISA. How cytometry and Western blot, measurement of DNA and RNA by heterologousization assays, e.g., Northern blots, Southern blots and gel shift mobility assays. Methods used for the introduction of the exogenous polynucleotide include well-known techniques such as viral infection or transfection, lipofection, transformation and electroporation, as well as other non-viral gene delivery techniques. The introduced polynucleotide may be stably or transiently maintained in the host cell.

"Gene delivery" refers to the introduction of an exogenous polynucleotide into a cell for gene therapy, and may encompass targeting, binding, uptake, transport, localization, replicon integration and expression.

"Gene therapy" refers to the introduction of an exogenous polynucleotide into a cell which may encompass targeting, binding, uptake, transport, localization and replicon integration, but is distinct from and does not imply subsequent expression of the gene.

"Gene expression" or "egression" refers to the process of gene transcription, translation, and post-translational modification.

An "infectious" virus or viral particle is one that comprises a polynucleotide component which it is capable of delivering into a cell for which the viral species e trophic. The term does not necessarily imply any replication capacity of the virus.

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components, if present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

An "isolated" polynucleotide, e.g., plasmid, virus, polypeptide or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Isolated nucleic acid, peptide or polypeptide is present in a form or setting that is different from that in which it is found in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that a multitude of proteins. The isolated nucleic acid molecule may be present in single-stranded or double-stranded form. When an Isolated nucleic acid molecule is to be utilized to express a protein, the molecule will contain at a minimum the sense or coding strand (i.e., the molecule may single-stranded), but may contain both the sense and anti-sense strands (i.e., the molecule may be double-stranded). Enrichment can be measured on an absolute basis, such as weight per volume of solution, or it can be measured in relation to a second, potentially interfering substance present in the source mixture. Increasing enrichments of the embodiments are envisioned. Thus for example, a 2-fold enrichment, 10-fold enrichment, 100-fold enrichment, or a 1000-fold enrichment.

A "transcriptional regulatory sequence" refers to a genomic region that controls the transcription of a gene or coding sequence to which it is operably linked. Transcriptional regulatory sequences of use generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from the entity to which it is compared. For example, a polynucleotide introduced by genetic engineering techniques into a different cell type is a heterologous polynucleotide (and, when expressed, can encode a heterologous polypeptide). Similarly, a transcriptional regulatory element such as a promoter that is removed from its native coding sequence and operably linked to a different coding sequence is a heterologous transcriptional regulatory element.

A "terminator" refers to a polynucleotide sequence that tends to diminish or prevent read-through transcription (i.e., it diminishes or prevent transcription originating on one aide of the terminator from continuing through to the other side of the terminator). The degree to which transcription is disrupted is typically a function of the base sequence and/or the length of the terminator sequence. In particular, as is well known in numerous molecular biological systems, particular DMA sequences, generally referred to as transcriptional termination sequences' are specific sequences that tend to disrupt read-through transcription by RNA polymerase, presumably by causing the RNA polymerase molecule to stop and/or disengage from the DMA being transcribed. Typical example of such sequence-specific terminators include polyadenylation ("polyA") sequences, e.g., SV40 polyA. In addition to or in place of such sequence-specific terminators, insertions of relatively long DMA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the livelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-non-specific terminators or both. A variety of such terminator sequences are known in the art; and illustrative uses of such sequences within the context of the present disclosure are provided below.

"Host cells," "cell lines," "cell cultures." "packaging cell line" and other such terms denote higher eukaryotic cells, such as mammalian cells including human cells, useful in the present disclosure, e.g., to produce recombinant virus or recombinant fusion polypeptide. These cells Include the progeny of the original cell that was transduced. It is understood that the progeny of a single cell may not necessarily be completely identical (in morphology or in genomic complement) to the original parent cell.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as well as heterologous promoters.

An "expression vector" is a vector comprising a region which encodes a gene product of interest, and is used for effecting the expression of the gene product in an intended target cell. An expression vector also comprises control elements operatively linked to the encoding region to facilitate expression of the protein in the target. The combination of control elements and a gene or genes to which they are operably linked for egression is sometimes referred to as an "expression cassette," a large number of which are known and available in the art or can be readily constructed from components that are available in the art.

The terms "polypeptide" and "protein" are used interchangeably herein to refer to polymers of amino acids of any length. The terms also encompass an amino acid polymer that has been modified; for example, disulfide bond formation, glycosylation, acetylation, phosphonylation, lipidation, or conjugation with a labeling component.

The term "exogenous," when used in relation to a protein, gene, nucleic acid, or polynucleotide in a cell or organism refers to a protein, gene, nucleic acid, or polynucleotide which has been introduced into the cell or organism by artificial or natural means. An exogenous nucleic acid may be from a different organism or cell, or it may be one or more additional copies of a nucleic acid which occurs naturally within the organism or cell By way of a non-limiting example, an exogenous nucleic acid is in a chromosomal location different from that of natural cells, or is otherwise flanked by a different nucleic acid sequence than that found in nature, e.g., an expression cassette which links a promoter from one gene to an open reading frame for a gene product from a afferent gene.

"Transformed" or "transgenic" is used herein to include any host cell or cell line, which has been altered or augmented by the presence of at least one recombinant DNA sequence. The host cells are typically produced by transfection with a DNA sequence in a plasmid expression vector, as an isolated linear DNA sequence, or infection with a recombinant viral vector.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of a selected sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); not less than 9 matches out of 10 possible base pair matches (90%), or not less than 19 matches out of 20 possible base pair matches (95%).

Two amino acid sequences are homologous if there is a partial or complete identity between their sequences. For example, 86% homology means that 85% of the amino acids are identical when the two sequences are aligned (or maximum matching. Gaps (in either of the two sequences being matched) are allowed in maximizing matching; gap lengths of 5 or less are preferred with 2 or less being more preferred. Alternatively, two protein sequences (or polypeptide sequences derived horn them of at least 30 amino acids in length) are homologous, as this term is used herein, if they have an alignment score of at more than 5 (in standard deviation units) using the program ALIGN with the mutation data matrix and a gap penalty of 6 or greater. The two sequences or parts thereof are more homologous W their amino acids are greater than or equal to 50% identical when optimally aligned using the ALIGN program.

The term "corresponds to" is used herein to mean that a polynucleotide sequence is structurally related to all or a portion of a reference polynucleotide sequence, or that a polypeptide sequence is structurally related to al or a portion of (e.g., framework sequences) or CDR sequence(s)) a reference polypeptide sequence, e.g., they have at least 80%, 85%, 90%, 91%, 92%, 93%, 94%, 95%, 96%, 97%, 98%, 99% or 100%, sequence identity. In contradistinction, the term "complementary to" is used herein to mean that the complementary sequence is homologous to al or a portion of a reference polynucleotide sequence. For illustration, the nucleotide sequence "TATAC" corresponds to a reference sequence "TATAC" and is complementary to a reference sequence "GTATA".

The term "sequence identity" means that two polynucleotide sequences are identical (i.e., on a nucleotide-by-nucleotide basis) over the window of comparison. The term "percentage of sequence identity" means that two polynucleotide sequences are Identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage d sequence identity is calculated by comparing the reference sequence to the polynucleotide sequence which may include deletions or additions which total 20 percent or less of the reference sequence over the window of comparison.

"Conservative" amino acid substitutions are, for example, aspartic-glutamic as polar acidic amino acids; lysine/arginine/histidine as polar basic amino acids; leucine/isoleucine/methionine/valine/alanine/glycine/proline as non-polar or hydrophobic amino acids; serine/threonine as polar or uncharged hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan, a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting polypeptide. Whether an amino acid change results in a functional polypeptide can readily be determined by assaying the specific activity of the polypeptide. Naturally occurring residues are divided into groups based on common side-chain properties: (1) hydrophobic: norleucine, met, ala, val, leu, ile; (2) neutral hydrophilic: cys, ser, thr; (3) acidic: asp, glu: (4) basic: asn, gin, his, lys, arg: (5) residues that influence chain orientation: gly, pro; and (6) aromatic: trp, tyr, phe.

The disclosure also envisions polypeptides with non-conservative substitutions. Non-conservative substitutions entail exchanging a member of one of the classes described above for another.

"Nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides.

Nucleic Acid Sequence Encoding a Polypeptide that Forms an Antibody Directed Against Eosinophils or a Molecule that Increases Eosinophil Number One of ordinary skill in the art will appreciate that an antibody consists of four polypeptides: two identical copies of a heavy (H) chain polypeptide and two copies of a light (L) chain polypeptide. Each of the heavy chains contains one N-terminal variable ($V_H$) region and three C-terminal constant (CH1, CH2 and CH3) regions, and each light chain contains one N-terminal variable ($V_L$) region and one C-terminal constant ($C_L$) region. The variable regions of each pair of light and heavy chains form the antigen binding site of an art body. The nucleic acid sequence which encodes an antibody that binds to a ligand on eosinophils or that binds a molecule, the presence of which in the mammal, increases the number of eosinophils (an "anti-eosinophil" antibody) can comprise one or more nucleic acid sequences, each of which encodes one or more of the heavy and/or light chain polypeptides of an anti-eosinophil antibody. In this respect, the nucleic acid sequence which encodes an antibody that binds to a ligand on eosinophils or that binds a molecule, the presence of which in the mammal, increases the number of eosinophils can comprise a single nucleic acid sequence that encodes the two heavy chain polypeptides and the two light chain polypeptides of an anti-eosinophil antibody. Alternatively, the nucleic acid sequence which encodes an antibody that binds to a ligand on eosinophils or that binds a molecule, the presence of which in the mammal, increases the number of eosinophils can comprise a first nucleic acid sequence that encodes both heavy chain polypeptides of an anti-eosinophil antibody, and a second nucleic acid sequence that encodes both light chain polypeptides of an anti-eosinophil antibody. In yet another embodiment, the nucleic acid sequence which encodes an antibody that binds to a ligand on eosinophils or that binds a molecule, the presence of which in the mammal, increases the number of eosinophils can comprise a first nucleic acid sequence encoding a first heavy chain polypeptide of an anti-eosinophilia antibody, a second nucleic acid sequence encoding a second heavy chain polypeptide of an anti-eosinophil antibody, a third nucleic acid sequence encoding a first light chain polypeptide of an anti-eosinophil antibody, and a fourth nucleic acid sequence encoding a second light chain polypeptide of an anti-eosinophil antibody.

In another embodiment, the nucleic acid sequence which encodes an antibody that binds to a ligand on eosinophils or that binds a molecule, the presence of which in the mammal, increases the number of eosinophils encodes an antigen-binding fragment (also referred to as an "antibody fragment") of an anti-eosinophil antibody. The term "antigen-binding fragment" refers to one or more fragments of an antibody that retain the ability to specifically bind to an antigen (e.g., eosinophil). Examples of antigen-binding fragments include but are not limited to (i) a Fab fragment, which is a monovalent fragment consisting of the $V_L$, $V_H$, $C_L$, and $C_{H1}$ domains; (ii) a F(ab')2 fragment, which is a bivalent fragment comprising two Fab fragments linked by a disulfide bridge at the hinge region; and (iii) a Fv fragment consisting of the $V_L$ and $V_H$ domains of a single arm of an antibody. In one embodiment, the nucleic acid sequence which encodes an antibody that binds to a ligand on eosinophils or that binds a molecule, the presence of which in the mammal, increases the number of eosinophils can comprise a nucleic acid sequence encoding a Fab fragment of an anti-eosinophil antibody.

An antibody, or antigen-binding fragment thereof, can be obtained by any means, including via in vitro sources (e.g., a hybridoma or a cell line producing an antibody recombinantly) and in vivo sources (e.g., rodents). Methods for generating antibodies are known in the art and are described in, for example, Köhler and Milstein. Eur. *J. Immunol.,* 5:511 (1976); Harlow and Lane (eds.), *Antibodies: A Laboratory Manual*, CSH Press (1988): and C. A. Janeway et al. (eds.), *Immunobiology.* 5th Ed., Garland Publishing, New York, NY (2001)). In certain embodiments, a human antibody or a chimeric antibody can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the HUMAB-MOUSE™, the Kirin TC MOUSE™, and the KM-MOUSE™ (see, e.g., Lonberg, *Nat. Biotechnol.,* 22(9):1117 (2005), and Lonberg, *Handb. Exp. Pharmacol.,* 181:69 (2008)).

The nucleic acid sequence which encodes an antibody that binds to a ligand on eosinophils or that binds a molecule, the presence of which in the mammal, increases the number of eosinophils, or an antigen-binding fragment thereof, can be generated using methods known in the art. For example, nucleic acid sequences, polypeptides, and proteins can be recombinantly produced using standard recombinant DNA methodology (see, e.g., Sambrook et al., *Molecular Cloning: A Laboratory Manual.* 3rd ed., Cold Spring Harbor Press. Cold Spring Harbor, NY, 2001: and Ausubel et al., *Current Protocols in Molecular Biology, Greene Publishing Associates and John Wiley* 8 Sons, N Y, 1994). Further, a synthetically produced the nucleic acid sequence which encodes an antibody that binds to a ligand on eosinophils or that binds a molecule, the presence of which in the mammal, increases the number of eosinophils, or an antigen-binding fragment thereof, can be isolated and/or purified from a source, such as a bacterium, an insect, or a mammal, e.g., a rat, a human, etc. Methods of isolation and purification are wen-known in the art. Alternatively, the nucleic acid sequences described herein can be commercially synthesized. In this respect, the nucleic acid sequence can be synthetic, recombinant. Isolated, and/or purified.

The nucleic acid sequence which encodes an antibody that binds to a ligand on eosinophils or that binds a molecule, the presence of which in the mammal, increases the number of eosinophils may be identified by extracting RNA from the available antibody producing hybridoma cells. cDNA is produced by reverse transcription and PCR amplification of the light and heavy chains and is carried out using a rapid amplification of cDNA ends (RACE) strategy in combination with specific primers for conserved regions in the constant domains.

The nucleic acid sequence which encodes an antibody that binds to a ligand on eosinophils or that binds a molecule, the presence of which in the mammal, increases the number of eosinophils may also be fully or partly humanized by means known in the art. For example, an antibody chimera may be created by substituting DNA encoding the mouse Fc region of the antibody with that of cDNA encoding for human.

The Fab portion of the molecule may also be humanized by selectively altering the DNA of non-CDR portions of the Fab sequence that differ from those in humans by exchanging the sequences for the appropriate individual amino acids.

Alternatively, humanization may be achieved by insertion of the appropriate CDR coding segments into a human antibody "scaffold".

Resulting antibody DNA sequences may be optimized for high expression levels in mammalian cells through removal of RNA instability elements, a is known in the art.

In an embodiment, a nucleic acid sequence which encodes a polypeptide that forms an antibody, e.g., forms an antibody having two light chains and two heavy chains, a scFV, a chimeric antibody, a single heavy chain and the like, that binds to a ligand on eosinophils or that binds a molecule, the presence of which in the mammal, increases the number of eosinophils, may be expressed under the control of a single promoter, e.g., using a 2A (Chysel) self-cleavable sequence between heavy and light chains. The 2A sequence self-cleaves during protein translation and leaves a short tail of amino acids in the C-terminus of the upstream protein. A Furin cleavage recognition site may be added between the 2A sequence and the upstream gene to assure removal of the remaining amino acids. Plasmids expressing the correct inserts may be identified by DNA sequencing and by antibody specific binding using western analysis and ELISA assays.

In an embodiment a nucleic acid sequence which encodes a polypeptide that forms an antibody that binds to a ligand on eosinophils or that binds a molecule, the presence of which in the mammal, increases the number of eosinophils, may be operably linked to a heterologous signal peptide, e.g., a signal peptide from IL-2, IL-6, CD5, trypsinogen, serum albumin, prolactin, elastin, chymotrypsin, IL-2, trypsinogen-2, or avastin (MKYLLPTAAAGLLLLAAQ-PAMA (SEQ ID NO:60) or MEFGLSWLFLVAILKGVQC (SEQ ID NO:61)) or a signal peptide from another immunoglobulin (e.g., see Table 1 in Haryadi et al., *PloS One.* 10:e0116878 (2015), which is incorporated by reference herein) or a homologous signal peptide from an immunoglobulin, expressed under the control of a single promoter, or a light chain and a heavy chain may be expressed from different promoters and may have the same or different signal peptides. Plasmids expressing the correct inserts may be identified by DNA sequencing and by antibody specific binding using western analysis and ELISA assays.

Anti-Eosinophil-Based Therapies

Eosinophils are bone marrow derived granulocytic cells. Their development is regulated by interleukin-5 (IL-5). Eosinophils have a role in combating parasites pathogens and in the pathogenesis of allergic and asthmatic disorders. They persist in the circulation for about 8 to 12 hours and survive in tissues for about 8 to 12 days. In a normal mammal, eosinophils are <5% of blood leukocytes (300-500/µl). They can release a variety of cytotoxic mediators from cytoplasmic granules.

The normal eosinophil count in the peripheral blood ranges from 50 to $500 \times 10^9$/l. Blood eosinophilia can be divided into mild eosinophilia (up to $1500 \times 10^9$/l) and marked eosinophilia (>$1500 \times 10^9$/l). In 'tissue HE' there are substantial numbers of eosinophils are observed in the BM and in lymphatic organs as well as in the mucosal linings of the intestinal tract especially the stomach, small intestine and colon. In most other tissues and organs, however, even low numbers of eosinophils can be regarded as 'eosinophilia'. Tissue HE is characterized by a local marked increase in eosinophils and/or marked deposition of eosinophil-derived proteins such as MBP. Based on underlying conditions and etiology, several variant forms of HE exist:

a hereditary (familial) form (HEF), HE of undetermined (clinical) significance (HEUS), primary (neoplastic) HE (HEN) where eosinophils are considered to be clonal cells and secondary (reactive) HE (HER) where eosinophils are considered to be nonclonal cells expanded (and activated) by a reactive process. Rarely, HER is triggered by a clonal process such as Hodgkin's lymphoma or lung adenocarcinoma.

CEL-NOS is a subtype of adult chronic eosinophilic leukemia of unknown cause, it is characterized by a persistent elevation of blood eosinophils ($>1.5\times10^1$/MI) which results in dysfunction of organs infiltrated with eosinophils. Symptoms of CEL-NOS include but are not limited to cough, weakness, diarrhea, hepatosplenomegaly, cardiac and lung dysfunction. Individuals with CEL-NOS are unresponsive to therapy, and have a median survival from diagnosis of 2 years.

A gene therapy based approach to hypereosinophilia includes, in one embodiment the use of viral vectors, e.g., a single administration of an AAV vector, coding for an anti-eosinophil monoclonal antibody (e.g., AAVrh.10mAnti-Eos), to provide sustained expression of the anti-eosinophil monoclonal, lowering blood and tissue eosinophil levels in vivo and decrease mortality. As described hereinbelow, a mouse model of CEL-NOS was generated using an AAV vector coding for murine IL-5, expressing high sustained levels of IL-5 resulting in persistent stimulation of bone marrow to generate eosinophils. An AAV based gene therapy vector was prepared, e.g., AAVrh.10mAnti-Eos), an AAV vector coding for anti-Siglec-F, a rat IgG2b monoclonal antibody specific for an eosinophil cell surface immunoglobulin-like lectin. As disclosed herein, Balb/c mice were administered AAVrh.10mIL-5 and AAVrh.10mAnti-Eos simultaneously on day 0. To circumvent pre-existing immunity to vector, immunodeficient NOD-scid IL2 Rgamma$^{null}$ (NSG) mice were used. NSG mice injected with AAVrh.10mIL-5 on day 0. Day 28 (titer phenotype establishment), AAVrh.10mAnti-Eos was injected. In addition, mouse models of CEL-NOS were generated with characteristics associated with CEL-NOS in humans. The phenotype was independent of acquired immunity. One time administration of AAVrh.10mAnti-Eos to CEL-NOS mice resulted in sustained anti-Siglec-F levels and provided long term suppression of eosinophils in blood in the affected mice. Thus, AAVrh.10mAnti-Eos suppressed eosinophil numbers and reduced mortality in the CEL-NOS mouse model.

The strategy to protect from chronic persistence of high levels of eosinophils is applicable to other hypereosinophilic disorders, e.g., those without other treatment options.

Gone Therapy Vectors

The disclosure provides a gene therapy vector comprising a nucleic acid sequence which encodes a monoclonal antibody that binds to a ligand on eosinophils or that binds a molecule, the presence of which in the mammal, increases the number of eosinophils. The disclosure further provides a method of producing an immune response against eosinophil in a mammal, which method comprises administering to the mammal the above-described gene therapy vector. Various aspects of the gene therapy vector and method are discussed below. Although each parameter is discussed separately, the gene therapy vector and method comprise comb nations of the parameters set forth below to evoke protection against an eosinophil associated pathology. Accordingly, any combination of parameters can be used according to the gene therapy vector and the method.

A "gene therapy vector" is thus any molecule or composition that has the ability to carry a heterologous nucleic acid sequence into a suitable host cell where synthesis of the encoded protein takes place. Typically, a gene therapy vector is a nucleic acid molecule that has been engineered, using recombinant DMA techniques that are known in the art, to incorporate the heterologous nucleic acid sequence. Desirably, the gene therapy vector is comprised of DMA. Examples of suitable DNA-based gene therapy vectors include plasmids and viral vectors. However, gene therapy vectors that are not based on nucleic acids, such as liposomes, are also known and used in the art. The gene therapy vector can be based on a single type of nucleic acid (e.g., a plasmid) or non-nucleic acid molecule (e.g., a lipid or a polymer). The gene therapy vector can be integrated into the host cell genome, or can be present in the host cell in the form of an episome.

Gene delivery vectors within the scope of the disclosure include, but are not limited to, isolated nucleic acid, e.g., plasmid-based vectors which may be extrachromosomally maintained, and viral vectors, e.g., recombinant adenovirus, retrovirus, lentivirus, herpesvirus, poxvirus, papilloma virus, or adeno-associated virus, including viral and non-viral vectors which are present in liposomes, e.g., neutral or cationic liposomes, such as DOSPA/DOPE, DOGS/DOPE or DMRIE/DOPE liposomes, and/or associated with ether molecules such as DNA-anti-DNA antibody-cationic lipid (DOTMA/DOPE) complexes. Exemplary viral gene delivery vectors are desorbed below. Gene delivery vectors may be administered via any route including, but not limited to, intracranial, intrathecal, intramuscular, buccal, rectal, intravenous or intracoronary administration, and transfer to cells may be enhanced using electroporation and/or iontophoresis, and/or scaffolding such as extracellular matrix or hydrogels, e.g., a hydrogel patch.

In one embodiment, the gene therapy vector is a viral vector. Suitable viral vectors include, for example, retroviral vectors, lentivirus vectors, herpes simplex virus (HSV)-based vectors, parvovirus-based vectors, e.g., adeno-associated virus (AAV)-based vectors, AAV-adenoviral chimeric vectors, and adenovirus-based vectors. These viral vectors can be prepared using standard recombinant DNA techniques described in, for example, Sambrook et al., *Molecular Cloning, a Laboratory Manual,* 3rd edition, Cold Spring Harbor Press, Cold Spring Harbor, N.Y. (2001), and Ausubel et al., *Current Protocols in Molecular Biology,* Greene Publishing Associates and John Wiley 4 Sons, New York, N.Y. (1994).

Retroviral Vectors

Retroviral vectors exhibit several distinctive features including their ability to stably and precisely integrate into the host genome providing long-term transgene expression. These vectors can be manipulated ex vivo to eliminate infectious gene particles to minimize the risk of systemic infection and patient-to-patient transmission. Pseudotyped retroviral vectors can alter host cell tropism.

Lentiviruses

Lentiviruses are derived from a family of retroviruses that Include human Immunodeficiency virus and feline immunodeficiency virus. However, unlike retroviruses that only infect dividing cells, lentiviruses can infect both dividing and nondividing cells. For instance, lentiviral vectors based on human immunodeficiency virus genome are capable of efficient transduction of cardiac myocytes in vivo. Although lentiviruses have specific tropisms, pseudotyping the viral envelope with vesicular stomatitis virus yields virus with a broader range (Schnepp et al., *Meth. Mol. Med.,* 69:427 (2002)).

Adenoviral Vectors

Adenoviral vectors may be rendered replication-incompetent by deleting the early (E1A and E1B) genes responsible for viral gene expression from the genome and are stably maintained into the host cells m an extrachromosomal form. These vectors have the ability to transfect both replicating and nonreplicating cells and, in particular, these vectors have been shown to efficiently infect cardiac myocytes in vivo, e.g., after direction injection or perfusion. Adenoviral vectors have been shown to result in transient expression of therapeutic genes in vivo, peaking at 7 days and lasting approximately 4 weeks. The duration of transgene expression may be improved in systems utilizing neural specific promoters. In addition, adenoviral vectors can be produced at very high titers, allowing efficient gene therapy with small volumes of virus.

Adeno-Associated Virus Vectors

Recombinant adeno-associated viruses (rAAV) are derived from nonpathogenic parvoviruses, evoke essentially no cellular immune response, and produce transgene expression lasting months in most systems. Moreover, like adenovirus, adeno-associated virus vectors also have the capability to infect replicating and non replicating cells and are believed to be nonpathogenic to humans. Moreover, they appear promising for sustained cardiac gene therapy (Hoshijima et al. Nat. Med., 5864 (2002); Lynch et al., Circ. Res., 80:197 (1997)).

Plasmid DNA Vectors

Plasmid DNA Is often referred to as "naked DNA" to indicate the absence of a more elaborate packaging system. Direct injection of plasmid DNA to myocardial cells in vivo has been accomplished. Plasmid-based vectors are relatively nonimmunogenic and nonpathogenic, with the potential to stably integrate in the cellular genome, resulting in long-term gene expression in postmitotic cells in vivo. For example, expression of secreted angiogenesis factors after muscle injection of plasmid DNA, despite relatively low levels of local transgene expression, has demonstrated significant biologic effects in animal models and appears promising clinically (Isner, Nature. 415:234 (2002)). Furthermore, plasmid DNA is rapidly wdegraded in the blood stream; therefore, the chance of transgene expression in distant organ systems is negligible. Plasmid DNA may be delivered to cells as part of a macromolecular complex, e.g., a liposome or DNA-protein complex, and delivery may be enhanced using techniques including electroporation.

Exemplary AAV Vectors

In an embodiment, the disclosure provides an adeno-associated virus (AAV) vector which comprises, consists essentially of, or consists of a nucleic acid sequence encoding an antibody that binds to an eosinophil, or an antigen-binding fragment thereof. When the AAV vector consists essentially of a nucleic acid sequence encoding an antibody that binds to an eosinophil, additional components can be included that do not materially affect the AAV vector (e.g., genetic elements such as poly(A) sequences or restriction enzyme sites that facilitate manipulation of the vector in vitro). When the AAV vector consists of a nucleic acid sequence which encodes a monoclonal antibody that binds to a ligand on eosinophils or that binds a molecule, the presence of which in the mammal, increases the number of eosinophils, the AAV vector does not comprise any additional components (i.e., components that are not endogenous to AAV and are not required to effect expression of the nucleic acid sequence to thereby provide the antibody).

Adeno-associated virus is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DMA replication by serving as primers for the cellular DMA polymerase complex. The Rep genes encode the Rep proteins Rep78. Rep68, Rep62, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see. e.g., Im et al., Cell. 51:447 (1990)). These proteins also regulate transcription from endogenous AAV promoters and promoters within helper viruses (see, e.g., Pereira et al., J. Virol., 71:1079 (19971). The other Rep proteins modify the function of Rep78 and Rep68. The cap genes encode the capsid proteins VP1, VP2, and VP3. The cap genes are transcribed from the p40 promoter.

The AAV vector may be generated using any AAV serotype known in the art. Several AAV serotypes and over 100 AAV variants have been isolated from adenovirus stocks or from human or nonhuman primate tissues (reviewed in. e.g., Wu et al., Molecular Therapy. 14(3): 316 (2006)). Generally, the AAV serotypes have genomic sequences of significant homology at the nucleic acid sequence and amino acid sequence levels, such that different serotypes have an identical set of genetic functions, produce virions which are essentially physically and functionally equivalent and replicate and assemble by practically identical mechanisms. AAV serotypes 1-5 and 7-9 are defined as "true" serotypes, in that they do not efficiently cross-read with neutralizing sera specific for all other existing and characterized serotypes. In contrast, AAV serotypes 6, 10 (also referred to as Rh10), and 11 are considered "variant" serotypes as they do not adhere to the definition of a "true" serotype. AAV serotype 2 (AAV2) has been used extensively for gene therapy a op Re alone due to its lack of pathogenicity, wide range of infectivity, and ability to establish long-term transgene expression (see, e.g., Carter, Hum. Gone Ther., 15:541 (2005); and Wu et al., supra). Genome sequences of various AAV serotypes and comparisons thereof are disclosed in, for example, GenBank Accession numbers U89790, J01901, AF043303, and AF085716: Chiorini et al., J. Virol., 71:6823 (1997); Srivastava et al., J. Virol., 45:565 (1983); Chiorini et al., J. Virol. 23:1309 (1999); Rutledge et al., J. Virol., 22-309 (1998); and Wu et al., J. Virol., 24:8635 (2000)).

AAV rep and ITR sequences are particularly conserved across most AAV serotypes. For example, the Rep78 proteins of AAV2, AAV3A, AAV3B, AAV4, and AAV6 are reportedly about 89-93% identical (see Bantel-Schaal et al., *J. Virol.,* 73(2):939 (1999)). It has been reported that AAV serotypes 2, 3A, 3B. and 6 share about 82% total nucleotide sequence identity at the genome level (Bantel-Schaal et al., supra). Moreover, the rep sequences and ITRs of many AAV serotypes are known to efficiently cross-complement (e.g., functionally substitute) corresponding sequences from other serotypes during production of AAV particles in mammalian cells.

Generally, the cap proteins, which determine the cellular tropicity of the AAV particle, and related cap protein-encoding sequences, are significantly less conserved than Rep genes across different AAV serotypes. In view of the ability Rep and ITR sequences to cross-complement corresponding sequences of other serotypes, the AAV vector can comprise a mixture of serotypes and thereby be a 'chimeric' or 'pseudotyped' AAV vector. A chimeric AAV vector typically comprises AAV capsid proteins derived from two or more (e.g., 2, 3, 4, etc.) different AAV serotypes. In contrast, a pseudotyped AAV vector comprises one or more ITRs of one AAV serotype packaged into a capsid of another AAV serotype. Chimeric and pseudotyped AAV vectors are further described in, for example, U.S. Pat. No. 6,723,551; Flotte, *Mol. Ther.,* 12(1):1 (2006); Gao et al., *J. Virol.,* 78:6381 (2004); Gao et al., *Proc. Natl. Acad. Sci. USA,* 23:11854 (2002); De et al., *Mol. Ther.,* 12:67 (2006); and Gao et al., *Mol. Ther.,* 12:77 (2006).

In one embodiment, the AAV vector is generated using an AAV that infects humans (e.g., AAV2). Alternatively, the AAV vector is generated using an AAV that infects non-human primates, such as, for example, the great apes (e.g., chimpanzees). Old World monkeys (e.g., macaques) and New World monkeys (e.g., marmosets). In one embodiment, the AAV vector is generated using an AAV that Infects a non-human primate pseudotyped with an AAV that infects humans. Examples of such pseudotyped AAV vectors are disclosed in, e.g., Cearley et al., *Molecular Therapy.* 12:528 (2006). In one embodiment, an AAV vector can be generated which comprises a capsid protein from an AAV that infects rhesus macaques pseudotyped with AAV2 inverted terminal repeats (ITRs). In a particular embodiment, the AAV vector comprises a capsid protein from AAV10 (also referred to as "AAVrh.10"), which infects rhesus macaques pseudotyped with AAV2 ITRs (see. e.g., Watanabe et al., *Gene Ther.,* 17(8):1042 (2010); and Mao et al., *Hum. Gene Therapy.* 221525 (2011)).

In addition to the nucleic acid sequence encoding an antibody against eosinophils, or an antigen-binding fragment thereof, the AAV vector may comprise expression control sequences, such as promoters, enhancers, polyadenylation signals, transcription terminators, internal ribosome entry sites (IRES), and the like, that provide for the expression of the nucleic acid sequence in a host cell. Exemplary expression control sequences are known in the art and described in, for example, Goeddel, Gene Expression Technology. Methods in Enzymology. Vol. 185. Academic Press. San Diego. CA (1990).

A large number of promoters, including constitutive, inducible, and repressive promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-Uniting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system (U.S. Pat. Nos. 5,464,758 and 5,814,618), the Ecdysone inducible system (No et al., *Proc. Natl. Acad. Sci., J*2:3346 (1996)), the T-REX™ system (Invitrogen, Carlsbad, CA), LACSWITCH™ System (Stratagene, San Diego, CA), and the Cre-ERT tamoxifen inducible recombinase system (Indra et al., *Nuc. Acid. Res.,* 22:4324 (1999); *Nuc. Acid. Res.,* 28:e99 (2000); U.S. Pat. No. 7,112,715; and Kramer & Fuseenegger, *Methods Mol. Bid.,* 308:123 (2005)).

The term "enhancer" as used herein, refers to a DMA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DMA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. In one embodiment, the nucleic acid sequence encoding an antibody against eosinophils, or an antigen-binding fragment thereof, is operably linked to a CMV enhancer/chicken beta-actin promoter (also referred to as a "CAG promoter") (see, e.g., Niwa et al., *Gene,* 106:193 (1991); Daly et al., *Proc. Natl. Acad. Sci. U.S.A.,* 362296 (1999): and Sondhi et al., *Mol. Ther.,* 15:481 (2007)).

Typically AAV vectors are produced using well characterized plasmids. For example, human embryonic kidney 293T cells are transfected with one of the transgene specific plasmids and another plasmid containing the adenovirus helper and AAV rep and cap genes (specific to AAVrh.10, 8 or 9 as required). After 72 hours, the cells are harvested and the vector is released from the cells by five freeze/thaw cycles. Subsequent centrifugation and berizonase treatment removes cellular debris and unencapsidated DNA. Iodixanol gradients and ion exchange columns may be used to further purify each AAV vector. Next the purified vector is concentrated by a size exclusion centrifuge spin column to the required concentration. Finally, the buffer is exchanged to create the final vector products formulated (for example) in 1× phosphate buffered saline. The viral titers may be measured by TaqMan® real-time PCR and the viral purity may be assessed by SDS-PAGE.

Pharmaceutical Compositions and Delivery

The disclosure provides a composition comprising, consisting essentially of, or consisting of the above-described gene therapy vector and a pharmaceutically acceptable (e.g., physiologically acceptable) carrier. When the composition consists essentially of the gene therapy vector and a pharmaceutically acceptable carrier, additional components can be included that do not materially affect the composition (e.g., adjuvants, buffers, stabilizers, anti-inflammatory agents, solubilizers, preservatives, etc.). When the composition consists of the gene therapy vector and the pharmaceutically acceptable earner, the composition does not comprise any additional components. Any suitable carrier can be used within the context of the disclosure, and such carriers are well known in the art. The choice of carrier will be determined, in part, by the particular site to which the composition may be administered and the particular method used to administer the composition. The composition optionally can be sterile with the exception of the gene therapy vector described herein. The composition can be frozen or lyophilized for storage and reconstituted in a suitable sterile carrier prior to use. The compositions can be generated in accordance with conventional techniques described in, e.g., *Remington: The Science and Practice of Pharmacy*, 21st Edition, Lippincott Williams & Wilkins, Philadelphia, PA (2001).

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. In one embodiment, the carrier is a buffered saline solution. In one embodiment, the gene therapy vector is administered in a composition formulated to protect the gene therapy vector from damage prior to administration. For example, the composition can be formulated to reduce loss of the gene therapy vector on devices used to prepare, store, or administer the gene therapy vector, such as glassware, syringes, or needles. The composition can be formulated to decrease the light sensitivity and/or temperature sensitivity of the gene therapy vector. To this end, the composition may comprise a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the gene therapy vector, facilitate administration, and increase the efficiency of the method. Formulations for gene therapy vector-containing compositions are further described in, for example, Wright et al., *Curr. Opin Drug Discov. Devel.*, 6(2): 174-178 (2003) and Wright et al., *Molecular Therapy*, 12: 171-178 (2005))

The composition also can be formulated to enhance transduction efficiency. In addition, one of ordinary skill in the art will appreciate that the gene therapy vector can be present in a composition with other therapeutic or biologically-active agents. For example, factors that control inflammation, such as ibuprofen or steroids, can be part of the composition to reduce swelling and inflammation associated with in vivo administration of the gene therapy vector. Immune system stimulators or adjuvants, e.g., interleukins, lipopolysaccharide, and double-stranded RNA, can be administered to enhance or modify the anti-eosinophil immune response. Antibiotics, i.e., microbicides and fungicides, can be present to treat existing infection and/or reduce the risk of future infection, such as infection associated with gene therapy procedures.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In certain embodiments, a formulation comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

The composition can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the gene therapy vector. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

Delivery of the compositions comprising the gene therapy vectors may be intracerebral (including but not limited to intraparenchymal, intraventricular, or intracisternal), intrathecal (including but not limited to lumbar or cisterna magna), or systemic, including but not limited to intravenous, or any combination thereof, using devices known in the art. Delivery may also be via surgical implantation of an implanted device.

The dose of the gene therapy vector in the composition administered to the mammal will depend on a number of factors, including the size (mass) of the mammal, the extent of any side-effects, the particular route of administration, and the like. In one embodiment, the method comprises administering a "therapeutically effective amount" of the composition comprising the gene therapy vector described herein. A "therapeutically effective amount" refers to an amount effective, at dosages and for periods of time necessary, to achieve a desired therapeutic result. The therapeutically effective amount may vary according to factors such as the extent of eosinophil associated pathology, age, sex, and weight of the individual, and the ability of the gene therapy vector to elicit a desired response in the individual. The dose of gene therapy vector in the composition required to achieve a particular therapeutic effect typically is administered in units of vector genome copies per cell (gc/cell) or vector genome copies/per kilogram of body weight (gc/kg). One of ordinary skill in the art can readily determine an appropriate gene therapy vector dose range to treat a patient having a particular disease or disorder, based on these and other factors that are well known in the art. The therapeutically effective amount may be between $1 \times 10^{10}$ genome copies to $1 \times 10^{13}$ genome copies. The therapeutically effective amount may be between $1 \times 10^{11}$ genome copies to $1 \times 10^{14}$ genome copies. The therapeutically effective amount may be between $1 \times 10^{12}$ genome copies to $1 \times 10^{15}$ genome copies. The therapeutically effective amount may be between $1\times10^{13}$ genome copies to $1\times10^{16}$ genome copies.

In one embodiment, the composition is administered once to the mammal. It is believed that a single administration of the composition will result in persistent expression of the anti-eosinophil antibody in the mammal with minimal side effects. However, in certain cases, it may be appropriate to administer the composition multiple times during a therapeutic period to ensure sufficient exposure of cells to the composition. For example, the composition may be administered to the mammal two or more times (e.g., 2, 3, 4, 5, 8, 6, 8, 9, or 10 or more times) during a therapeutic period.

The present disclosure provides pharmaceutical acceptable compositions which comprise a therapeutically-effective amount of gene therapy vector comprising a nucleic acid sequence which encodes an antibody that binds to a ligand on eosinophils or that binds a molecule, the presence of which in the mammal, increases the number of eosinophils as described above.

Diseases and Disorders Amenable to Anti-Eosinophilic Gene Therapy

The gene therapy vectors described herein may be employed to prevent, inhibit or treat intrinsic or extrinsic eosinophilic disorders, e.g., those that are generally the result of genetic mutations in the eosinophilic lineage or those due to the production of eosinopoietic factors derived from T cells or tumor cells. Extrinsic diseases or disorders include but are not limited to T-cell-Mediated eosinophilias, e.g., allergic diseases including allergic rhinoconjunctivitis, bronchial asthma, and atopic dermatitis, drug hypersensitivity, e.g., Drug Rash with Eosinophilia and Systemic Symptoms (DRESS). Stevens-Johnson syndrome (SJS), and toxic epidermal necrolysis (TEN), acute bacterial or viral infections, e.g., respiratory syncytial virus (RSV), helminthic parasitic infections and Aspergillosis and coccidioidomycosis, autoimmune diseases, e.g., primary biliary cirrhosis, systemic sclerosis, dermatomyositis, systemic lupus, and Sjögren's syndrome. Dermatologic conditions such as pemphigoid, pemphigus, epidermolysis and autoimmune progesterone dermatitis, Immunodeficiency, graft versus host disease, mastocytosis, eosinophilic esophagitis, eosinophilic gastritis and gastroenteritis eosinophilic colitis; pulmonary eosinophilia, e.g., simple pulmonary eosinophilia chronic eosinophilic pneumonia, acute eosinophilic pneumonia, allergic bronchopulmonary aspergillosis and pulmonary eosinophilia associated with Churg-Strauss Syndrome and hyper-eosinophilic syndrome; T-cell-derived tumors have been associated with eosinophilia. These include Sézary syndrome, T-cell lymphoblastic lymphoma and T cell leukemia/lymphoma, Langerhans cell histiocytosis B-cell tumors also have been associated with eosinophilia. Indeed, the characteristic Reed-Sternberg cells present in Hodgkin's lymphoma; and a lymphoproliferative form of eosinophilia has been described due to clonal expansions of $CD4^+$ Th2-like lymphocytes elaborating IL-5.

In one embodiment, the disease or disorder is associated with intrinsic production of eosinopoietic factors including but are not limited to chronic eosinophilic leukemia chronic myeloid leukemia with eosinophilia, myeloproliferative disorders associated with polycythemia vera, or essential thrombocythemia idiopathic hypereosinophilic syndrome in whom no chromosomal rearrangement has been found. Other disorders include but are not limited to X-linked hypereosinophilic syndrome, familial hypereosinophilia and episodic angioedema with eosinophilia eosinophilic panniculitis, Kimura's disease, and angiolymphoid hyperplasia with eosinophilia, eosinophilic fascitis. Wells' syndrome or eosinophilic cellulitis, eosinophilic pustular folliculitis, and recurrent cutaneous necrotizing eosinophilic vasculitis.

In one embodiment, the disease or disorder is an infectious disease, e.g., parasitic infections such as helminth infection or fungal infections such as Coccidiomyces infection and allergic bronchopulmonary aspergillosis, or infestations resulting in scabies or myiasis, an allergic or atopic disease, e.g., associated with drug hypersensitivities, gastroenteritis, esophagitis, a hepatobiliary disease, meningitis, a cardiac disorder, a genitourinary disorder, an immunodeficiency, an endocrinological disorder, a pulmonary disorder, a skin disease, rheumatoid arthritis, vasculitis, or cancer, e.g., hypereosinophilic syndrome. In one embodiment, the disease or disorder is an infectious disease, e.g., a parasitic infection, a fungal infection (e.g., allergic bronchopulmonary aspergillosis or Coccidiomycosis), hematologic or neoplastic disorder, e.g., hypereosinophilic syndromes (HES) including chronic eosinophilic leukemia, leukemia (e.g., acute myelogenous leukemias most commonly, B cell ALL), lymphomas (e.g., Hodgkin's, T- and B-cell lymphomas), CML, AML, ASM, MDS, JAK2 V617F, myeloid neoplasia with abnormalities in PDGFRA, PDGRFB or FGFR1, or tumor associated adenocarcinomas, squamous carcinomas, large cell lung carcinoma, transitional cell carcinoma of the bladder, or systemic mastocytosis, immunologic disorders such as primary Immunodeficiency diseases (e.g. hyperIgE syndrome, Omenn's syndrome, Docks deficiency, IPEX, or Zap70 deficiency) or graft-versus-host-disease, an endocrinologic disorder, e.g., hypoadrenalism, or eosinophilia associated with irradiation, atheroembolic disorders or sarcoidosis. Helminth infections associated with eosinophilia include but are not limited to angiostrongyloidiasis, ascariasis, clonorchiasis, fascioliasis, fasciolopsiasis, filarial infections, lymphatic filariasis, *Brugia, Wuchereria, Loa loa, Mansonella ozzardi, Mansonella perstans, Mansonella streptocerca, Onchocerca volvulus*, tropical pulmonary eosinophilia gnathostomiasis, hookworm, opisthorchiasis, paragonimiasis, schistosomiasis, *Schistosoma haematobium, Schistosoma inlercalatum, Schistosoma japonicum, Schistosoma mansoni, Schistosoma mekongi*, strongyloidiasis, trichinosis, visceral larva migrans, *Toxocara canis; T catis*, or *Baylisascaris procyonis*.

Diseases or disorders with organ restricted involvement and marked peripheral eosinophils that may be prevented, inhibited or treated with the gene therapy vector described herein include but are not limited to skin and subcutaneous diseases, e.g., episodic angioedema with eosinophilia, eosinophilic cellulitis (Well's syndrome), eosinophilic panniculitis, angiolymphoid hyperplasia with eosinophilia (and Kimura's Disease), eosinophilic pustular dermatitis or cutaneous necrotizing eosinophilic vasculitis, pulmonary diseases, e.g., drug- and toxin-induced eosinophilic lung diseases, helminth associated (Loeffler's syndrome; tropical pulmonary eosinophilia), chronic eosinophilic pneumonia, acute eosinophilic pneumonia, Churg-Strauss syndrome, or other vasculitides, gastrointestinal diseases, e.g., eosinophilic gastrointestinal disorders (EGIDs) including but not limited to eosinophilic esophagitis (EE) and eosinophilic gastroenteritis (EG), primary biliary cirrhosis, sclerosing cholangitis, eosinophilic cholangitis, or eosinophilic cholecystitis, neurologic diseases including but not limited to eosinophilic meningitis, ventriculoperitoneal shunts, leukemia or lymphoma with CNS involvement (Hodgkin s), nonsteroidal antiinflammatory drugs, antibiotics, contrast agents, rheumatologic diseases, Churg-Strauss syndrome, eosinophilia-myalgia syndrome, cardiac diseases including but not limited to hypersensitivity myocarditis or Churg- Strauss syndrome, or genitourinary disease, e.g., drug induced interstitial nephritis or eosinophilic cystitis.

In one embodiment the disease or disorder is an infectious disease including but not limited to infections with helminth (worm) parasite, intestinal coccidian *Isospora belli, Dientamoeba fragilis, Sarcocystis hominis*, ectoparasites, e.g., scabies, fly larvae (myiasis), HIV, fungi, e.g., coccidiomycosis and aspergillosis In one embodiment the disease or disorder is an atopic/allergic disease, e.g., allergic rhinitis, non-allergic rhinitis with eosinophilia syndrome (NARES or BENAR), or asthma (both allergic and nonallergic).

In one embodiment the disease or disorder is medication-associated peripheral blood eosinophilia, e.g., associated with quinine, penicillins, cephalosporins, quinolones, NSAIDs, sulfas, nitrofurantoin, tetracyclines, semisynthetic penicillins, amiodarone, nitrofurantoin, methotrexate, SSRIs or SNRIs cephalosporins (e.g., cefotaxime, cefoxitin, cefoperazone, or cefotriaxone), sulfasalazine, hydantoin, carbamazepine, d-penicillamine, allopurinol, hydrochlorothiazide, cyclosporine, ranitidine, GM-CSF, IL-2, phenytoin, allopurinol, aspirin, nevaripine, or sulfasalazine.

In one embodiment the disease or disorder is a hematologic/neoplastic disease including but not limited to lymphoid malignancies, e.g., Hodgkin's disease, primary cutaneous T-cell lymphoma or Sezary syndrome, solid tumors, e.g., lymphomas, large-cell nonkeratinizing cervical tumors, large-cell undifferentiated king carcinomas, squamous carcinomas of the lung, vagina, penis, skirt or nasopharynx, adenocarcinomas of the stomach, large bowel, or uterine body, or transitional cell carcinoma of the bladder, or mastocytosis.

In one embodiment the disease or disorder is an immunodeficiency, e.g., Omenn syndrome HyperIgE (Job's) syndrome, Docks deficiency. IP EX, or Zap70 deficiency, or graft-versus-host disease (GVHD), e.g., following allogeneic stem cell transplantation.

In one embodiment, the disease or disorder is an endocrine disease or disorder, e.g., as a result of loss of endogenous adrenoglucocorticosteroids in Addison's disease adrenal hemorrhage, or hypopituitarism.

In one embodiment, the disease or disorder is associated with cholesterol embolization, eosinophilic, polymorphic, and pruritic eruption associated with radiotherapy (EPPER), sarcoidosis, inflammatory bowel disease or other disorders associated with immune-dysregulation.

In one embodiment, the disease or disorder is hypereosinophilia with organ-restricted involvement, e.g., skin and subcutaneous tissue disease such as atopic and blistering diseases. e.g., atopic dermatitis blistering diseases, such as bullous pemphigoid, pemphigus vulgaris, dermatitis herpetiformis, herpes gestation, disorder characterized by the association of nodules, eosinophilia, rheumatism, dermatitis, and swelling (NERDS), eosinophilic panniculitis, e.g., contact dermatitis, eosinophilic cellulitis, arthropod bites, toxocariasis, polyarteritis nodosa, injection granuloma, lupus panniculitis, malignancy, diabetes, chronic recurrent parotitis, episodic angioedema with eosinophilia, Kimura's Disease, angiolymphoid hyperplasia with eosinophilia, eosinophilic fasciitis, Wells' syndrome (eosinophilic cellulitis), or eosinophilic pustular folliculitis.

Other hypereosinophilias with organ-restricted involvement include pulmonary disease or disorders, e.g., chronic eosinophilic pneumonia or acute eosinophilic pneumonia; gastrointestinal disease, e.g., eosinophilic gastrointestinal diseases (EGID) such as eosinophilic esophagitis (EoE) or eosinophilic gastroenteritis; hepatobiliary diseases such as primary biliary cirrhosis, sclerosing cholangitis, eosinophilic cholangitis or eosinophilic cholecystitis; neurologic disease including eosinophilic meningitis, e.g., due to central nervous system infections, ranging from fungal to helminthic (e.g. coccidioidomycosis or *Angiostrongylus cantonensis* infection), as well as to adverse drug reactions to NSAIDs or antibiotics; rheumatologic diseases such as dermatomyositis, rheumatoid arthritis, systemic sclerosis, or Sjögren's syndrome, eosinophilia-myalgia syndrome or toxic oil syndrome, vasculitis, e.g., Churg-Strauss syndrome (CSS), cutaneous necrotizing vasculitis, thromboangiitis obliterans with eosinophilia of the temporal arteritis; cardiac diseases that result in damage to the endomyocardium that can occur with hypersensitivity myocarditis, with eosinophilias associated with eosinophilic leukemia, sarcomas, carcinomas, or lymphomas, with GM-CSF or IL-2 administration, with prolonged drug-induced eosinophilia, or with parasitic infections; genitourinary diseases including interstitial nephritis with eosinophilia is typically drug-induced semisynthetic penicillins, cephalosporins, NSAIDs, allopurinol, rifampin, and ciprofloxacin, frequency, hematuria, dysuria or suprapubic pain.

Table 1 provides exemplary diseases or disorders associated with eosinophilia

TABLE 1

| Condition | Description |
| --- | --- |
| Infectious diseases | |
| Parasitic conditions | Strongyloidiasis, liver fluke, hydatid disease, filariasis, schistosomiasis |
| Fungal infections | Allergic bronchopulmonary aspergillosis, coccidiomycosis |
| Infestations | Scabies, myiasis |
| Allergic or atopic diseases | |
| Atopic disorders | Asthma, urticarial, allergic rhinitis |
| Drug hypersensitivity or medication associated eosinophilia | Aspirin, cephalosporin, penicillin, nitrofurantoin, iodides, sulfonamides |
| Gastrointestinal/hepatic | |
| Eosinophilic esophagitis | |
| Eosinophilic gastroenteritis | |
| Hepatobiliary diseases | Eosinophilic hepatitis, primary biliary cirrhosis, sclerosing cholangitis, eosinophilic cholecystitis |

TABLE 1-continued

| Condition | Description |
|---|---|
| Hematological and neoplastic disorders | |
| Hypereosinophilic syndromes (HES) | including chronic eosinophilic leukemia acute |
| Leukemia | lymphoblasatic leukemia, acute myelogenous leukemia, chronic myelogenous leukemia, T- and B-cell leukemias |
| Lymphomas | Hodgkin's lymphoma, T- and B-cell lymphomas |
| Stem cell neoplasm | Myelodysplastic syndrome, myeloproliferative neoplasm |
| Tumor associated (solid tumors/malignancy) | Adenocarcinomas, squamous carcinomas, large cell carcinomas, transitional cell carcinoma of bladder, systemic mastocytosis |
| Neurologic | |
| Eosinophilic meningitis | |
| Cardiac | |
| Hypersensitivity myoacrditis | |
| Eosinophilic leukemia, sarcoma, carcinoma, lymphoma | |
| Genitourinary | |
| Interstitial nephritis, eosinophilic cystitis | |
| Immunologic | |
| Primary immunodeficiency diseases: | HyperIgE syndrome, Omenn's syndrome, Dock 8 deficiency, IPEX, Zap 70 deficiency |
| Other | Graft-versus-host disease, |
| Endocrinologic disorders | |
| Hypoadrenalism | Adrenal hemorrhage, loss of endogenous adrenoglucocorticosteroids. hypopituitarism |
| Pulmonary disorders | |
| Chronic/acute eosinophilic pneumonia | |
| Eosinophilic asthma | |
| Skin diseases | |
| Pemphigus, dermatitis herpetiformis Erythema multiforme, episodic angioedema with eosinophilia, eosinophilic panniculitis, Kimua's disease, eosinophilic fasciitis, Wells' syndrome, eosinophilic pustular folliculitis | |
| Rheumatologic/Vasculitis | |
| Rheumatoid arthritis, eosinophilic fasciitis, allergic angiitis, eosinophilia-myalgia syndrome, Churg-Strauss syndrome, | |
| Other | |
| Irradiation, atheroembolic disorders, sarcoidosis, chronic inflammatory disorders, e.g., IBD | |

Exemplary Antibodies

The gene therapy vector may encode one or more antibody sequences including but not Smiled to a sequence for an anti-IL-5 or IL-5R antibody, e.g., mepolizumab, reslizumab, benralizumab, or MEDI-563, anti-CD52 antibody, e.g., alerntuzumab, anti-IL-4R antibody, anti-CCR3 antibody, anti-IL-13 or IL-13R antibody, anti-CD30 antibody, anti-IL-17 or IL-17R antibody, anti-RADCP antibody (see US 20030099995), anti IgE antibody. e.g., omalizumab, anti-CD52 antibody, anti-IL-4 antibodies, anti IL-33 or IL-33R antibody, anti-IL-9 or IL-9R antibody, anti-TNF-alpha antibody, e.g., infliximab, anti-eotaxin antibody, or anti-sialoadhesion factor or anti-sialoadhesion factor receptor antibody.

Exemplary antibody sequences e.g., variable region sequences include but are not limited to antibodies comprising a polypeptide comprising sequences having at least 80%, 82%, 84%, 85%, 87%, 89%, 90%, 92%, 94%, 95%, 97%, 98%, or 99% amino acid sequence identity to a polypeptide encoded by one of SEQ ID No. 1 or 2, or a polypeptide comprising sequences having at least 80%, 82%, 84%, 85%, 87%, 89%, 90%, 92%, 94%, 95%, 97%, 98% or 99% amino acid sequence identity to any one of SEQ ID Nos. 3-6, 8-32, 40-41, 43-44, or 46-51, e.g., in framework regions one or more CDRs, or both, in one of SEQ ID Nos. 3-6, 8-32, 40-41, 43-44, or 46-51 (see below).

Anti-Siglec-F (SEQ ID NO: 1)
ATGGCTGTCCTGGTGCTGTTGCTCTGCCTGCTGACATTTCCAAGCTGTGTC

CTGTCCCAGGTGCAGCTGAAGGAGTCAGGACCTGGTCTGGTGCAGCCCTCA

CAGACTTTGTCTCTCACCTGCACTGTCTCTGGGTTCTCACTAGCCAGCTAT

CATGTAAGCTGGGTTCGCCAGCCTCCAGGAAAAGGTCTGGAGTGGATGGGA

-continued
CTAATATGGACTGGTGGAAGCACAACATATAATTCACTTCTCAAATCCCGA

CTGAGCATCAGCAGGGACACCTCCAAGAGCCAAGTTTTCCTAAAGATGAAC

AGTCTGCAAACTGAAGACACAGCCACTTACTACTGTGCCAGAGTTGGGGGA

GGGAATAGTGCGCTATACTTTGATTATTGGGGCCAAGGAGTCATGGTCACA

GTCTCCTCA (SEQ ID NO: 2)
GACATCCAGATGACACAGTCTCCAGCTTCCCTGTCTGCATCTCTGGGAGAA

ACTGTCACCATCGAATGTCGAGCAAGTGAGGACATTTACACCGGTTTAGCA

TGGTATCACCAGAAGCCAGGGAAATCTCCTCAACTCCTGATCTATAATGCA

AATAGCTTGCAGTCTGGGGTCCCATCACGGTTCAGTGGCAGTGGATCTGGT

ACACAGTATTCTCTCAAGATAAACAGCCTGCAGTCTGAAGATGTCGCAAGT

TATTTCTGTCAACAGTATTACAATTATCCGCTCACGTTCGGTTCTGGGACC

AAGCTGGAGATCAAACGG

SEQ ID Nos. 3-4 are as follows:
 1 mesqtqvlms lllwlsgtcq divmtqspss lavsagetvt
   inckssqsll ysgnqknyla 61 wyqqkpgqsp kiliswastr qsgvpdrfig sgsgtdftlt
   issvqaedla iyycqqnfdt 21 pptfgsgtkl eikradaapt vsifppsteq latggasvvc
   lmnnfyprdi svkwkidgte 81 rrdgvldsvt dqdskdstys msstlsltka dyeshnlytc
   evvhktsssp vvksfnrrnec 1 agttapavyp lapgcgdtts stvtlgclvk gyfpepvtvt
   wnagalssdv htfpavlqsg 61 lytltssvts stwpsqtvtc nvahpasstk vdkkverrng
   gighkcptcp tchkcpvpel 21 lggpsvfifp pkpkdillis qnakvtcvvv dvseeepdvq
   fswfvnnvev htaqtqpree 81 qynstfrvvs alpiqhgdwm sgkefkckvn nkalpsplek
   tiskpkglvc kpqvyvmgpp 41 teqlteqtvs ltcltsgflp ndigvewtsn ghiekoyknt
   epvmdsdgsf fmysklnver 01 srwdsrapfv csvvheqlhn hhveksisrp pgk (SEQ ID NO: 5)
Glu Val Gln Leu Val Glu Ser Gly Gly Gly Leu Val Gln Pro Gly Gly Ser Leu Arg Leu Ser Cys Ala Ala Ser Gly Phe Ser Leu Thr Ile Tyr Gly Ala His Trp Val Arg Gln Ala Pro Gly Lys Gly Leu Glu Trp Val Gly Val Ile Trp Ala Gly Gly Ser Thr Asn Tyr Asn Ser Ala Leu Met Ser Arg Phe Thr Ile Ser Lys Asp Asn Ser Lys Asn Thr Val Tyr Leu Gln Met Asn Ser Leu Arg Ala Glu Asp Thr Ala Val Tyr Tyr Cys Ala Arg Asp Gly Ser Ser Pro Tyr Tyr Tyr Ser Met Glu Tyr Trp Gly Gln Gly Thr Thr Val Thr Val Ser Ser (SEQ ID NO: 6)
Gln Ile Val Leu Thr Gln Ser Pro Ala Thr Leu Ser Leu Ser Pro Gly Glu Arg Ala Thr Leu Ser Cys Ser Ala Thr -continued
Ser Ser Val Ser Tyr Met His Trp Phe Gln Gln Lys Pro Gly Gln Ala Pro Arg Leu Leu Ile Tyr Ser Thr Ser Asn Leu Ala Ser Gly Ile Pro Ala Arg Phe Ser Gly Ser Gly Ser Gly Thr Asp Phe Thr Leu Thr Ile Ser Ser Leu Glu Pro Glu Asp Phe Ala Val Tyr Tyr Cys Gln Gln Arg Ser Ser Tyr Pro Phe Thr Phe Gly Pro Gly Thr Lys Leu Asp Ile Lys (SEQ ID NO: 7)
Ala Ser Thr Lys Gly Pro Ser Val Phe Pro Leu Ala Pro Ser Ser Lys1 Ser Thr Ser Gly Gly Thr Ala Ala Leu Gly Cys Leu Val Lys Asp Tyr Phe Pro Glu Pro Val Thr Val Ser Trp Asn Ser Gly Ala Len Thr Ser Gly Val His Thr Phe Pro Ala Val Leu Gln Ser Ser Gly Leu Tyr Ser Leu Ser Ser Val Val Thr Val Pro Ser Ser Ser Leu Gly Thr Gln Thr Tyr Ile Cys Asn Val Asn His Lys Pro Ser Asn Thr Lys Val Asp Lys Arg Val Glu Pro Lys Ser Cys Asp Lys Thr His Thr Cys Pro Pro Cys Pro Ala Pro Glu Leu Leu Gly Gly Pro Ser Val Phe Leu Phe Pro Pro Lys Pro Lys Asp Thr Leu Met Ile Ser Arg Thr Pro Glu Val Thr Cys Val Val Val Asp Val Ser His Glu Asp Pro Glu Val Lys Phe Asn Trp Tyr Val Asp Gly Val Glu Val His Asn Ala Lys Thr Lys Pro Arg Glu Glu Gln Tyr Asn Ser Thr Tyr Arg Val Val Ser Val Leu Thr Val Leu His Gln Asp Trp Leu Asn Gly Lys Glu Tyr Lys Cys Lys Val Ser Asn Lys Ala Leu Pro Ala Pro Ile Glu Lys Thr Ile Ser Lys Ala Lys Gly Gln Pro Arg Glu Pro Gln Val Tyr Thr Leu Pro Pro Ser Arg Glu Glu Met Thr Lys Asn Gln Val Ser Leu Thr Cys Leu Val Lys Gly Phe Tyr Pro Ser Asp Ile Ala Val Glu Trp Glu Ser Asn Gly Gln Pro Glu Asn Asn Tyr Lys Thr Thr Pro Pro Val Leu Asp Ser Asp Gly Ser Phe Phe Leu Tyr Ser Lys Leu Thr Val Asp Lys Ser Arg Trp Gln Gln Gly Asn Val Phe Ser Cys Ser Val Met His Glu Ala Leu His Asn His Tyr Thr Gln Lys Ser Leu Ser Leu Ser Pro Gly (SEQ ID NO: 8)
Arg Thr Val Ala Ala Pro Ser Val Phe Ile Phe Pro Pro Ser Asp Glu Gln Leu Lys Ser Gly Thr Ala Ser Val Val Cys Leu Leu Asn Asn Phe Tyr Pro Arg Glu Ala Lys Val Gln Trp Lys Val Asp Asn Ala Leu Gln Ser Gly Asn Ser Gln Glu Ser Val Thr Glu Gln Asp Ser Lys Asp Ser Thr Tyr Ser Leu Ser Ser Thr Leu Thr Leu Ser Lys Ala Asp Tyr Glu65 Lys His Lys Val Tyr Ala Cys Glu Val Thr -continued

```
His Gln Gly Leu Ser Ser Pro Val Thr Lys Ser Phe Asn

Arg Gly Glu Cys
```

Anti-Siglec antibody sequences in Table 2, e.g., SEQ ID Nos. 9-32, 40-41, 4-44, or 46-51, which may include heavy or light chain sequences from any one of SEQ ID Nos. 7, 33-39, 42, or 45. Including antibodies that are specific for any one of SEQ ID Nos.52-59.

```
                                                             (SEQ ID NO: 9)
QVQLKESGPGLVAPSQSLSITCTVSGFSLTIYGAHWVRQPPGKGLEWLGVIWAGGSTNYNSALMSRLSIS

KDNSKSQVFLKINSLQTDDTALYYCARDGSSPYYYSMEYWGQGTSVTVSS (SEQ ID NO: 10)
EVQLVESGGGLVCPGGSLRLSCAASGFSLTIYGAHWVRQAPGKGLEVWSVIWAGGSTNYNSALMSRFTI

SKDNSKNTVYLQMNSLRAEDTAVYYCARDGSSPYYYSMEYWGQGTTVTVSS (SEQ ID NO: 11)
EVQLVESGGGLVQPGGSLRLSCAVSGFSLTIYGAHWVRQAPGKGLEWLGVIWAGGSTNYNSALMSRLSI

SKDNSKNTVYLQMNSLRAEDTAVYYCARDGSSPYYYSMEYWGQGTTVTVSS (SEQ ID NO: 12)
EVQLVESGGGLVQPGGSLRLSCAVSGFSLTIYGAHWVRQAPGKGLEWVSVIWAGGSTNYNSALMSRFTI

SKDNSKNTVYLQMNSLRAEDTAVYYCARDGSSPYYYSMEYWGQGTTVTVSS (SEQ ID NO: 13)
EVQLVESGGGLVQPGGSLRLSCAASGFSLTIYGAHWVRQAPGKGLEWLSVIWAGGSTNYNSALMSRFTI

SKDNSKNTVYLQMNSLRAEDTAVYYCARDGSSPYYYSMEYWGQGTTVTVSS (SEQ ID NO: 14)
EVQLVESGGGLVQPGGSLRLSCAASGFSLTIYGAHWVRQAPGKGLEWVGVIWAGGSTNYNSALMSRFTI

SKDNSKNTVYLQMNSLRAEDTAVYYCARDGSSPYYYSMEYWGQGTTVTVSS (SEQ ID NO: 15)
EVQLVESGGGLVQPGGSLRLSCAASGFSLTIYGAHWVRQAPGKGLEWVSVIWAGGSTNYNSALMSRLTI

SKDNSKNTVYLQMNSLRAEDTAVYYCARDGSSPYYYSMEYWGQGTTVTVSS (SEQ ID NO: 16)
EVQLVESGGGLVQPGGSLRLSCAASGFSLTIYGAHWVRQAPGKGLEWVSVIWAGGSTNYNSALMSRFSI

SKDNSKNTVYLQMNSLRAEDTAVYYCARDGSSPYYYSMEYWGQGTTVTVSS (SEQ ID NO: 17)
QVQLQESGPGLVKPSETLSLTCTVSGGSISIYGAHWIRQPPGKGLEWIGVIWAGGSTNYNSALMSRVTIS

VDTSKNQFSLKLSSVTAADTAVYYCARDGSSPYYYSMEYWGQGTLVTVSS (SEQ ID NO: 18)
QVQLGESGPGLVKPSETLSLTCTVSGFSLTIYGAHWVRQPPGKGLEWLGVIWAGGSTNYNSALMSRLSI

SKDNSKNQVSLKLSSVTAADTAVYYCARDGSSPYYYSMEYWGQGTLVTVSS (SEQ ID NO: 19)
EVQLVESGGGLVQPGGSLRLSCAASGFSLTIYGAHWVRQAPGKGLEWVGVIWAGGSTNYNSALMSRFTI

SKDNSKNTVYLQMNSLRAEDTAVYYCARDGSSPYYYGMEYWGQGTTVTVSS (SEQ ID NO: 20)
EVQLVESGGGLVQPGGSLRLSCAASGFSLTIYGAHWVRQAPGKGLEWVGVIWAGGSTNYNSALMSRFTI

SKDNSKNTVYLQMNSLRAEDTAVYYCARDGSSPYYYSMDYWGQGTTVTVSS (SEQ ID NO: 21)
EVQLVESGGGLVQPGGSLRLSCAASGFSLTIYGAHWVRQAPGKGLEWVGVIWAGGSTNYNSALMSRFTI

SKDNSKNTVYLQMNSLRAEDTAVYYCARDGSSPYYYSMEVWGQGTTVTVSS (SEQ ID NO: 22)
EVQLVESGGGLVGPGGSLRLSCAASGFSLTIYGAHWVRQAPGKGLEWVGVIWAGGSTNYNSALMSRFTI

SKDNSKNTVYLQMNSLRAEDTAVYYCARDGSSPYYYGMDVWGQGTTVTVSS
```

-continued (SEQ ID NO: 23)
QIILTQSPAIMSASPGEKVSITCSATSSVSYMHWFQQKPGTSPKLWIYSTSNLASGVPVRFSGSGSGTSYS
LTISRMEAEDAATYYCQQRSSYPFTFGSGTKLEIK (SEQ ID NO: 24)
EIVLTQSPATLSLSPGERATLSCSATSSVSYMHWFQQKPGQAPRLLIYSTSNLASGIPARFSGSGSGTDFT
LTISSLEPEDFAVYYCQQRSSYPFTFGPGTKLDIK (SEQ ID NO: 25)
EIILTQSPATLSLSPGERATLSCSATSSVSYMHWFQQKPGQAPRLWIYSTSNLASGVPARFSGSGSGTDY
LTISSLEPEDFAVYYCQQRSSYPFTFGPGTKLDIK (SEQ ID NO: 26)
EIILTQSPATLSLSPGERATLSCSATSSVSYMHWFQQKPGQAPRLLIYSTSNLASGIPARFSGSGSGTDFT
LTISSLEPEDFAVYYCGQRSSYPFTFGPGTKLDIK (SEQ ID NO: 27)
EIVLTQSPATLSLSPGERATLSCSATSSVSYMHWFQQKPGQAPRLWIYSTSNLASGIPARFSGSGSGTDF
TLTISSLEPEDFAVYYCQQRSSYPFTFGPGTKLDIK (SEQ ID NO: 28)
EIVLTQSPATLSLSPGERATLSCSATSSVSYMHWFQQKPGQAPRLLIYSTSNLASGVPARFSGSGSGTDF
TLTISSLEPEDFAVYYCQQRSSYPFTFGPGTKLDIK (SEQ ID NO: 2)
EIVLTQSPATLSLSPGERATLSCSATSSVSYMHWFQQKPGQAPRLLIYSTSNLASGIPARFSGSGSGTDYT
LTISSLEPEDFAVYYCQQRSSYPFTFGPGTKLDIK (SEQ ID NO: 30)
EIVLTQSPATLSLSPGERATLSCSATSSVSYMHWYQQKPGQAPRLLIYSTSNLASGIPARFSGSGSGTDFT
LTISSLEPEDFAVYYCQQRSSYPFTFGPGTKLDIK (SEQ ID NO: 31)
EIVLTQSPATLSLSPGERATLSCSATSSVSYMHWFQQKPGQAPRLLIYSTSNLASGIPARFSGSGSGTDFT
LTISSLEPEDFAVYYCQQRSSYPYTFGPGTKLDIK (SEQ ID NO: 32)
EIVLTQSPATLSLSPGERATLSCSATSSVSYMHWFQQKPGQAPRLLIYSTSNLASGIPARFSGSGSGTDYT
LTISSLEPEDFAVYYCQQRSSYPYTFGPGTKLDIK (SEQ ID NO: 33)
EVQLVESGGGLVQPGGSLRLSCAASGFSLTIYGAHWVRQAPGKGLEWVGVIWAGGSTNYNSALMSRFTI
SKDNSKNTVYLQMNSLRAEDTAVYYCARDGSSPYYYSMEYWGQGTTVTVSSASTKGPSVFPLAPSSKS
TSGGTAALGCLVKDYFPEPVTVSWNSGALTSGVHTFPAVLQSSGLYSLSSVVTVPSSSLGTQTYICNVNH
KPSNTKVDKRVEPKSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTISKAKGQP
REPQVYTLPPSREEMTKNQVSLTCLVKGFYPSDIAVEWESNGQPENNYKTTPPVLDSDGSFFLYSKLTVD
KSRWQQGNVFSCSVMHEALHNHYTQKSLSLSPG (SEQ ID NO: 34)
EIVLTQSPATSLSPGERATLSCSATSSVSYMHWFQQKPGQAPRLLIYSTSNLASGIPARFSGSGSGTDFT
LTISSLEPEDFAVYYCQQRSSYPFTFGPGTKLDIKRTVAAPSVFIFPPSDEQLKSGTASVVCLLNNFYPREA
KVQWKVDNALQSGNSQESVTEQDSKDSTYSLSSTLTLSKADYEKHKVYACEVTHQGLSSPVTKSFNRGE
C (SEQ ID NO: 35)
EIVLTQSPATLSLSPGERATLSCSATSSVSYMHWFQQKPGQAPRLLIYSTSNLASGIPARFSGSGSGTDYT
LTISSLEPEDFAVYYCQQRSSYPFTFGPGTKLDIKRTVAAPSVFIFPPSDEQLKSGTASVVCLLNNFYPREA

```
KVQWKVDNALQSGNSQESVTEQDSKDSTYSLSSTLTLSKADYEKHKVYACEVTHQGLSSPVTKSFNRGE
C (SEQ ID NO: 36)
ASTKGPSVFPLAPSSKSTSGGTAALGCLVKDYFPEPVTVSWNSGALTSGVHTFPAVLQSSGLYSLSSVVT
VPSSSLGTQTYICNVNHKPSNTKVDKRVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSREEMTKNQVSLTCLVKGFYPSDIAVEWESNGQPENNYKTPP
VLDSDGSFFLYSKLTVDKSRWQQGNVFSCSVMHEALHNHYTQKSLSLSPG (SEQ ID NO: 37)
ASTKGPSVFPLAPCSRSTSESTAALGCLVKDYFPEPVTVSWNSGALTSGVHTFPAVLQSSGLYSLSSVVT
VPSSSLGTKTYTCNVDHKPSNTKVDKRVESKYGPPCPPCPAPEFLGGPSVFLFPPKPKDTLMISRTPEVT
CVVVDVSQEDPEVQFNWYVDGVEVHNAKTKPREEQFNSTYRVVSVLTVLHQDWLNGKEYKCKVSNKGL
PSSIEKTISKAKGQPREPQVYTLPPSQEEMTKNQVSLTCLVKGFYPSDIAVEWESNGQPENNYKTTPPVL
DSDGSFFLYSRLTVDKSRWQEGNVFSCSVMHEALHNHYTQKSLSLSLG (SEQ ID NO: 38)
RTVAAPSVFIFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 39)
QVQLKRASGPGLVAPSQSLSITCTVSGFSLTIYGAHWVRQPPGKGLEWLGVIWAGGSTNYNSALMSRLSI
SKDNSKSQVFLKINSLQTDDTALYYCARDGSSPYYYSMEYWGGGTSVTVSSAKTTPPSVYPLAPGSAAQ
TNSMVTLGCLVKGYFPEPVTVTWNSGSLSSGVHTFPAVLESDLYTLSSSVTVPSSPRPSETVTCNVAHPA
SSTKVDKKIVPRDCGCKPCICTVPEVSSVFIFPPKPKDVLTITLTPKVTCVVVDISKDDPEVQFSWFVDDVE
VHTAQTQPREEQFNSTFRSVSELPIMHQDWLNGKEFKCRVNSAAFPAPIEKTISKTKGRPKAPQVYTIPPP
KEQMAKDKVSLTCMITDFFPEDITVEWQWNGQPAENYKNTQPIMNTNGSYFVYSKLNVQKSNWEAGNT
FTCSVLHEGLHNHHTEKSLSHSPG (SEQ ID NO: 40)
EIILTQSPAIMSASPGEKVSITCSATSSVSYMHWFQQKPGTSPKLWIYSTSNLASGVPVRFSGSGSGTSYS
LTISRMEAEDAATYYCQQRSSYPFTFGSGTKLEIKADAAPTVSIFPPSSEQLTSGGASVVCFLNNFYPKDIN
VKVWKIDGSERQNGVLNSWTDQDSKDSTYSMSSTLTLTKDEYERHNSYTCEATHKTSTSPIVKSFNRNEC (SEQ ID NO: 41)
QIILTQSPAIMSASPGEKVSITCSATSSVSYMHWFQQKPGTSPKLWIYSTSNLASGVPVRFSGSGSGTSYS
LTISRMEAEDAATYYCQQRSSYPFTFGSGTKLEIKADAAPTVSIFPPSSEQLTSGGASVVCFLNNFYPKDIN
VKVWKIDGSERQNGVLNSWTDQDSKDSTYSMSSTLTLTKDEYERHNSYTCEATHKTSTSPIVKSFNRNEC (SEQ ID NO: 42)
QVQLKRASGPGLVAPSQSLSITCTVSGFSLTIYGAHWVRQPPGKGLEWLGVIWAGGSTNYNSALMSRLSI
SKDNSKSQVFLKINSLQTDDTALYYCARDGSSPYYYSMEYWGQGTSVTVSSASTKGPSVFPLAPSSKST
SGGTAALGCLVKDYFPEPVTVSWNSGALTSGVHTFPAVLQSSGLYSLSSWTVPSSSLGTQTYICNVNHK
PSNTKVDKRVEPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIEKTISKAKGQPR
EPQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPG (SEQ ID NO: 43)
EIILTQSPAIMSASPGEKVSITCSATSSVSYMHWFQQKPGTSPKLWIYSTSNLASGVPVRFSGSGSGTSYS
LTISRMEAEDAATYYCQQRSSYPFTFGSGTKLEIKRTVAAPSVFIFPPSDEQLKSGTASVVCLLNNFYPRE
```

-continued

AKVQWKVDNALQSGNSQESVTEQDSKDSTYSLSSTLTLSKADYEKHKVYACEVTHQGLSSPVTKSFNRG

EC (SEQ ID NO: 44)
QIILTQSPAIMSASPGEKVSITCSATSSVSYMHWFQQKPGTSPKLWIYSTSNLASGVPVRFSGSGSTSYS

LTISRMEAEDAATYYCQQRSSYPFTFGSGTKLEIKRTVAAPSVFIFPPSDEQLKSGTASVVCLLNNFYPRE

AKVQWKVDNALQSGNSQESVTEQDSKDSTYSLSSTLTLSKADYEKHKVYACEVTHQGLSSPVTKSFNRG

EC (SEQ ID NO: 45)
EVQLVESGGGLVQPGGSLRLSCAASGFSLTIYGAHWVRQAPGKGLEWVGVIWAGGSTNYNSALMSRFTI

SKDNSKNTVYLQMNSLRAEDTAVYYCARDGSSPYYYSMEYWGQGTTVTVSSASTKGPSVFPLAPCSRS

TSESTAALGCLVKDYFPEPVTVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTPEVTCVVVDVSQEDPEVQFN

WYVDGVEVHNAKTKPREEQFNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTPPVLDSDGSFFLYSRLTVDKS

RWQEGNVFSCSVMHEALHNHYTQKSLSLSLG (underlined residues comprise CDRs H1 and H2 according to
Chothia numbering)
(SEQ ID NO: 46)
EVGVVESGGDLVKSGGSLKLSCAASGFPFSSYAMSWVRQTPDKRLEWVAIISSGGSYTYYSDSVKGRFT

ISRDNAKNTLYLQM SSLKSEDTAMYYCARHETAQAAWFAYWGQGTLVTVSA (underlined residues comprise CDRs H1 and H2 according to
Chothia numbering)
(SEQ ID NO: 47)
EVQLQQSGAELVRPGASVKLSCTASGFNIKDYYMYWVKQRPEQGLEWIGRIAPEDGDTEYAPKFQGKAT

VTADTSSNTAYLHLSSLTSEDTAVYYCTTEGNYYGSSILDYWGQGTTLTVSS (underlined residues comprise CDRs H1 and H2 according to
Chothia numbering)
(SEQ ID NO: 48)
QVQLQQSGAELVKPGASVKISCKASGYAFRSSWMNWVKQRPGKGLEWIGQIYPGDDYTNYNGKFKGKV

TLTADRSSTAYMQLSSLTSEDSAVYFCARLGPYGPFADWGQGTLVTVSA (SEQ ID NO: 49)
QIVLTQSPAIMSASPGEKVTMTCSASSSVSYMHWYQQKSGTSPKRWIYDTSKLAYGVPARFSGSGSGTS

YSLTISSMEAEDAATYYCQQWSSNPPTFGGGTKLEIK (SEQ ID NO: 50)
DIQMTQTTSSLSASLGDRVTISCRASQDITNYLNWYQQKPDGTVKLLIYFTSRLHSGVPSRFSGSGSGTD

YSLTISNLEQEDIATYFCQQGNTLPWTFGGGTKLEIK (SEQ ID NO: 51)
QIVLTQSPAIVSASPGEKVTMTCSASSSVSYMYWYQQRPGSSPRLLIYDTSSLASGVPVRFSGSGSGTSY

SLTISRIESEDAANYYCQQWNSDPYTFGGGTKLEIK (SEQ ID NO: 52)
MEGDRQGYGDGYLLQVQELVTVQEGLCVHVPCSFSYPQDGWTDSDPVHGYWFRAGDRPYQDAPVATN

NPDREVQAETQGRFQLLGDIWSNDCSLSIRDARKRDKGSYFFRLERGSMKWSYKSQLNYKTKQLSVFVT

ALTHRP (SEQ ID NO: 53)
DILILGTLESGHSRNLTCSVPWACKQGTPPMISWIGASVSSPGPTTARSSVLTLTPKPQDHGTSLTCQVTL

PGTGVTTTSTVRLDVS (SEQ ID NO: 54)
YPPWNLTMTVFQGDATASTALGNGSSLSVLEGQSLRLVCAVNSNPPARLSWTRGSLTLCPSRSSNPGLL

ELPRVHVRDEGEFTCRAQNAQGSQHISLSLSLQNEGTGTSRPVSQVTLAAVGG

```
                                                          (SEQ ID NO: 55)
MEGDRQYGDGYLLQVQELVTVQEGLCVHVPCSFSYPQDGWTDSDPVHGYWFRAGDRPYQDAPVATN

NPDREVQAETQGRFQLLGDIWSNDCSLSIRDARKRDKGSYFFRLERGSMKWSYKSQLNYKTKQLSVFVT

ALTHRPIEGRSDKTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTISKAKGQPREPQV

YTLPPSREEMTKNQVSLTCLVKGFYPSDIAVEWESNGQPENNYKTTPPVLDSDGSFFLYSKLTVDKSRW

QQGNVFSCSVMHEALHNHYTQKSLSLSPGK (SEQ ID NO: 56)
MEGDRQYGDGYLLQVQELVTVQEGLCVHVPCSFSYPQDGWTDSDPVHGYWFRAGDRPYQDAPVATN

NPDREVQAETQGRFQLLGDIWSNDCSLSIRDARKRDKGSYFFRLERGSMKWSYKSQLNYKTKQLSVFVT

ALTHRPDILILGTLESGHSRNLTCSVPWACKQGTPPMISWIGASVSSPGPTTARSSVLTLTPKPQDHGTSL

TCQVTLPGTGVTTTSTVRLDVSIEGRSDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDWLNGKEYKCKVSNKALPAPIE

KTISKAKGQPREPQVYTLPPSREEMTKNQVSLTCLVKGFYPSDIAVEWESNGQPENNYKTTPPVLDSDG

SFFLYSKLTVDKSRWQQGNVFSCSVMHEALHNHYTQKSLSLSPGK (SEQ ID NO: 57)
MEGDRQYGDGYLLQVQELVTVQEGLCVHVPCSFSYPQDGWTDSDPVHGYWFRAGDRPYQDAPVATN

NPDREVQAETQGRFQLLGDIWSNDCSLSIRDARKRDKGSYFFRLERGSMKWSYKSQLNYKTKQLSVFVT

ALTHRPDILILGTLESGHSRNLTCSVPWACKQGTPPMISWIGASVSSPGPTTARSSVLTLTPKPQDHGTSL

TCQVTLPGTGVTTTSTVRLDVSYPPWNLTMTVFQGDATASTALGNGSSLSVLEGQSLRLVCAVNSNPPA

RLSWTRGSLTLCPSRSSNPGLLELPRVHVRDEGEFTCRAQNAQGSQHISLSLSLQNEGTGTSRPVSQVT

LAAVGGIEGRSDKTHTCPPCPAPELLGGPSVFLFPPKPKDTLMISRTPEVTCVVVDVSHEDPEVKFNWYV

DGVEVHNAKTKPREEQYNSTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKLTVDKSRWQ

QGNVFSCSVMHEALHNHYTQKSLSLSPGK (SEQ ID NO: 58)
MEGDRKYGDGYLLQVQELVTVQEGLCVHVPCSFSYPKDDWTYSDPVHGYWFRAGDRPYQEAPVATNN

PDTEVQAETQGRFQLLGDRWSNDCSLSINDARKGDEGSYFFRLERGRMKWSYKSQLNYKAKQLSVFVT

ALTQRPDILIQGTLESGHPRNLTCSVPWACEQRMPPMISWIGTSVSSLGPITARFSVLTLIPKPQDHGTSLT

CQVTLPGTGVTTTRTVQLDVSYPPWNLTVTVFQGDDTASTALGNGSSLSVLEGQSLRLVCAVDSNPPAR

LSWTRGSLTLCPSQPWNPGLLELLRVHVKDEGEFTCQAENPRGSQHISLSLSLQNEGTGTARPVSEVTL

AAVGGIEGRSDKTHTCPPCPAPELLGGPSVFLFPPKPKDTLMISRTPEVTCVVVDVSHEDPEVKFNWYVD

GVEYHNAKTKPREEQYNSTYRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDSDGSFFLYSKLTVDKSRWQQ

GNVFSCSVMHEALHNHYTGKSLSLSPGK (SEQ ID NO: 59)
MEGDRKYGDGYLLQVQELVTVQEGLCVHVPCSFSYPKDDWTYSDPVHGYWFRAGDRPYQEAPVATNN

PDTEVQAETQGRFQLLGDRWSNDCSLSINDARKGDEGSYFFRLERGRMKWSYKSQLNYKAKQLSVFVT

ALTQRPDILIQGTLESGHPRNLTCSVPWACEQRMPPMISWIGTSVSSLGPITARFSVLTLIPKPQDHGTSLT

CQVTLPGTGVTTTRTVQLDVSYPPWNLTVTVFQGDDTASTALGNGSSLSVLEGQSLRLVCAVDSNPPAR

LSWTRGSLTLCPSQPWNPGLLELLRVHVKDEGEFTCQAENPRGSQHISLSLSLQNEGTGTARPVSEVTL

AAVGG
```

Subjects

The subject may be any animal, including a human and non-human animal. Non-human animals include all vertebrates, e.g., mammals and non-mammals, such as non-human primates, sheep, dogs, cats, cows, horses, chickens, amphibians, and reptiles, although mammals are envisioned as subjects, such as non-human primates, sheep, dogs, cats, cows and horses. The subject may also be livestock such as, cattle, swine, sheep, poultry, and horses, or pets, such as dogs and cats.

In one embodiment subjects include human subjects suffering from or at risk for the medical diseases and disorders described herein. The subject is generally diagnosed with the condition by skilled artisans, such as a medical practitioner.

The methods described herein can be employed for subjects of any species, gender, age, ethnic population, or genotype. Accordingly, the term subject includes males and females, and it includes elderly, elderly-to-adult transition age subjects adults, adult-to-pre-adult transition age subjects, and pre-adults, inducing adolescents, children, and Infants.

Examples of human ethnic populations include Caucasians, Asians, Hispanics, Africans, African Americans, Native Americans, Semites, and Pacific Islanders. The methods may be more appropriate for some ethnic populations such as Caucasians, especially northern European populations, as well as Asian populations.

The term subject also Includes subjects of any genotype or phenotype as long as they are in need of treatment, as described above. In addition, the subject can have the genotype or phenotype for any hair color, eye color, skin color or any combination thereof. The term subject includes a subject of any body height, body weight, or any organ or body part size or shape.

The invention will be described by the following non-limiting examples.

Example I

An rh.10 AAV serotype coding for anti-Siglec F, a murine-based, anti-murine eosinophil-specific monoclonal (Song et al., 2009: Zimmermann et al., 2008; Bochner et al., 2009) was prepared. An identical vector with the anti-SiglecF murine anti-eosinophil monoclonal sequence replaced by the sequence for anti-Siglec8, a humanized, human eosinophil-specific monoclonal (Croker et al., 2007; Varki et al 2006-Natku et al., 2003) is also prepared. To evaluate the effectiveness of LEXm03, a mouse model was employed in which AAVrh.10mIL5, another AAV vector, is administered intravenously to genetically modify the liver to persistently express and secrete high levels of murine interleukin 5 (IL5) which, in turn stimulates the bone marrow to persistently generate high blood levels of eosinophils (>100,000 eosinophils/$\mu L^3$), with tissue invasion with eosinophils and eventually death. The data demonstrate that LEXm03 induces apoptosis of eosinophils in vitro and in vivo, and markedly lowers the blood eosinophil levels in the mouse model of CEL-NOS (see FIG. 5). One outcome of this therapy is the permanent, complete suppression of eosinophils. This has been observed in human case reports and can be managed clinically (Franklin et al., 1981).

CEL-NOS is uncommon, representing approximately 1% of cases of chronic hypereosinophilia cases (Reuter et al. 2017), and thus is a rare orphan disorder. By example of the rare orphan hereditary disorders, there are several reasons to develop an effective therapy for CEL-NOS. First. CEL-NOS Is a fatal disorder with no available therapy. Because it is rare, there is no effective therapy, and the phenotype (hypereosinophilia) is easily measured, a small efficacy trial (following initial safety studies) should be sufficient for registration. Second, as with the rare hereditary disorders, if efficacious, pricing in the several hundred-thousand-dollar range should be feasible. Third, the rAAV is a platform strategy for a variety of much more common hypereosinophilic disorders.

CEL-NOS is a fatal malignant disorder representing an unmet medical need with no effective therapy. Attempts with therapies such as tyrosine kinase inhibitors, hydroxyurea, interferon-α or corticosteroids have all met with failure (Gotlieb et al., 2015; Helbing et al., 2012). Since the pathogenesis of CEL-NOS is unknown, and loss of organ function and eventual death is directly linked to high levels of blood eosinophils and the consequent invasions of eosinophils into tissues, the logical strategy to treat CEL-NOS is to suppress the numbers of blood eosinophils on a persistent basis. The present strategy to develop an effective therapy for CEL-NOS is a gene therapy approach, using an adeno-associated gene therapy vector to genetically modify liver hepatocytes to egress and secrete a monoclonal antibody that will bind to eosinophils, initiating apoptosis. First, Independent of the mechanisms underlying the hypereosinophilia that characterizes CEL-NOS, the strategy takes aim directly at the hypereosinophilia, the cause of the eosinophil organ invasion and hence suppression of the organ toxicity that leads to organ dysfunction and eventual death. Second, in contrast to the administration of the monoclonal itself which is associated with high peaks and trough, and requires administration every 2 to 4 wk depending on the monoclonal half-life, AAV-mediated gene egression of the monoclonal by the liver will provide, with a single administration, persistent levels of high titers of the therapeutic monoclonal. Third, while CEL-NOS is a relatively rare form of hypereosinophilia, the strategy for CEL-NOS represents a platform strategy developed initially for a fatal, currently unbeatable, disorder that has a high risk to safety profile. If sale and efficacious for CEL-NOS, the therapy can be developed for other more common hypereosinophilic syndromes including eosinophilic leukemias caused by genetic rearrangement and a variety of nonmalignant hypereosinophilic disorders such as eosinophilia vasculitis and other auto-immune disorders, hypereosinophilic syndrome, tropical pulmonary eosinophilia and atopic disorders including eosinophil esophagitis and asthma.

Figure 8:
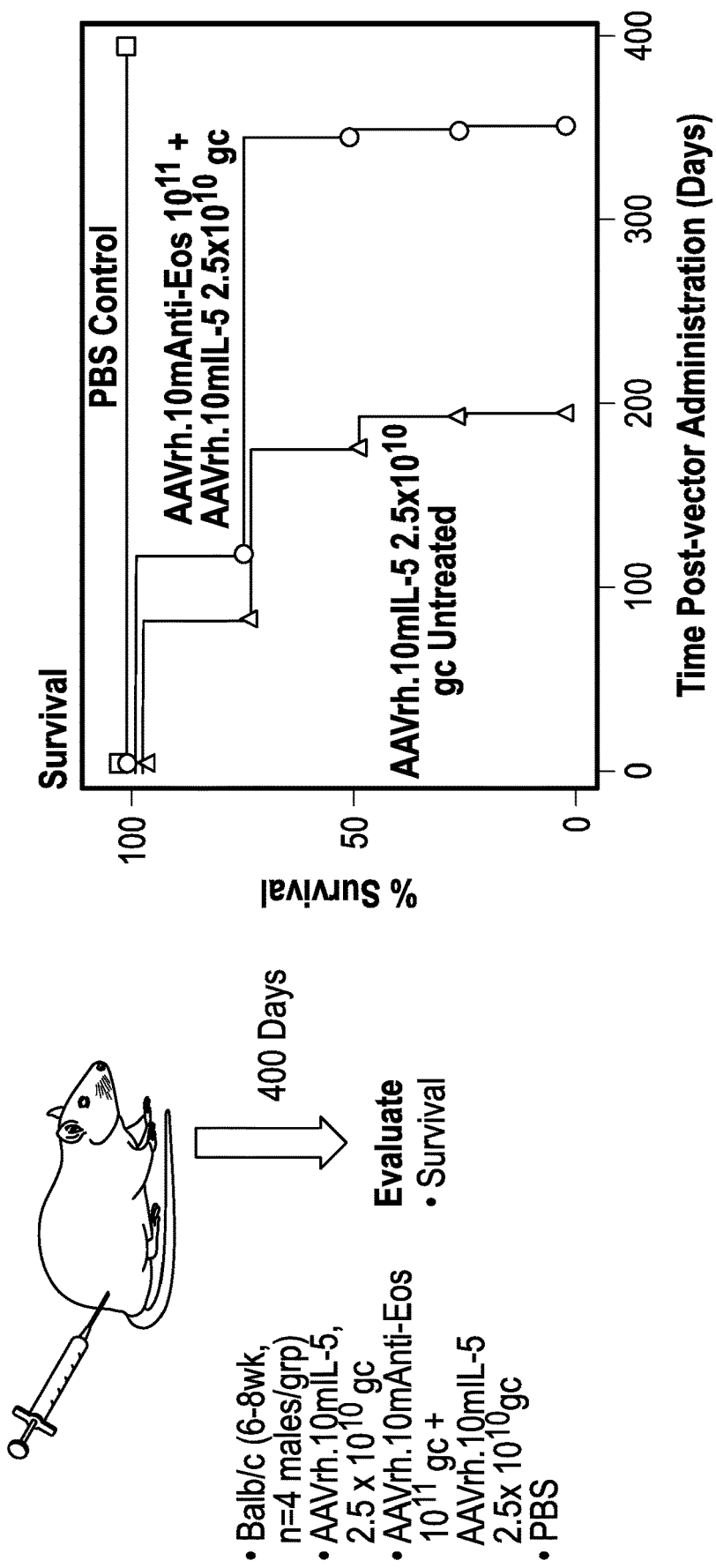
FIG. 8. AAVrh.10mAnti-Eos Reduces Mortality in CEL-NOS Murine Model (Balb/c). Median survival AAVrh.10mIL-5 alone 184 days, while AAVrh.10mAnti-Eos was 347 days.
Figure 10A:
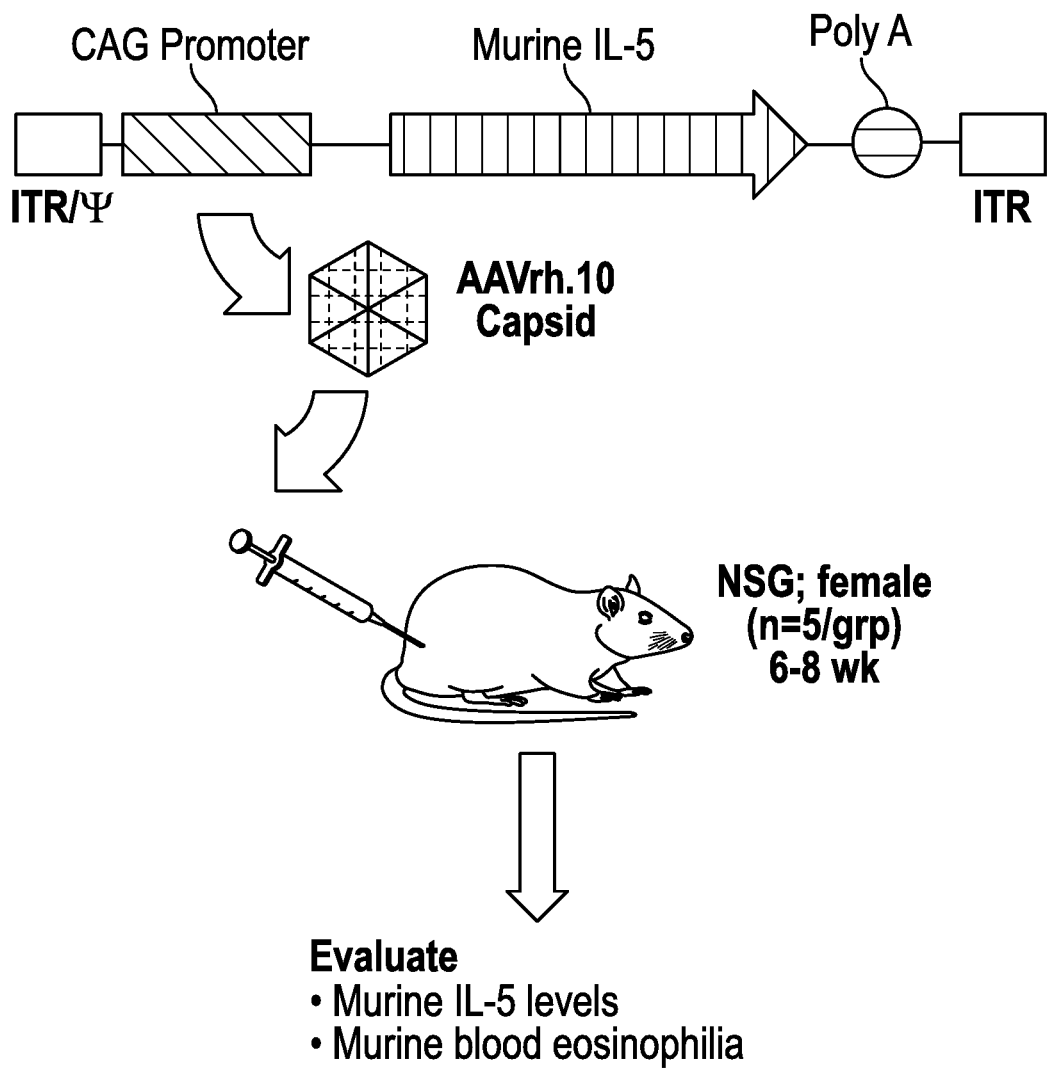
FIGS. 10A-D. CEL-NOS Murine Model (NSG). A) AAVrh.10mIL-5 was used to infect male Balb/c mice (r=5/group) at age 6-8 weeks, after which murine IL-5 levels and blood eosinophilia were evaluated. B) Absolute eosinophil count. C) Blood smear, PBS mouse. D) Blood smear AAVrh.10mIL-5 infected mouse at 2 weeks post-infection.
Figure 10B:
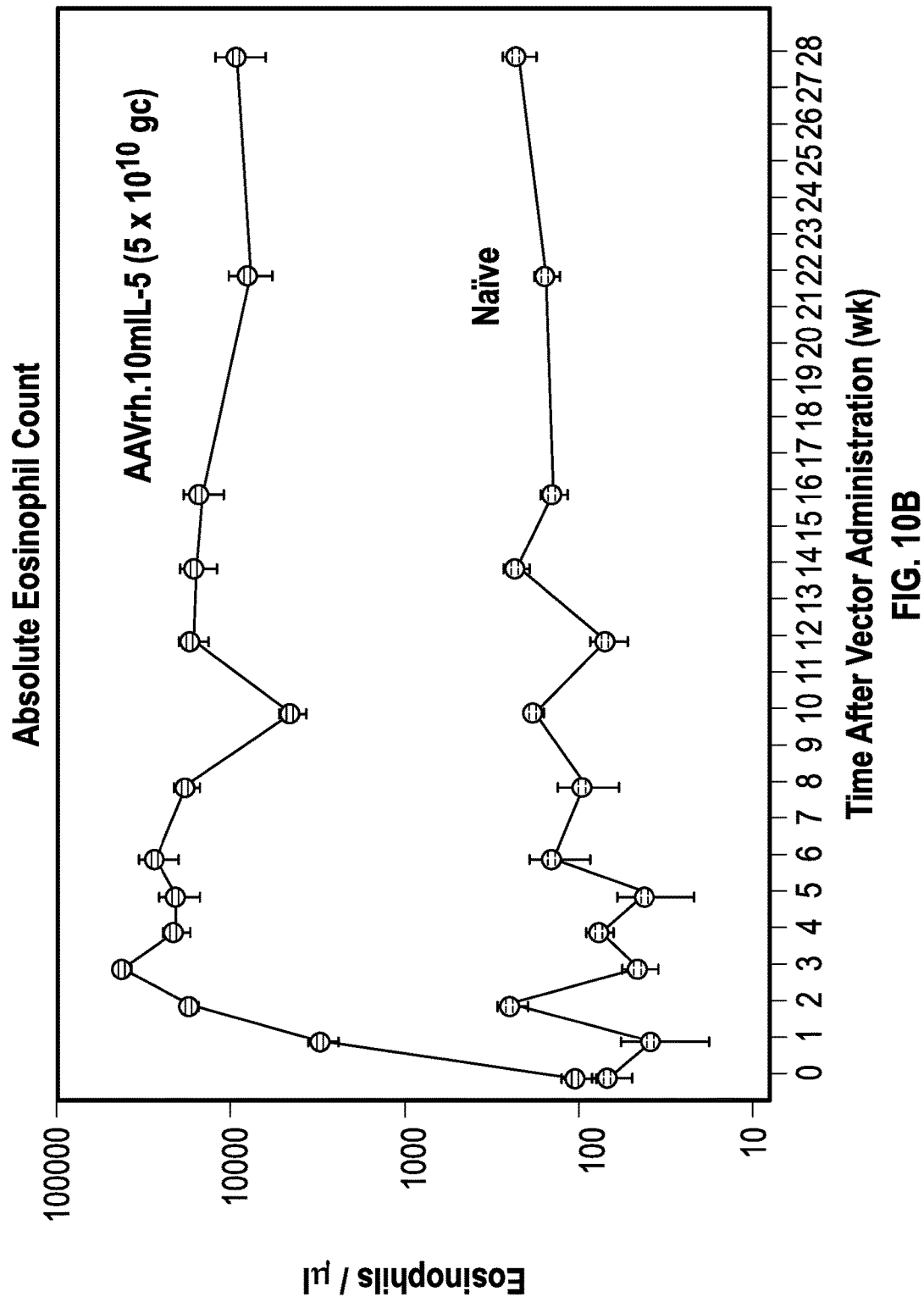
Figure 10C:
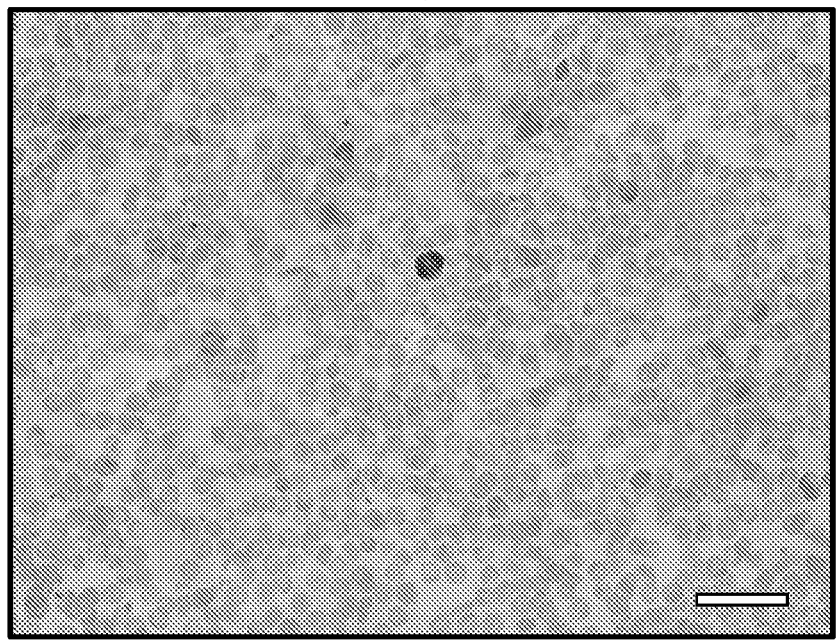
Figure 10D:
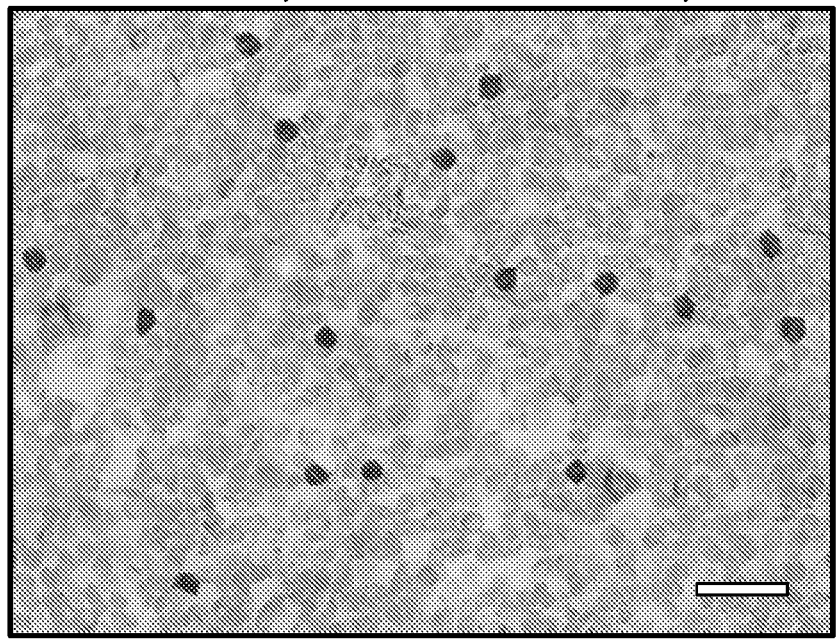
Figure 11A:
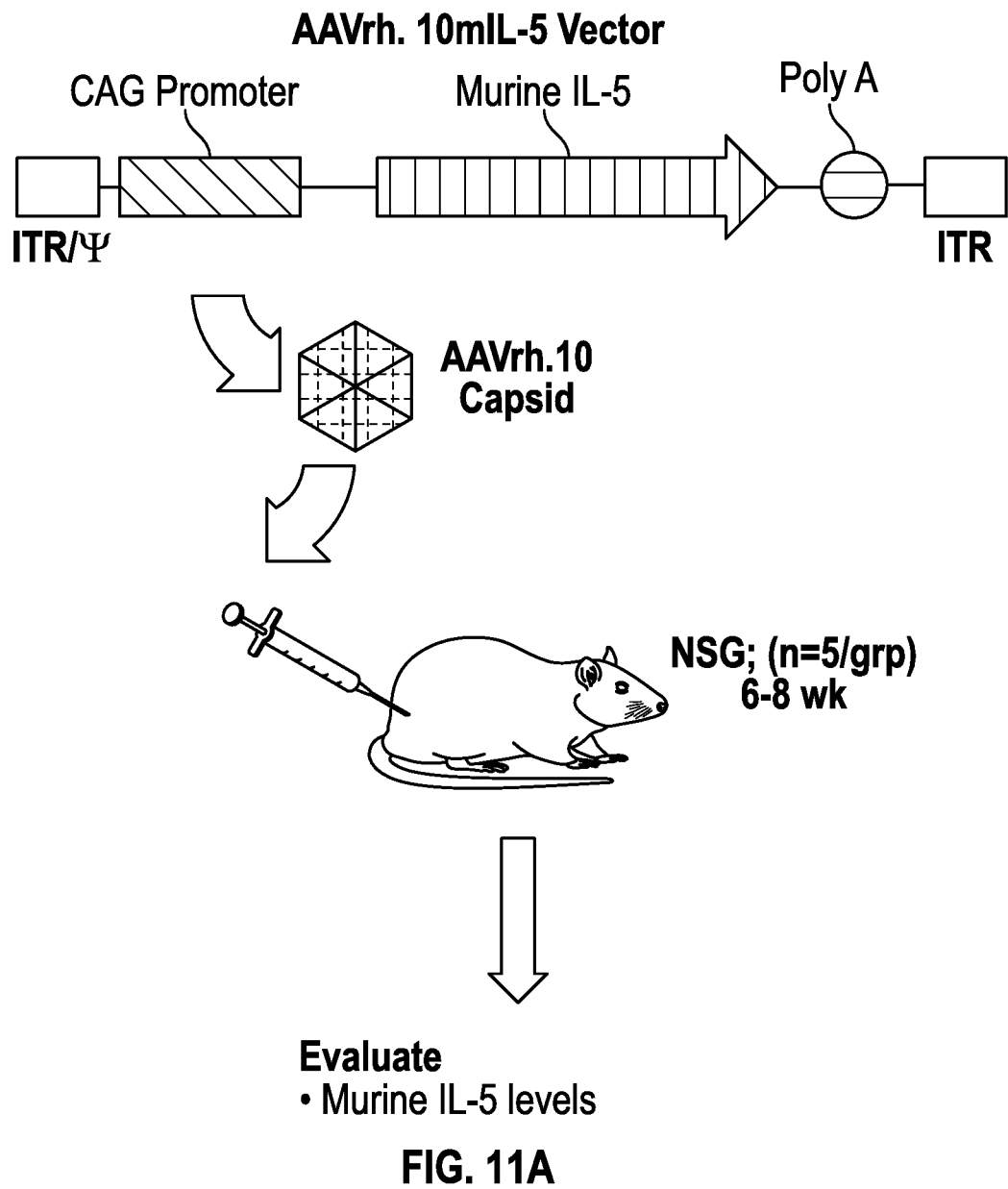
FIGS. 11A-B. Expression of AAVrh.10mIL-5 in Immunodeficient Mice (NSG). A) AAVrh.10mIL-5 was used to Infect NSG mice (n=5/group) at age 6-8 weeks, after which murine IL-5 levels (B) were evaluated.
Figure 11B:
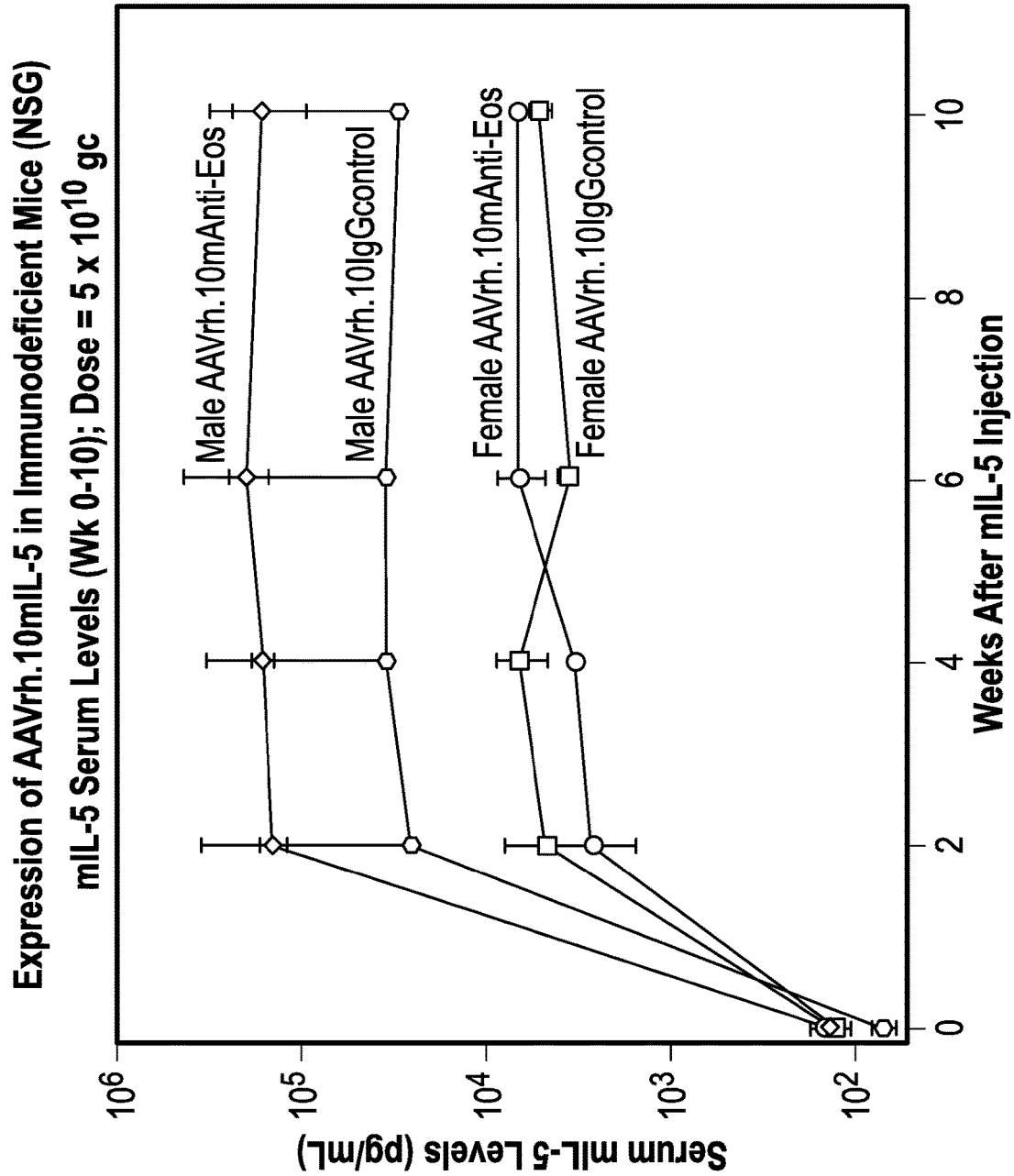
Figure 12:
FIG. 12. AAVrh.10mAnti-Eos Therapy in the CEL-NOS Murine Model (NSG).
Figure 12:
Figure 13A:
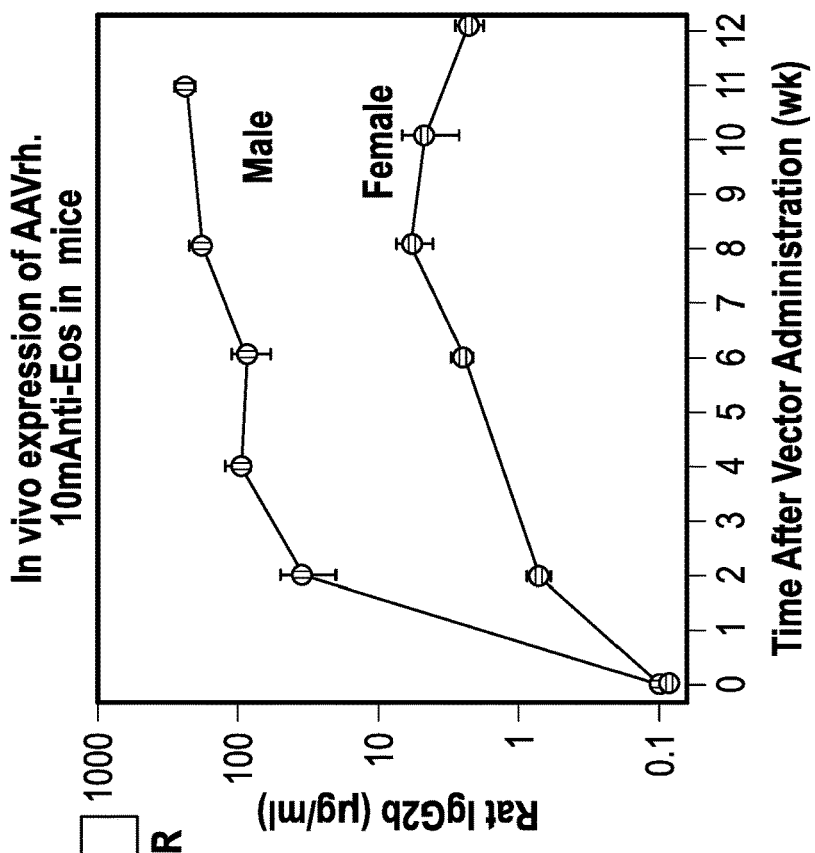
FIGS. 13A-B. Expression of AAVrh.10mAnti-Eos in NSG Mice. A) 6-8 week old NSG mice received $10^{11}$ gc AAVrh.10mAnti-Eos and serum levels of IgG2b were evaluated from 0-12 weeks. A) In vivo expression. B) In vitro apoptosis.
Figure 13A:
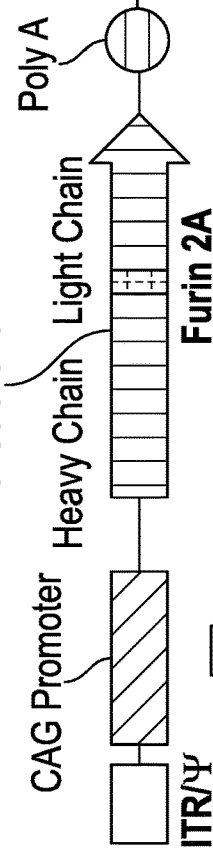
Figure 13A:
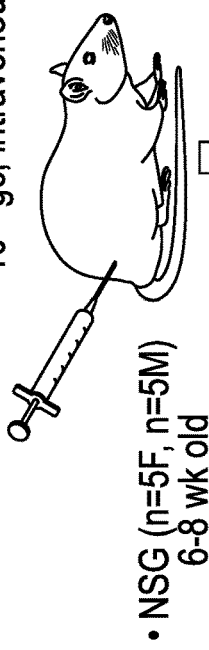
Figure 13B:
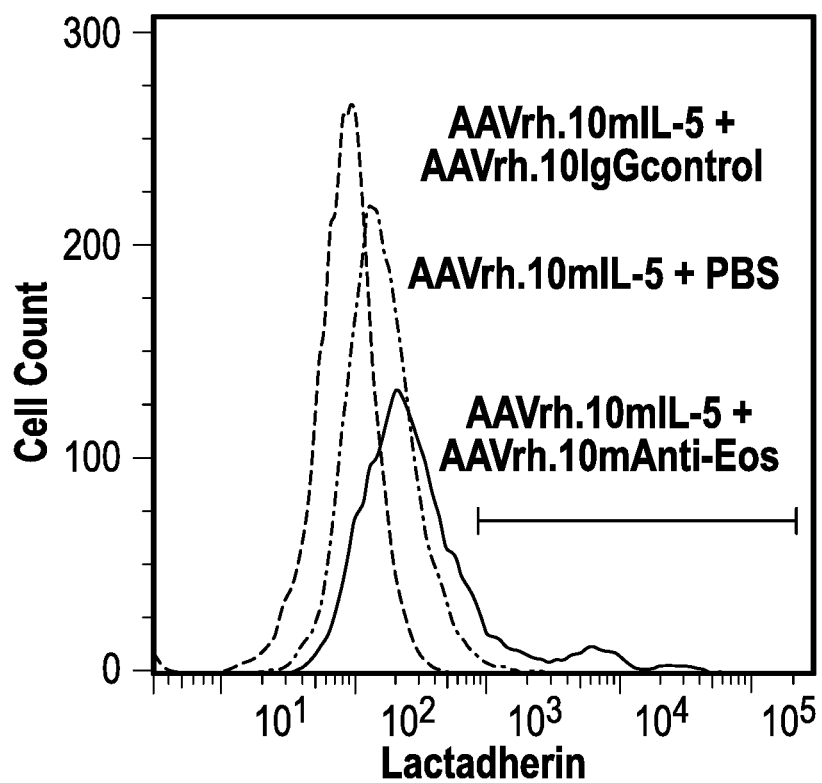
Figure 14A:
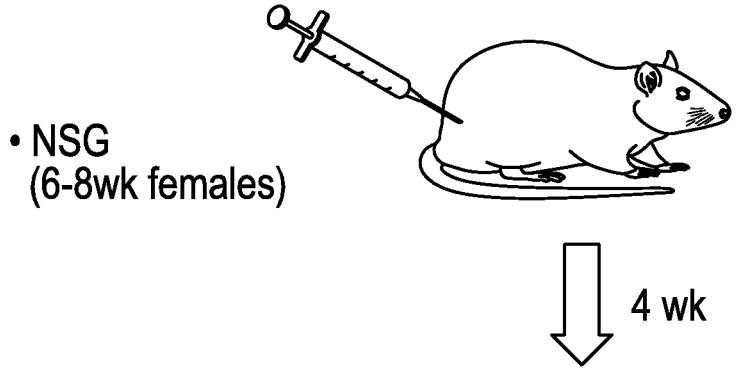
FIGS. 14A-B. AAVrh.10mAnti-Eos Reduces Eosinophil Numbers in the CEL-NOS Murine Model (NSG Females). A) Model. B) Absolute eosinophil counts.
Figure 14A:
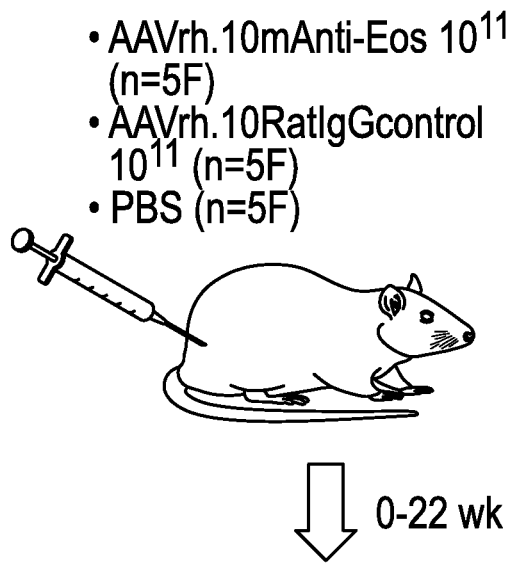
Figure 14B:
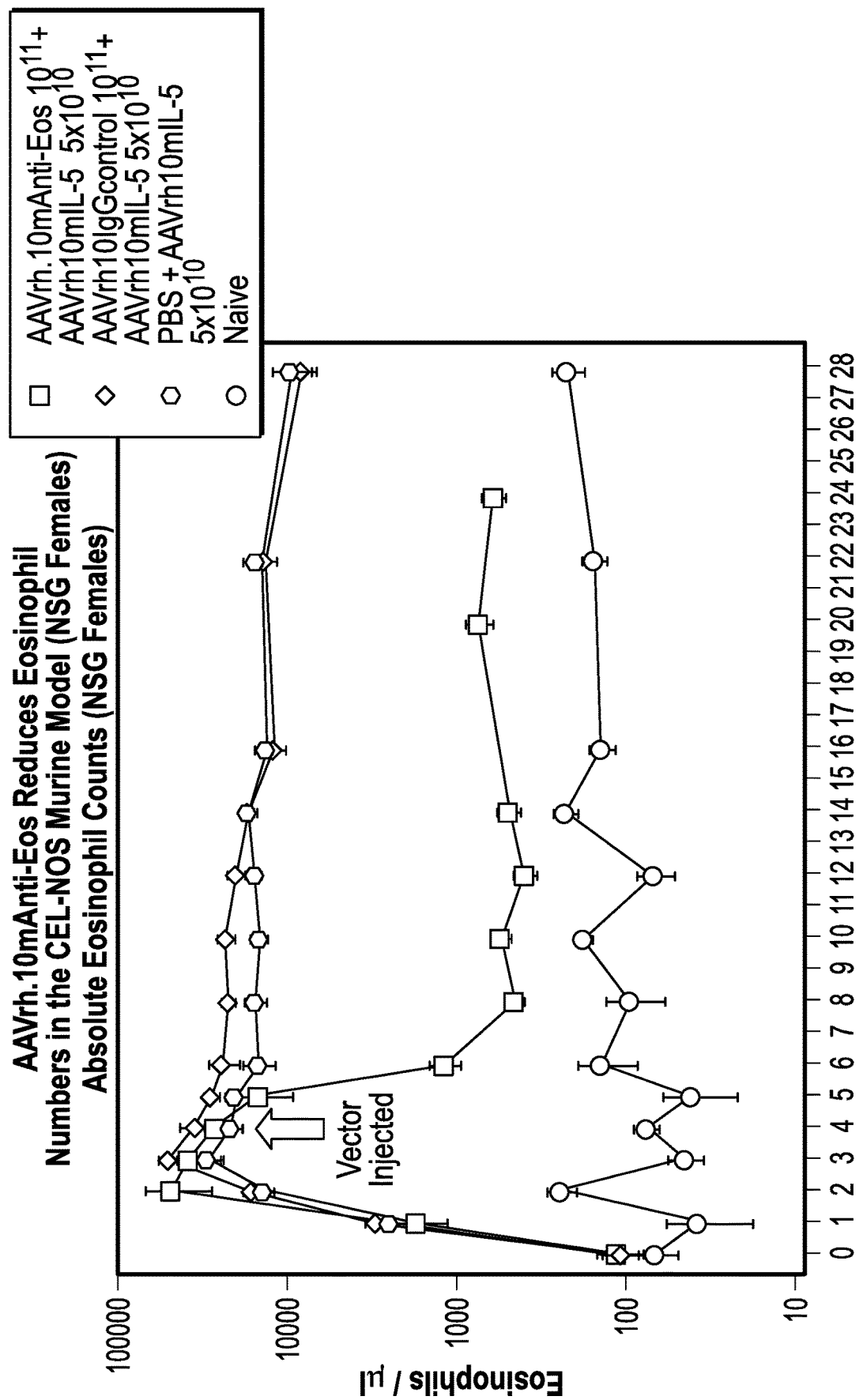
Figure 15A:
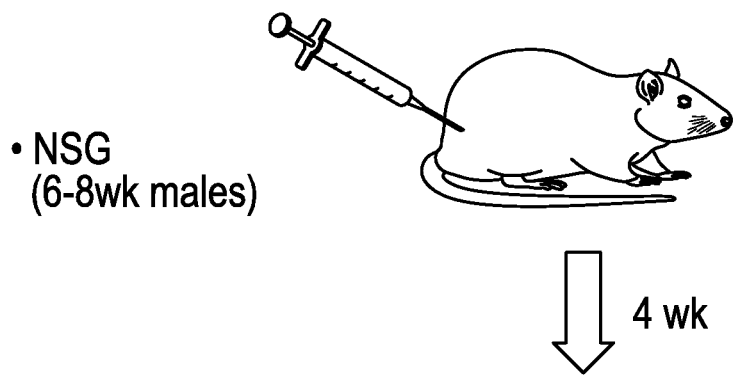
FIGS. 15A-B. AAVrh.10mAnti-Eos Reduces Eosinophil Numbers in the CEL-NOS Murine Model (NSG Males). A) Model. B) Absolute eosinophil counts.
Figure 15A:
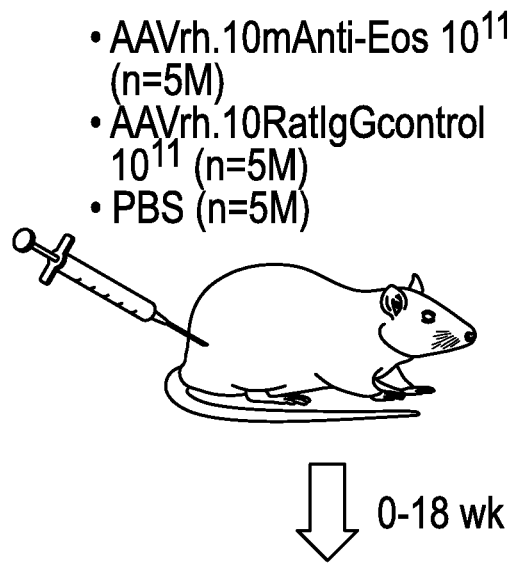
Figure 15B:
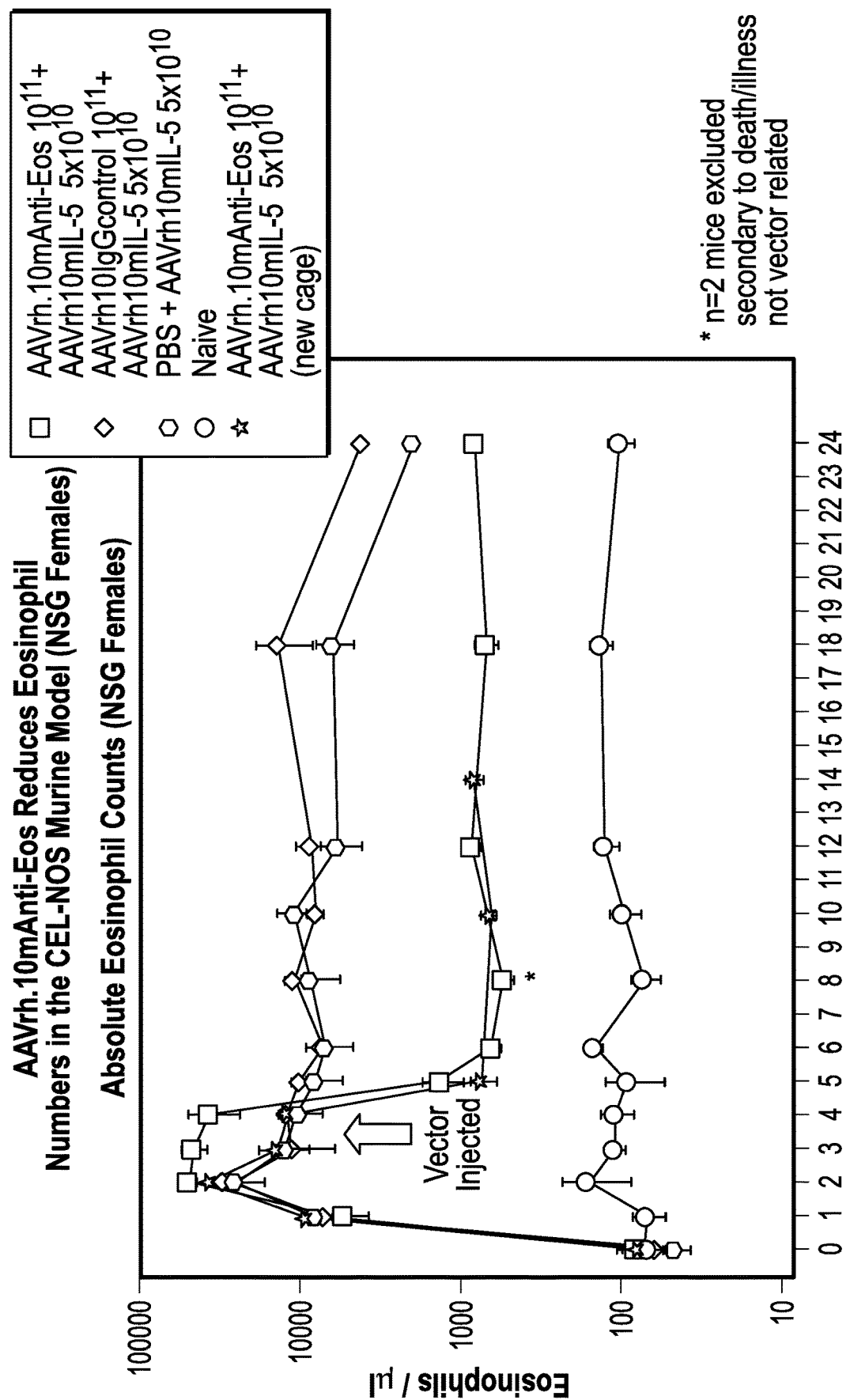
Figure 16A:
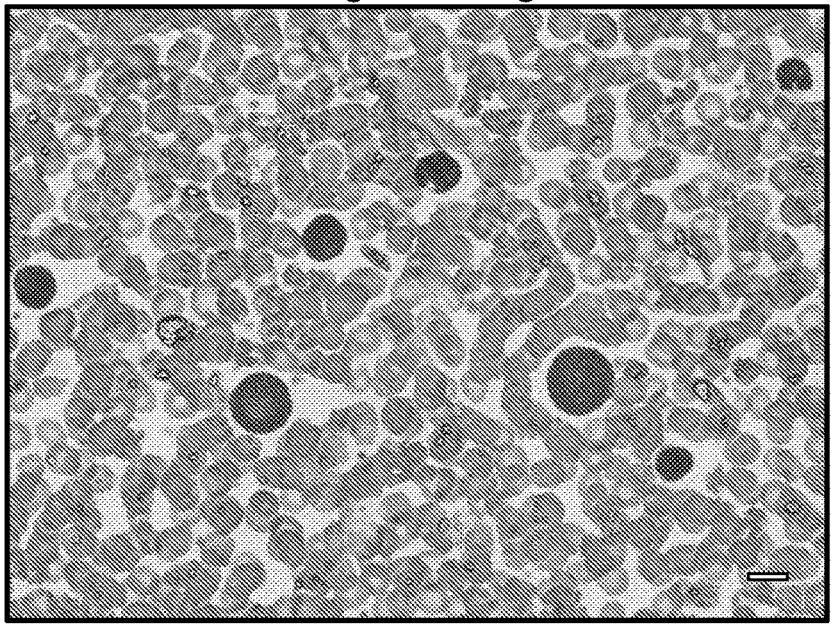
FIGS. 16A-B. AAVrh.10mAnti-Eos Reduces Eosinophil Numbers in the CEL-NOS Murine Model (Male NSG). A) Control blood smear. B) AAVrh.10mAnti-Eos treated blood smear.
Figure 16B:
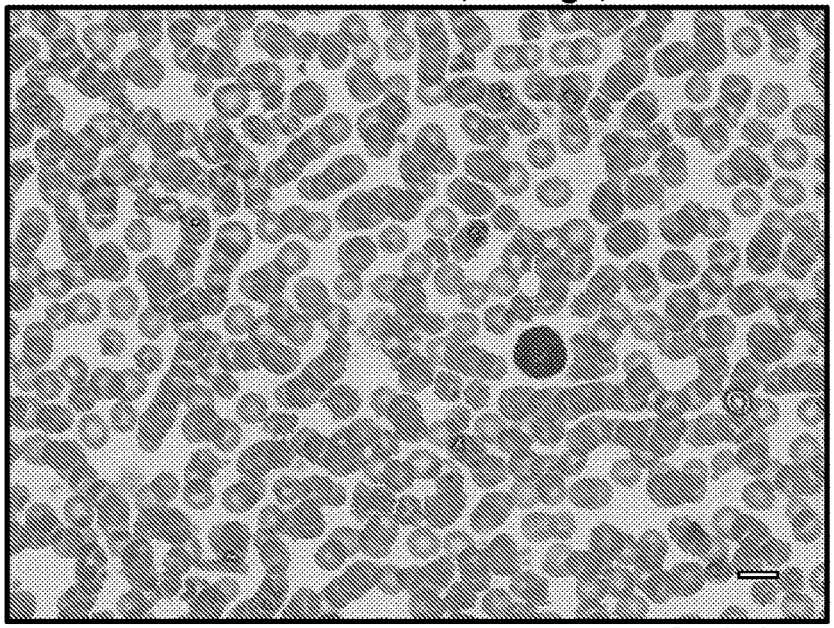

The data includes: (1) generation and characterization of LEXm03 (the therapeutic vector used in the murine system) and AAVrh.10mIL-5 (the murine interleukin-5 vector used to generate the murine CEL-NOS model; FIGS. 1 and 3); (2) characterization of the murine CEL-NOS model (FIGS. 3 and 4); and (3) efficacy of LEXm03 in the mouse CEL-NOS mouse model (FIGS. 7-8).

Dose-ranging studies demonstrate that LEXm03 induces apoptosis of murine eosinophils. The anti-eosinophil monoclonal generated in vitro and in vivo by LEXm03 is assessed for the induction of eosinophil apoptosis, in the context that the LEXm03 vector has been generated and shown to function in vitro and in vivo, and all of the assays are established, the doses of LEXm03 to effectively Induce apoptosis of murine eosinophils in vitro and in vivo are determined. For the in vivo assessment, dose-ranging studies as a function of increasing does of AAVrh.10mIL5 m CEL-NOS murine model are evaluated as a function of increasing doses of LEXm03, using the flow lactadherin assay.

TABLE 2

Dose-ranging Assessment of the Ability of LEXm03 to Induce
Eosinophil Apoptosis in the Murine Model of CEL-NOS

| CEL-NOS model AAVrh, 10 mIL 5 (gc) | LEXm03 or control (gc) | # animals | Assay time (wk)[2] |
|---|---|---|---|
| $10^8$, $10^9$, $10^{10}$ | $10^9$, $10^{10}$, $10^{11}$ | n = 5/condition | 4, 8 |

The AAVrh.10mIL-5 and LEXm03 is administered intravenously by tail vein to BALB/c mice at the same time. Different doses of AAVrh.10mIL5 will be used to induce different levels of blood eosinophilia. For each dose of AAVrh.10mIL5.3 doses of LEXm03 are tested, e.g., 9 different combinations. At each pairing of the 2 vectors n=5 mice will be evaluated, each at 2 time points (4 and 8 wk)

Flow cytometry lactadherin assay, see FIG. 5.

Using LEXm03, expand the preliminary murine efficacy studies demonstrate that intravenous administration of dose-ranging amounts of LEXm03 genetically modify hepatocytes to secrete the anti-eosinophil monoclonal antibody sufficient to significantly suppress blood eosinophil levels in the AAVrh.10mIL5 murine model of CEL-NOS with decreased tissue invasion of eosinophils and reduced morbidity and mortality.

Detailed Methods

LEXm03 (AAVrh.10mAnti-Eos). The vector Is comprised of the nonhuman primate-derived rh.10 capsid pseudo typed with AAV2 inverted terminal repeats surrounding the anti-Siglec-F expression cassette. The expression cassette consists of the cytomegalovirus (CMV) enhancer chicken-β-actin promoter (CAG promoter), the anti-Siglec-F cDNA sequence (clone 9C7, rat IgG2b), and rabbit β-globin polyadenylation signal. The anti-Siglec-F cDNA sequence was optimized for increased mRNA stability and to reduce the possibility of trans-inhibition by the mutant mRNA using mouse-biased codons and removal of mRNA instability elements, low (<30%) or rich (>80%) CAG regions, translation initiation sequences within the coding region and potential splicing signals. The optimized full length anti-Siglec-F cDNA sequence was synthesized and cloned into the pAAV plasmid-under control of the CAG promoter. The AAVrh.10m.anti-Eos vector was produced by co-transfection into human embryonic kidney 293T cells (HEK 293T; American Type Culture Collection) of the pAAV plasmid together with a plasmid carrying the AAV Rep proteins derived from AAV2 needed for vector replication, the AAVrh.10 viral structural (Cap) proteins VP1, 2 and 3 (which define the serotype of the produced rh.10 AAV vector) and the adenovirus helper functions of E2, E4 and VA RNA. The AAVrh.10 m.anti-Eos vector was purified by iodixanol gradient and QHP anion exchange chromatography as previously described. Vector genome titers were determined by quantitative TaqMan real-time PCR analysis. A vector coding for anti-anthrax protective antigen antibody (AAVrh.10mIgG control) was used as control for the in vivo studies.

AArh.10mIL-5. The sequence of murine IL-5 was obtained from Genbank (NM_010558.1) The AAVrh.10mIL-5 vector is comprised of the nonhuman primate-derived rh.10 capsid pseudotyped with AAV2 inverted terminal repeats surrounding the murine IL-5 expression cassette. The expression cassette consists of the cytomegalovirus (CMV) enhancer chicken-β-actin promoter (CAG promoter), the IL-5 cDNA sequence, and rabbit β-globin polyadenylation signal. The mIL-5 cDNA sequence was optimized for increased mRNA stability and to reduce the possibility of trans-inhibition by the mutant mRNA using mouse-biased codons and removal of mRNA instability elements, low (<30%) or rich (>80%) GC regions translation initiation sequences within the coding region and potential splicing signals. The optimized full length mIL-5 cDNA sequence was synthesized and cloned into the pAAV plasma-under control of the CAG promoter. The AAVrh.10mIL-5 vector-was produced by co-transfection into human embryonic kidney 293T cells as described for LEXm03.

In vivo expression of AAVrh.10m.anti-SiglecF in BALB/C mice. To assess LEXm03 directed expression of anti-Eos in vivo, male and female Balb/C mice, age 6 to 8 wk, were injected (intravenously in 100 μL) with a one-time dose of AAVrh.10m.anti-Eos (see Table 2 for doses), or AAVrh.10mIgG control and 100 μl PBS control Blood (100 μL) was collected from the tail vein and allowed to dot, 23° C. followed by centrifugation at 5,000 RPM for 10 min to collect serum. Anti-SiglecF was measured at 0 wk, and at time points over the course of 8 wk by ELISA (Abeam), conducted per the manufacturers protocol IL-5 mouse model. In order to quickly and robustly derive a mouse model of CEL-NOS to test vector efficacy, murine IL-5 was overexpressed from an AAVrh.10 vector (AAVrh.10m.IL-5). After intravenous administration of increasing doses of AAVrh.10mIL-5 ($10^5$. $10^9$, $10^{10}$ gc), mIL-5 levels in serum were highly elevated in a dose dependent manner when measured by ELISA (Abeam).

Lactadherin assay. White blood cells (WBC) isolated from mice concurrently treated with AAVrh.10mIL-5 (2.5× $10^{10}$ gc)±LEXm03 or AAVrh.10mIgG control ($10^{11}$ gc) were stained with anti-CCR3 to identify eosinophils and incubated with lactadherin, which binds exposed phosphatidylserine, to identify cells in the early stages of apoptosis and analyzed by flow cytometry.

Eosinophil counts. Peripheral blood absolute eosinophil counts were monitored every 2 wk using the ADVIA hematology system cell counter and blood smears stained with hematoxylin and eosin.

Survival. Mice were observed daily after vector injection for signs of deterioration in health. If deemed moribund (severe shaking, labored breathing, wheezing, cyanosis, and no activity after prodding; all without recovery), mice were sacrificed, and the date of death was recorded.

Organ damage/function. Blood levels of organ damage biomarkers were assessed after collection of blood by cardiac puncture at time of sacrifice. The samples were centrifuged (15 min, 4° C., 500 g) and serum collected. The following biochemical parameters were measured in the serum as markers of multiple organ injury or dysfunction: liver—serum aspartate aminotransferase (AST); kidney—blood urea nitrogen (BUN); cardiac—creatine kinase MB isoenzyme (CK-MB); endothelial—serum endocan (ELISA, mouse Endocan DuoSet, RID Systems); systemic inflammation—tumor necrosis factor-alpha (TNF-α).

Eosinophil infiltration in tissues (Immunofluorescence). Organs collected from the mice were immediately placed in Carnoy's Solution (60% EtOH, 30% chloroform, and 10% acetic acid) 2 hr. followed by 100% EtOH 1 hr, and 70% EtOH for long term storage. Organ paraffin embedding and histology/side mounting performed by Histoserv (Germantown, MD). Slides were deparaffinized with Histoclear (Fisher-Scientific), rehydrated and placed in steam bath 88° C. 20 min for antigen retrieval. Tissue sections were then blocked with Super Bock Butter (Thermo Fisher Scientific) at 4° C. for 1 hr followed by incubation with primary antibody, rabbit anti-mouse MBP polyclonal Ab (Mybiosource), 20 μg/ml in 3% FBS, 0.1% saponin in PBS, at 4° C. overnight. Tissue sections were then incubated with secondary Ab, donkey anti-rabbit IgG—Alexa fluor 647. (Invitrogen) 6 μg/ml in 3% FBS, 0.1% Saponin in PBS, at 4° C. 1 hr. Tissue sections were then mounted with Prolong Gold antifade reagent with DAPI (Thermo Fisher Scientific) and evaluated by fluorescence microscopy using a Zeiss Axiovert 200M fluorescence microscope.

Statistics. The 2 studies have n=5 mice/per assay parameter subgroup; this number provides statistical power for the efficacy study with allowing for an outlier result while giving a reasonable chance that substantial effects can be seen. For example, if we assert a single variable to be the outcome measurement we can show that using n=5 per group gives us a good chance of observing the effect, of the treatment. If we assert that the coefficient of variation of measurement is 60% for both groups then n=5/group provides the ability to see a 3.2-fold difference in mean score between 2 groups with p<0.05 at 95% power. All data will be presented as means±standard error of the mean (SEM) unless otherwise stated. Differences between groups will be analyzed using Student's two-tailed t test).

Example II

Eosinophils are highly specialized bone marrow-derived granulocytic cells that play a role in combating parasites and other pathogens. In normal individuals, eosinophils represent <5% of white blood cells, persist in the circulation 8-12 hr. and survive in tissues 8-12 days. If eosinophils invade tissues in sufficient numbers, they cause organ damage and dysfunction due to release of cytotoxic mediators.

Chronic eosinophilic leukemia-not otherwise specific (CEL-NOS) is a fatal disorder of which there is no effective therapy. A therapy for CEL-NOS as well as other eosinophilic disorders is described herein that employs an adeno-associated virus gene therapy vector to genetically modify cells m a mammal, e.g., in the liver, to generate persistent levels of an anti-eosinophil monoclonal antibody that induces programmed cell death of eosinophils.

CEL-NOS is a subtype of chronic eosinophilic leukemia with persistent elevation of blood eosinophils >1.5×10$^3$/μL, associated with increased myeloblasts in the marrow negative for Philadelphia chromosome. BCR-ABL, rearrangements of PD6FRB, FIP1L1-PDGFRA fusion. PDGF2A or PGFR1, other clonal cytogenetic abnormality myeloproliferative neoplasms. The pathogenesis is unknown. It typically affects individuals with a median age 62 yr, characterized by dysfunction of organs associated with eosinophil invasion, weight loss, cough, weakness, diarrhea, splenomegaly, hepatomegaly, cardiac and lung dysfunction and survival of about 2 yr. CEL-NOS is unresponsive to tyrosine kinase inhibitors, hydroxyurea, interferon-α or corticosteroids.

Since the pathogenesis of CEL-NOS is unknown, the most direct therapy is to suppress the number of eosinophils in blood, thus suppressing eosinophil tissue invasion and organ dysfunction. The efficacy of gene therapy for an exemplary eosinophilic disorder, e.g., CEL-NOS, using an adeno-associated virus (AAV) vector coding for an anti-eosinophil monoclonal was determined. AAVrh.10mAnti-Eos (LEXm03) was administered intravenously to genetically modify cells, e.g., liver hepatocytes, to 4 express and secrete a murine-specific anti-eosinophil monoclonal. e.g., having a sequence encoded by SEQ ID NO: 1 or 2, or both, that induces murine eosinophil apoptosis LEXh03 codes for a humanized anti-eosinophil monoclonal specific for human eosinophils, e.g., having a sequence encoded by SEQ ID NO:5, 6 or 8, or a combination thereof. Other antibody sequences may be employed, e.g., any of SEQ ID Nos. 3-6, 8-32, 40-41, 43-44, or 46-51, or sequences having at least 90%, 92%, 94%, 95%, 96%, 97%, 98% or 99%, amino acid sequence identity thereto, e.g., in framework sequences or one or more CDRs thereof. In one embodiment, the antibody has variable region sequences with at least 90%, 92%, 94%, 95%, 96%, 97%, 98% or 99%, amino acid sequence identity to SEQ ID Nos. 3-6, 8-32, 40-41, 43-44, or 46-51, including sequences with 1, 2, 3, 4, or 5 substitutions relative to SEQ ID Nos. 3-6, 8-32, 40-41, 43-44, or 46-51, in one or more framework sequences or one or more CDRs, or any combination thereof.

To evaluate the effectiveness of LEXm03, a CEL-NOS mouse model was prepared using another AAV vector (AAVrh.10mIL5) administered intravenously to genetically modify the liver to express and persistently secrete high levels of murine interleukin-5 (IL5), which in turn, stimulates bone marrow to persistently generate high blood levels of eosinophils (>100,000 eosinophilia/μL), with tissue invasion by eosinophils and eventually death. The data demonstrate that LEXm03 induces apoptosis of eosinophils in vitro and in vivo, and markedly lowers the blood eosinophil levels.

REFERENCE

Bandeira-Melo et al., *J. Allergy Clin. Immunol.*, 169:393 (2002).
Bochner, *Clin. Exp. Allergy*, 39:317 (2009).
Bolus et al., *J. Leukoc. Biol.*, 98:467 (2015).
Brigden and Graydon, *Arch. Pathol. Lab Med.*, 121:963 (1997).
Crocker et al., *Nat. Rev. Immunol.*, 1:255 (2007).
Curtis and Ogbogu, *Clin. Rev. Allergy Immunol.*, 50:240 (2016).
Falchi and Verstovsek, *Immunol. Allergy Clin. North Am.*, 35:439 (2015).
Franklin and Goetzl, *Ann. Intern. Med.*, 24:352 (1981).
Gleich and Adolphson, *Adv. Immunol.*, 32:177 (1986).
Gotlib and Akin, *Semin. Hematol.*, 42:128 (2012).
Gotlib, *Am. J. Hematol.*, 90: 1077 (2015).
Helbig et al., *Am. J. Hematol.*, 87:643 (2012).
Hogan et al., *Clin. Exp. Allergy*, 38:709 (2008).
Horiuchi and Weller, *Am. J. Respir. Cell. Mol. Biol.*, 33:70 (1997).
Kato et al., *Int. Arch. Allergy Immunol.*, 137 Suppl 1:17 (2005).
Lacy, *Pharmacol. Ther.*, 107:358 (2005).
Morgan et al., *Am. J. Respir. Cell. Mol. Bid.*, 23:169 (2005).
Nutku et al., *Blood.* 101:5014 (2003).
Park and Bochner, *Allergy Asthma Immunol. Res.*, 2:87 (2010).
Reiter and Gotlib. *Blood.* 128:704 (2017).
Rothenberg and Hogan, *Annu. Rev. Immunol.* 24:147 (2006).
Roufosse et al., *Semin. Hematol.*, 42:138 (2012).
Saito et al., *Ann. Allergy Asthma Immunol.*, 93:594 (2004).
Slifman et al., *J. Immunol.*, 137:2913 (1966).
Song et al., *Clin. Immunol.*, 131:157 (2009).
Song et al., *J. Immunol.*, 183:5333 (2009).
Tefferi et al., *Br. J. Haematol.*, 133:468 (2006).
Trulson et al., *Clin. Exp. Allergy.* 37:208 (2007).
Valent et al., *Expert Rev. Hematol.*, 5:157 (2012).
Varki et al., *Glycobiology.* 16:1R (2006).
Venge et al., *Clin. EXP. Allergy.* 29:1172 (1999).

Young et al., Wheater's Functional Histology: Elsevier (2006).
Zheutlin et al., *J. Immunol.*, 133:2160 (1984).
Zimmermann et al., *Allergy.* 63:1156 (2008).

All publications, patents and patent applications are Incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of inhibiting or treating leukemia in a mammal, comprising:
    administering to the mammal a composition comprising a recombinant adeno-associated virus (rAAV) expression vector comprising an open reading frame encoding an antibody that binds sialic acid binding Ig-like lectin 8, in an amount effective to inhibit or treat the leukemia, wherein the open reading frame encodes a sequence having three CDRs of SEQ ID Nos. 5 and 29.

2. The method of claim 1 wherein the mammal is a human.

3. A method of inhibiting or treating a hypereosinophilic disease selected from asthma, esophagitis, tropic pulmonary eosinophilia, an infectious disease, an allergic or atopic disease, gastroenteritis, a hepatobiliary disease, meningitis, a cardiac disorder, a genitourinary disorder, an immunodeficiency, an endocrinological disorder, a pulmonary disorder, a skin disease, rheumatoid arthritis, or vasculitis in a mammal, comprising: administering to the mammal a composition comprising a rAAV expression vector comprising an open reading frame encoding an antibody that binds sialic acid binding Ig-like lectin 8 in an amount effective to reduce eosinophilia in the mammal, wherein the open reading frame encodes a sequence having three CDRs of SEQ ID Nos. 5 and 29.

4. The method of claim 1 wherein the capsid of the rAAV is an AAV1, AAV2, AAV3, AAV4, AAV5, AAV6, AAV7, AAV8, AAV9 or AAVrh10 capsid.

5. The method of claim 1 wherein the antibody is a chimeric, humanized, scFv, Fv, Fab', single-chain molecules containing one VL, one VH antigen-binding domain and one or two constant domains, or fully human antibody.

6. The method of claim 1 wherein the antibody binds eosinophils.

7. The method of claim 1 wherein the rAAV expression vector encodes an antibody comprising a polypeptide comprising SEQ ID Nos. 5 and 29.

8. The method of claim 1 wherein the composition is systemically administered.

9. The method of claim 1 wherein the composition is administered to the central nervous system or intracranially.

10. The method of claim 1 wherein the antibody is expressed from an endogenous viral promoter.

11. The method of claim 1 wherein the antibody is expressed from an exogenous promoter in the viral expression vector that is operably linked to the open reading frame.

12. The method of claim 11 wherein the promoter is inducible.

13. The method of claim 1 wherein the viral expression vector further comprises a suicide gene.

14. The method of claim 1 wherein the open reading frame encodes a sequence having SEQ ID No. 5.

15. The method of claim 1 wherein the open reading frame encodes a sequence having SEQ ID No. 29.

16. The method of claim 3 wherein the capsid of the rAAV is an AAV1, AAV2, AAV3, AAV4, AAV5, AAV6, AAV7, AAV8, AAV9 or AAVrh10 capsid.

17. The method of claim 3 wherein the antibody is a chimeric, humanized, scFv, Fv, Fab', single-chain molecules containing one VL, one VH antigen-binding domain and one or two constant domains, or fully human antibody.

18. The method of claim 3 wherein the composition is systemically administered.

19. The method of claim 3 wherein the antibody is expressed from an exogenous promoter in the viral expression vector that is operably linked to the open reading frame.

20. The method of claim 3 wherein the open reading frame encodes a sequence having SEQ ID No. 5 or SEQ ID No. 29.

* * * * *